United States Patent [19]

Briet et al.

[11] Patent Number: 5,116,954

[45] Date of Patent: May 26, 1992

[54] PHARMACEUTICALLY USEFUL FLAVONOIC COMPOUNDS CONTAINING AT LEAST ONE SUBSTITUENT ON THE BENZOPYRANONE RING MOIETY

[75] Inventors: Philippe Briet, Felix Faure; Jean-Jacques Berthelon, Bonhomme; Francois Collonges, Chemin de Halage, all of France

[73] Assignee: Lipha, Lyonnaise Industrielle Pharmaceutique, Lyon, France

[21] Appl. No.: 388,738

[22] Filed: Aug. 2, 1989

Related U.S. Application Data

[63] Continuation of Ser. No. 178,315, Apr. 6, 1988, abandoned.

[51] Int. Cl.$^5$ .............. C07D 311/30; C07D 311/78; C07D 215/33; C07D 335/06; C07D 345/00; A61K 31/35

[52] U.S. Cl. .................................. 534/551; 540/1; 544/151; 544/376; 546/112; 546/121; 546/153; 546/269; 548/154; 548/194; 548/201; 548/204; 548/348; 549/72; 549/220; 549/313; 549/318; 549/389; 549/400; 549/401; 549/403; 514/75; 514/150; 514/183; 514/233.5; 514/312; 514/320; 514/337; 514/365; 514/368; 514/393; 514/402; 514/413; 514/432; 514/453; 514/456

[58] Field of Search .............. 534/551; 549/401, 403, 549/23, 220, 313, 318, 389, 400, 403; 514/456; 540/1; 544/151, 376; 546/112, 121, 153, 269; 548/154, 194, 201, 204, 348

[56] References Cited

U.S. PATENT DOCUMENTS

| | | | |
|---|---|---|---|
| 4,097,582 | 6/1978 | Briet et al. | 549/403 X |
| 4,115,567 | 9/1978 | Doria et al. | 549/403 X |
| 4,148,900 | 4/1979 | Doria et al. | 549/403 X |
| 4,157,334 | 6/1979 | Doria et al. | 549/403 |
| 4,594,345 | 6/1986 | Enomoto et al. | 549/403 X |
| 4,602,034 | 7/1986 | Briet et al. | 549/403 X |
| 4,634,768 | 1/1987 | Inoue et al. | 549/403 X |

FOREIGN PATENT DOCUMENTS

| | | | |
|---|---|---|---|
| 0080934 | 6/1983 | European Pat. Off. | 549/403 |
| 0123113 | 3/1984 | European Pat. Off. | 549/403 |
| 0278176 | 6/1988 | European Pat. Off. | 549/403 |
| 0283761 | 9/1988 | European Pat. Off. | 549/403 |
| 1270567 | 3/1961 | Fed. Rep. of Germany | 549/403 |
| 2051269 | 2/1972 | Fed. Rep. of Germany | 549/403 |
| 2059296 | 2/1972 | Fed. Rep. of Germany | 549/403 |
| 3517950 | 5/1985 | Fed. Rep. of Germany | 549/403 |
| 2536397 | 5/1984 | France | 549/403 |
| 139037 | 2/1967 | New Zealand . | |
| 152204 | 8/1971 | New Zealand . | |
| 1078756 | 8/1967 | United Kingdom | 549/403 |

OTHER PUBLICATIONS

Rubin et al, Lancet, vol. 11, No. 8567, pp. 1081–1082 (1987).

Wiltrout et al, "The Journal of Immunology", vol. 140, No. 9, pp. 1 to 5 (1988).

Chemical Abstracts, vol. 104, No. 15, Apr. 14, 1986, p. 19, column 1, abstract No. 122574b, Columbus, OH, USA; G. Atassi et al: "Synthesis . . . "

Chemical Abstracts, vol. 107, No. 17, Oct. 26, 1987, p. 27, column 1, abstract No. 146923c, Columbus, OH, USA; M. Ching et al.: "Induction of . . . "

(List continued on next page.)

Primary Examiner—Patricia L. Morris
Assistant Examiner—Fiona T. Powers
Attorney, Agent, or Firm—Oblon, Spivak, McClelland, Maier & Neustadt

[57] ABSTRACT

Substituted six-membered benzo-fused heterocycles of the formula (I)

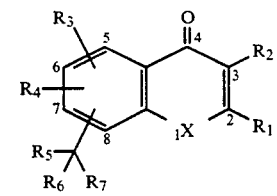

in which:
X=O, NH, S→(O)$_n$ (n=0 or 2);
R$_1$ is phenyl, phenyl substituted by methoxy, hydroxy, chlorine, fluorine, diethylaminoethoxy, phenoxy, 2-methyl-4-thiazolyl, 2-amino-4-thiazolyl, phenyl, amino, nitro, terbutyl, carboxymethyl, acetamido, dimethyltriazenyl, benzoyl, hexyl, undecyl, trifluoromethyl, carbamoyl; or R$_1$ is trifluoromethyl, pyridyl-2,pyridyl-4;
R$_2$ is H, methoxy, hydroxy; or
R$_1$ and R$_2$ are —CH=CH—CH=CH—;
R$_3$ and R$_4$ are methoxy, hydroxy, fluorine or form a fused benzene ring;
CR$_5$R$_6$R$_7$ is carboxymethyl, —CH$_2$—PO$_3$H, —CH$_2$—PO(oET)$_2$, 4-methylpiperazinyl, aminomethyl,3-4-5-trimethoxyphenylaminomethyl, acetyl, bromoacetyl, hydroxyethyl, acetoxyethyl, mercaptomethyl, acetylthiomethyl, methoxy-carbopnyl-thiomethyl, —CH—CONH$_2$,

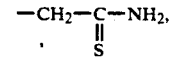

substituted thiazolyl, substituted furanone, imidazo(1,2-a)pyridinyl, indolizinyl, or R$_4$ and R$_5$ form a fused benzene ring on the positions 5 and 6, 6 and 8 or 7 and 8 are disclosed. These compounds possess anticancer activity in particular antipancreatic cancer activity together with immunomodulating activity.

12 Claims, No Drawings

OTHER PUBLICATIONS

*Journal of The Chemical Society*, Perkin Transactions I 1977, No. 9, pp. 948-953; S. Antus et al.: "Synthesis of tachrosin . . . "

*Chemical Abstracts*, vol. 89, No. 13, Sep. 25, 1978, p. 867, column 2, abstract No. 108951n, Columbus, OH, USA; P. Roveri et al.: "New . . . "

*Journal of Heterocyclic Chemistry*, vol. 11, No. 4, Aug. 1974, pp. 469-470; I. Lalezari et al.: "Selenium Heterocycles XIV. (1) 2,6-. . . "

*Patent Abstracts of Japan*, vol. 10, No. 56, (C-331) (2113), Mar. 6, 1986; & JP-A-60 199817 (Rikagaku Kenkyusho) 09.10.85.

*Patent Abstracts of Japan*, vol. 8, No. 71, (C-217) (1508), Apr. 3, 1984; & JP-A-58 225083 (Nippon Shinyaku K.K.) 27.12.1983.

*Patent Abstracts of Japan*, vol. 9, No. 196 (C-297) (1919), Aug. 13, 1985; & JP-A-60 64976 (Hokuriku Seiyaku K.K.) 13.04.1985.

*Patent Abstracts of Japan*, vol. 9, No. 138, (C-286) (1861), Jun. 13, 1985; & JP-A-60 23379 (Shinnihon Yakuhin K.K.) 05.02.1985.

PHARMACEUTICALLY USEFUL FLAVONOIC COMPOUNDS CONTAINING AT LEAST ONE SUBSTITUENT ON THE BENZOPYRANONE RING MOIETY

This application is a continuation of application Ser. No. 07/178,315, filed on Apr. 6, 1988, now abandoned.

BACKGROUND OF THE INVENTION

1. Field of the Invention

This invention relates to substituted flavonoid compounds, and to these compounds used as medicaments.

2. Discussion of the Background

U.S. Pat. No. 4,602,034 discloses (oxo-4-4H-(1)-benzopyran-8-yl) alkanoic acids and their derivatives, represented by the formula:

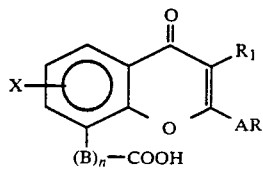

wherein, in the above formula, AR is hydrogen, a phenyl radical which may or may not be substituted, thenyl, furyl, naphthyl, a lower alkyl, cycloalkyl, aralkyl radical, B is a lower alkyl radical, $R_1$ is hydrogen or a phenyl radical, X is hydrogen or a lower alkyl or alkoxy radical, and n is equal to 1, as well as some salts, esters, amino esters and amides of these compounds.

Fifty-seven specific examples of this class of compounds are reported in U.S. Pat. No. 4,602,034. These compounds are disclosed to be useful in the control of tumors, however their reported anticancer activity is limited to P388 lymphocytic leukemia and carcinoma 38 of the colon.

Rubin et al in "Lancet", 8567, 11:1081–1082 (1987) disclose that flavone-8-acetic acid, one of the compounds disclosed by U.S. Pat. No. 4,602,034, inhibits ristocetin-induced platelet agglutination and prolongs bleeding time.

Wiltrout et al in "The Journal of Immunology", vol. 140, no. 9, pp. 3261–3265 (1988) disclose that flavone-8-acetic acid, the same compound discussed above, also augments systemic natural killer cell activity and synergizes with interleukin-2 (IL-2) for treatment of murine renal cancer.

In view of the wide variety of cancers found in animals, and in particular in humans, however there is a strongly felt need for other materials useful in the treatment of other types of cancers, e.g., pancreatic cancer, not to mention the fact that there is also a strongly felt need for new compounds possessing other desirable pharmaceutical properties, e.g., the property of inhibiting platelet agglutination. Such pharmaceutical properties would also include immunomodulatory properties.

SUMMARY OF THE INVENTION

Accordingly, it is an object of this invention to provide a novel class of compounds possessing anticancer activity.

It is another object of this invention to provide a novel class of compounds possessing antipancreatic cancer activity.

It is another object of this invention to provide a novel class of compounds possessing immunomodulatory properties.

It is another object of this invention to provide a novel class of compounds possessing immunomodulatory properties where these properties include the property of stimulating the production of interferon (IFN).

It is another object of this invention to provide a novel class of compounds possessing immunomodulatory properties where these properties include the property of stimulating the formation of killer cells.

It is another object of this invention to provide a novel class of compounds possessing the property of inhibiting platelet agglutination.

It is another object of this invention to provide compounds possessing very favorable threshold values in the exploitation of their properties (threshold value being defined as the difference between the lowest level of administration of the compound at which the activity is observed and the level of administration at which the compound becomes toxic to the patient).

It is another object of this invention to provide pharmaceutical compositions containing at least one of the compounds provided by this invention.

It is another object of this invention to provide a method for the treatment of a patient suffering from a condition which the compounds of the present invention are able to ameliorate or treat, by administering to this patient at least one of the compounds of the invention.

The inventors have now discovered a class of compounds which satisfy all of the above objects of the invention and other objects which will become apparent from the description of the invention given hereinbelow. These compounds have the formula (I):

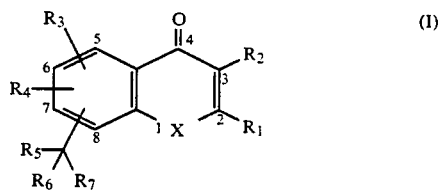

wherein:

X is NH, O, Se, or S(O)$_n$, wherein n is 0, 1 or 2;

R$_1$ is H; C$_{1-7}$ alkyl; naphthyl; phenyl; phenyl substituted by at least one member selected from the group consisting of halogens, C$_{1-12}$ alkyl, trifluoromethyl, hydroxyl, C$_{1-6}$ alkoxy, −(C$_{1-6}$—alkylene)−COOR$_{10}$, nitro, −(C$_{1-6}$ alkyl)−carboylamino, benzoyl, C$_{1-6}$−(alkyl)carboyl, CONR$_{10}$R$_{11}$, (where R$_{10}$ and R$_{11}$ are each independently H or C$_{1-6}$ alkyl), NR$_{10}$R$_{11}$, —N=N—NR$_{10}$R$_{11}$, phenyl substituted by at least one halogen atom, phenol, —O−(C$_{1-6}$ alkylene)−NR$_{10}$R$_{11}$, thiazolyl, and thiazolyl substituted by C$_{1-6}$ alkyl or amino; or R$_1$ is pyridyl; pyridyl substituted by at least one member selected from the group consisting of C$_{1-6}$ alkyls and halogens; trifluoromethyl; benzoyl or benzyl;

R$_2$ is H; phenyl; OH; C$_{1-3}$ alkyl; or C$_{1-3}$ alkoxy;

R$_3$ and R$_4$ are each, independently of each other, H; C$_{1-6}$ alkyl; OH; C$_{1-6}$ alkoxy; or halogen;

R$_5$ is H; C$_{1-3}$ alkyl; CN; or COOR$_{10}$

R$_6$ is H; C$_{1-6}$ alkyl; OH; −(C$_{1-3}$ alkylene)−CN; COOR$_{10}$; —O—CO−(C$_{1-6}$ alkyl); or $R_5$ and $R_6$ together are a group $=CR_{10}R_{11}$, or a group $=NOH$, or a group $=O$ or a group $=CHR_{12}$ (where $R_{12}$ is phenyl pyridyl, phenyl substituted by at least one member selected from the group consisting of halogen atoms, trifluoromethyl and $C_{1-3}$ alkyls or pyridyl substituted by at least one member selected from the group consisting of halogen atoms, trifluoromethyl and $C_{1-3}$ alkyls);

$R_7$ is H; CHO; COOR$_{10}$; —CH=CH—COOR$_{10}$; —P(O)(OR$_{10}$R$_{11}$)$_2$; NR$_{13}$R$_{14}$ (where $R_{13}$ and $R_{14}$ are independently H; phenyl; phenyl substituted by a halogen atom or a $C_{1-3}$ alkyl group or a group —COOR$_{10}$, —CO—O—CH(CH$_3$)—COOR$_{10}$, morpholinyl, —C(CH$_2$OH)$_2$(CH$_3$), imidazolinyl, ($C_{1-6}$ alkylene)—OH, ($C_{1-6}$ alkylene)—COOR$_{10}$, or $C_{1-3}$ alkoxy, or wherein $R_{13}$ and $R_{14}$ together with the nitrogen atom to which they are both bound from an imidazole or a N-($C_{1-3}$ alkyl)-piperazinyl); or $R_7$ is —CO-($C_{1-6}$ alkyl); —S-($C_{1-6}$ alkyl); —SH; —S—CO-($C_{1-3}$ alkyl); —S-(CH$_2$)$_m$COOR$_{10}$ (with $0<m\leq 6$); —CO—O-($C_{1-6}$ alkylene)—NR$_{10}$R$_{11}$; —O-($C_{1-6}$ alkylene)—NR$_{10}$R$_{11}$; —NR$_{10}$NR$_{10}$R$_{11}$; $C_{1-6}$ alkyl; —CONR$_{10}$R$_{11}$; —CSNR$_{10}$R$_{11}$; thiazolyl; thiazolyl substituted by at least one member selected from the group consisting of —NH$_2$, $C_{1-3}$ alkyl, phenyl, and COOR$_{10}$; —NH—CO-($C_{1-3}$-alkyl); or ($C_{1-3}$-alkylene) CH(NH$_2$-(COOH); or —CR$_5$R$_6$R$_7$ is a group of one of the formulae

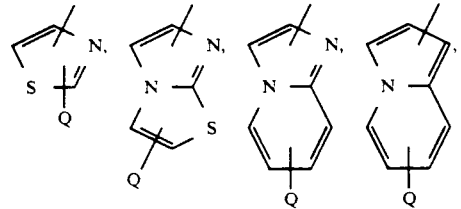

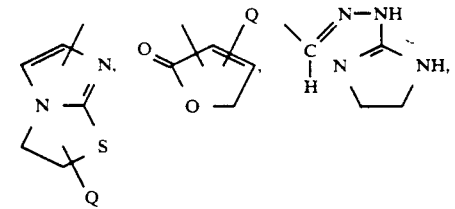

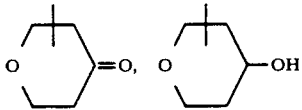

wherein

Q is at least one member selected from the group consisting of H; COOR$_{10}$; phenyl; —O-($C_{1-3}$-alkylene)—COOR$_{10}$; $C_{1-3}$-alkyl; —O—CS—NR$_{10}$R$_{11}$; —O-($C_{1-3}$-alkylene)—NR$_{10}$R$_{11}$; OH; $C_{1-3}$ alkoxy; and NR$_{10}$R$_{11}$; or wherein any two of $R_3$, $R_4$, $R_5$, $R_6$ and $R_7$ together form a benzene ring; or a benzene ring substituted by ($C_{1-3}$-alkylene)—COOR$_{10}$;($C_{1-3}$-alkyl)—OH, COOR$_{10}$, or ($C_{1-3}$-alkylene)—O—CO-($C_{1-3}$-alkyl); or a naphthalene system; or a napahthalene system substituted by ($C_{1-3}$-alkylene)—COOR$_{10}$, ($C_{1-3}$-alky)—OH, COOR$_{10}$, or ($C_{1-3}$-alkylene)—O—CO-($C_{1-3}$-alkyl); and physiologically acceptable salts thereof, with the proviso that when —CR$_5$R$_6$R$_7$ is situated at the 8-position of formula (I) and X is O, (i) when $R_2$, $R_3$, $R_4$, $R_5$ and $R_6$ are all H and $R_7$ is CN, $R_1$ is other than phenyl, 2-thenyl, 3,4-dimethoxy phenyl, 3-methoxy phenyl, para-tolyl, 2-furyl, 2-naphthyl, 4-methoxy phenyl, benzyl, methyl, or cyclohexyl;

(ii) when $R_2$, $R_3$, $R_4$, $R_5$ and $R_5$ are all H and $R_7$ is COOH, $R_1$ is other than phenyl, 2-thenyl, 3-methoxy phenyl, 3,4-dimethoxy phenyl, 2-furyl, para-tolyl, 2-naphthyl, 4-methoxy phenyl, cyclohexyl, benzyl, or methyl;

(iii) when $R_2$, $R_3$, $R_4$, $R_5$ and $R_6$ are all H and $R_7$ is —O—CH$_2$CH$_2$—N(C$_2$H$_5$)$_2$, $R_1$ is other than phenyl, 2-thenyl, para-tolyl, or 4-methoxy phenyl;

(iv) when $R_2$, $R_3$, $R_4$, $R_5$ and $R_6$ are all H and $R_7$ is

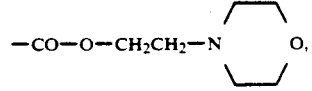

$R_1$ is other than phenyl;

(v) when $R_2$, $R_3$, $R_4$, $R_5$ and $R_6$ are all H and $R_7$ is —CO—O-(CH$_2$)$_3$N(CH$_3$)$_2$; $R_7$ is other than phenyl;

(vi) when $R_2$, $R_3$, $R_4$, $R_5$ and $R_6$ are all H and $R_7$ is —CO—O—C$_2$H$_5$, $R_1$ is other than phenyl;

(vii) when $R_2$, $R_3$, $R_4$, $R_5$ and $R_6$ are all H and $R_7$ is —CO—O—CH$_3$, $R_1$ is other than phenyl or 2-thenyl;

(viii) when $R_2$, $R_3$, $R_4$, $R_5$ and $R_6$ are all H and $R_7$ is —CO—O—Na, $R_1$ is other than phenyl;

(ix) when $R_2$, $R_3$, $R_4$, $R_5$ and $R_6$ are all H and $R_7$ is —CO—O—CH$_2$CH$_2$OH, $R_1$ is other than phenyl;

(x) when $R_2$, $R_3$, $R_4$, $R_5$ and $R_6$ are all H and $R_7$ is —CO—NH—CH$_2$CH$_2$N(C$_2$H$_5$)$_2$, $R_1$ is other than phenyl;

(xi) when $R_2$, $R_4$, $R_5$ and $R_6$ are all H, $R_3$ is methyl at the 6-position of formula (I) (6—CH$_3$) and $R_7$ (xii) when $R_2$, $R_4$, $R_5$ and $R_6$ are all H, $R_3$ is 6—CH$_3$ and $R_7$ is COOH$_3$, $R_1$ is other than phenyl;

(xiii) when $R_2$, $R_4$, $R_5$ and $R_6$ are all H, $R_3$ is 6—CH$_3$ or 6—OCH$_3$ and $R_7$ is —CO—O—CH$_2$CH$_2$—N(C$_2$H$_5$)$_2$, $R_1$ is other than phenyl;

(xiv) when $R_2$ and $R_3$ are H, $R_4$ is H or 6—CH$_3$, $R_5$ is methyl, $R_6$ is —COOC$_2$H$_5$, and $R_7$ is —COOC$_2$H$_5$, $R_1$ is other than phenyl;

(xv) when $R_2$ and $R_3$ are H, $R_4$ is H or 6—CH$_3$, $R_5$ is H, $R_6$ is CH$_3$ and $R_7$ is COOH, $R_1$ is other than phenyl;

(xvi) when $R_2$, $R_3$, $R_4$ and $R_5$ are all H, $R_6$ is CH$_3$ and $R_7$ is —CO—O—CH$_2$CH$_2$N(C$_2$H$_5$)$_2$, $R_1$ is other than phenyl;

(xvii) when $R_2$, $R_3$, $R_4$ and $R_7$ are all H, $R_5$ and $R_6$ are $=O$, $R_1$ is other than phenyl;

(xviii) when $R_2$, $R_3$, $R_4$, and $R_5$ are all H and —CR$_5$R$_6$R$_7$ is —CH=CH—COOH, —CH=CH—COOCH$_2$CH$_2$N(C$_2$H$_5$)$_2$,

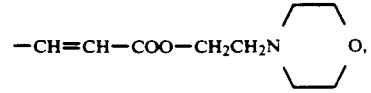

—CH$_2$CH(COOC$_2$H$_5$)$_2$, or —CH$_2$CH$_2$COOH, R$_1$ is other than phenyl;

(xix) when R$_2$ and R$_3$ are both H, R$_4$ is 6—CH$_3$ or 6—OCH$_3$, R$_6$ and R$_7$ are H and R$_5$ is CN, R$_1$ is other than phenyl;

(xx) when R$_2$ and R$_3$ are H, R$_4$ is 6—OCH$_3$ or 6—OH, and R$_5$ and R$_6$ are H and R$_7$ is COOH, R$_1$ is other than phenyl;

(xxi) when R$_2$ is phenyl, R$_3$ and R$_4$ are H, R$_5$ and R$_6$ are =O, or R$_6$ is CN or COOH, R$_1$ is other than phenyl.

DETAILED DESCRIPTION OF THE PREFERRED EMBODIMENTS

The compounds of the present invention have been surprisingly discovered to possess anticancer activity, in particular antipancreatic cancer activity, and better threshold characteristics as compared to available compounds, namely those disclosed in U.S. Pat. No. 4,602,034. These compounds have further surprisingly been discovered to also possess immunomodulatory activity, in particular they stimulate the formation of interferon and of killer cells. And, it is believed that the compounds of the present invention inhibit platelet agglutination and prolong bleeding times. These compounds are therefore useful in the treatment of cancers, e.g., pancreatic cancers, and are believed to be useful in the suppression of clot formation.

In conjunction with Messrs. Robert H. Wiltrout and Ronald L. Hornung of the National Cancer Institute at Frederick, Md., U.S.A., the inventors have also found that the compounds of the present invention surprisingly potentiate the activity of interleukin-2 (IL-2).

The terms "alkyl", "alkylene", and "alkoxy" used in this document refer to linear or branched or cyclic, saturated or unsaturated alkyl, alkylene, or alkoxy groups unless otherwise specified.

The term "halogen" in this document refers to fluoro, chloro, bromo and iodo, preferably fluoro and chloro, and most preferably fluoro, unless otherwise specified.

The term "salt" is used in this document in accordance with its accepted definition to include all possibilities in which the compound of the invention is either the cationic or the anionic component of the salt. The compounds of the invention have acidic and/or basic functionalities which can of course be both present in the same molecule.

With acidic functionalities, the salts of the compounds are obtainable through reaction with either an organic or an inorganic base. Such bases include all bases known to be useful to make physiologically acceptable salts, for example, Na$_2$CO$_3$, NaHCO$_3$, KOH, NaOH, NH$_3$ and bases of the formula NR$_{27}$R$_{28}$R$_{29}$ where R$_{27}$, R$_{28}$ and R$_{29}$ are H, C$_{1-6}$ alkyl, C$_{1-6}$ hydroxyalkyl, etc.

With basic functionalities, the salts of the compounds are obtained by reaction with inorganic or organic acids. The acids which can be used are all the acids known to be useful to make physiologically acceptable salts, for example, HCl, HBr, HI, phosphoric acid, phosphonic acid, para—toluené sulfonic acid, formic acid, oxalic acid, fumaric acid, etc. These salt forms of the compounds are generally readily soluble in water, and permit administration of the compounds in solution to a patient.

The present invention also provides pharmaceutical compositions containing at least one of the present compounds. These pharmaceutical compositions are prepared in accordance with the general knowledge in the pharmaceutical art. They can be pharmaceutical compositions suitable for intravenous injection, oral administration, nasal administration (e.g. a nasal spray) or eye drops. The pH of these compositions is preferably at a value compatible with human administration, e.g. the pH is at a value of between 7 and 8.

These compounds can be administered following any protocol known in this art. For example, they can be administered intravenously at a dosage of 1 to 10 g m$^{-2}$ for a period of time of 1 to 24 hours or longer.

The compounds of the present invention, when not in solution in a pharmaceutically suitable carrier, are preferably lyopholized before storage. In lypholized form they are more easily dissolved in a pharmaceutical medium.

In a preferred embodiment, when R$_1$ is C$_{1-7}$ alkyl, the preferred alkyl groups are C$_{1-3}$ alkyl, e.g., methyl, ethyl, n-propyl or iso—propyl. When R$_1$ is a substituted phenyl group, the substituents are C$_{1-3}$ alkyl, halogen, trifluoromethyl, hydroxy, C$_{1-3}$ alkoxy or nitro. Phenyl substituted by one halogen atom is particularly preferred. When R$_1$ is a substituted pyrridyl, the same preferred substituents for phenyl as given above, are also preferred.

The groups R$_2$, R$_3$ and R$_4$ are preferrably H. Groups R$_5$ and R$_6$ are preferably =CR$_{10}$R$_{11}$ with R$_{10}$=R$_{11}$=H.

Preferably R$_7$ is a group which is metabolized in vivo to leave an acidic function on the flavonoid nucleus for R$_7$. Accordingly, —CHO, —COOR$_{10}$, P(O)(OR$_{10}$R$_{11}$), —CH$_2$CH—COOR$_{10}$, and —CONR$_{10}$R$_{11}$ are preferred for R$_7$.

In another of its preferred embodiments, the present invention provides compounds of the following formula (II)

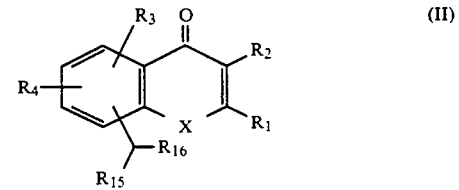

wherein:
X is NH, O, Se, or S(O)$_n$ where n is 0, 1 or 2;
R$_1$ is methyl, phenyl, substituted phenyl, biphenyl, or trifluoromethyl;
R$_2$ is hydrogen or OH, or
R$_1$ and R$_2$, together, form a naphthalene system fused to the hetero—ring of the flavonoid nucleus;
R$_3$ and R$_4$ are hydrogen, alkyl, C$_{1-6}$ alkoxy hydroxy, halogen, or R$_3$ and R$_4$ together form a benzene system fused to the benzene ring of the flavonoid nucleus;
R$_{15}$ is hydrogen when R$_{16}$ is a carboxylic radical, a carbamyl radical, a mercapto radical, a carboxymethylthio radical, an aminoether radical, a phosphonic group, a substituted hydrazino, an amino group, a substituted amino group, a lower alkyl group, —CONH—R$_{17}$, —CS—NH—R$_{18}$ (where R$_{17}$ and R$_{18}$ are C$_{1-6}$ alkyl), oximino, or a substituted thiazolyl, NR$_{19}$R$_{20}$, (wherein R$_{19}$ and R$_{20}$ are hydrogen, an aromatic group, a substituted aromatic group, an hydroxyalkyl group, a carboxymethylene group, or R$_{19}$ and R$_{20}$ together form an imidazole ring or N-methyl-piperazinyl);

when
R$_{15}$ is R—CH=, R$_1$ is hydrogen, phenyl, 3-pyridyl, 4-pyridyl, and R$_{16}$ is COOH.

R$_{15}$ and R$_{16}$ can also be a tetronic moiety or a substituted tetronic moiety.

When R$_{16}$ is =O, R$_{15}$ is preferably —COOH, —CH=CH—COOH, —CH$_3$, —CH$_2$—Br, —CH=CH—AR, with AR being H, phenyl, 3-pyridyl or 4-pyridyl; or R$_{15}$ and R$_{16}$ can together form a tetronic moiety, a substituted thiazolyl moiety, indolizinyl, imidazo [2,1-b] thiazolyl, imidazo [1,2-a] pyridino, a tetrahydropyran which is substituted or a cyclic lactonic moiety.

When R$_4$ and R$_{15}$ together form a benzene system, R$_{16}$ is preferably COOH, or CH$_2$COOH.

When R$_1$ and R$_2$ together form a naphthalene system, preferably R$_{15}$ is hydrogen and R$_{16}$ is COOH.

When R$_3$ and R$_4$ form a benzene system, preferably R$_{15}$ is hydrogen and R$_{16}$ is COOH.

When R$_{15}$ is hydroxyl, R$_{16}$ is preferably COOH or —CH$_2$CH$_2$COOH.

When R$_{15}$ is =O, R$_{16}$ is preferably COOH, or CH$_2$CH$_2$COOH, —CH=CH—COOH.

These compounds and their derivatives are particularily useful as antitumor agents, notably as antipancreatic cancer agents.

The compounds of formula (II) can be prepared in accordance with one of the methods of preparation generally outlined below which provides these compounds in good yields.

In a first process, a compound of (III)

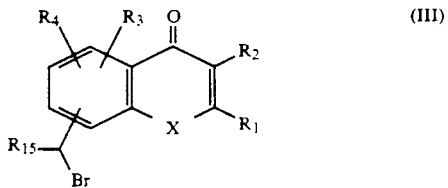

is reacted either with (1) alkaline nitrile component followed by hydrolysis, or (2) with an amine (NR$_{19}$R$_{20}$), or (3) with triethylphosphite followed by hydrolysis, or (4) with a compound of formula R$_{32}$—SH, or R$_{32}$—OH, wherein R$_{32}$ can be —CH$_2$COOEt or —CH$_2$CH$_2$—N(C$_2$H$_5$)$_2$.

In another process to obtain the compounds of formula (II), the compound of formula (III) is reacted either with (1) potassium acetate followed by hydrolysis, oxidation, bromination and condensation with thiourea, thioacetamide, thiobenzamide, 2-amino thiazole, 2-methylpyridine, 2-aminothiazole, or ethoxycarbonyl acetamide.

Compounds of formula (II) can also be obtained by reacting appropriate compounds of formula (II) wherein R$_{15}$ is hydrogen and R$_{16}$ is COOH with an alpha halogenated ester followed by cyclization.

Compounds of formula (II) can also be obtained by reacting appropriate compounds of formula (III) with hexamethylene tetramine and condensation of the carbonylated compound obtained with thiosemicarbazide, hydrazinoimidazole, hydroxylamine, or malonic acid.

Compounds of formula (II) can also be obtained by reacting appropriate compounds of formula (II) wherein R$_{15}$ is hydrogen and R$_{16}$ is COOH with bromine followed by potassium acetate with subsequent hydrolysis and then oxidation.

Compounds of formula (II) can also be obtained from appropriate compounds of formula (II) wherein R$_{15}$ is methyl and R$_{16}$ is COO(C$_2$H$_5$) by reaction with methyl iodide followed by hydrolysis.

Compounds of formula (II) can also be obtained by reacting compounds of formula (II) wherein R$_{15}$ is hydrogen and R$_{16}$ is CN or COOH with H$_2$S or ammonia in the presence of carbonyldiimidazole.

The compounds of formula (II) have been found to surprisingly possess antitumor activity. In particular, the compounds of the invention have been discovered to possess in vitro activity against a variety of tumors in accordance with the following method.

The compounds being tested are placed on a paper disk which is set in the middle of an agar-agar base in which a culture of the selected tumor has been placed. The activity is measured by examining the inhibition of growth of the tumor being cultured. The growth is measured as a function of units (1 unit=25 microns) which are inhibited. These units represent the surface of the growth of the tumor culture. A product is considered to represent a notable level of activity if the number of zones which are inhibited is superior to 250. The tumors used in these tests were adinocarcinomic pancreatic PO3 and colon CO8.

In the tests run by the inventors, in the inhibition of tumor PO3 the compounds of formula 19, 58 and 70 at an application of 1000 micrograms per disk an inhibition value of from 900, 350 and 400, respectively. In the case of tumor CO8, the compounds of formula 31, 19 and 70 administered at 1000 micrograms per disk displayed an inhibition value of 500, 450 and 500, respectively.

Additionally, the compounds of the present invention demonstrated in animal studies, a surprising threshold level, i.e. a relationship between activity and toxicity which provides a therapeutic margin superior to a reference compound, in particular flavone-8-acetic acid. For example, flavone-8-acetic administered at 400 mg/kg, to a group of 10 mice, provided a mortality rate of 10 mice out of the 10 mice tested after 20 days. The compound of the present invention provided by formula 31 provided only 6 deaths out of 10 at an administration level of 400 mg/kg after 20 days. The compound of formula 29 provided 1 death out of 10 at an administration rate of 400 mg/kg after 20 days. And the compound of formula 58 resulted in no deaths of the group of 10 mice at an administration level of 400 mg/kg after 20 days.

In another of its embodiments, the present invention provides compounds of the formula (IV)

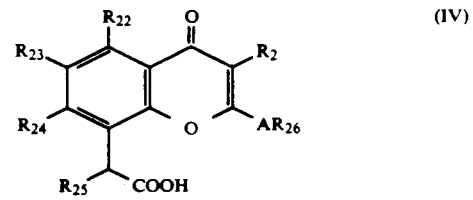

wherein:
AR$_{26}$ is phenyl, substituted phenyl, biphenylyl, pyridyl, or trifluoromethyl;
R$_2$ is hydrogen, hydroxyl, or C$_{1-3}$ alkoxy;
R$_{22}$ is hydrogen, hydroxyl, or C$_{1-6}$ alkoxy;
R$_{23}$ is hydrogen, or fluoro;
R$_{24}$ is hydrogen, or hydroxy;
R$_{25}$ is hydrogen, 2-methylpyridyl, benzylidene, 4-methylenepyridyl, or methylene; or R₂₂ and R₂₃ together form a benzene ring fused to the flavonoid nucleus;

R₂₃ and R₂₄ form a benzene ring fused to the flavonoid nucleus; or

R₂₅ and R₂₄ form a benzene ring fused to the flavonoid nucleus.

These compounds possess an immunomodulating activity and in particular they stimulate the formation of interferon and of killer cells.

The compounds of (IV) can be obtained by the hydrolysis of the nitriles of formula (V):

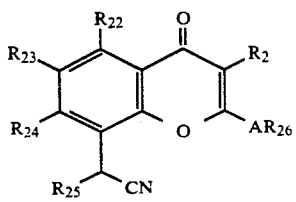

wherein $AR_{26}$, $R_2$, $R_{22}$, $R_{23}$, $R_{24}$ and $R_{25}$ are as defined above. The nitriles of formula (V) are obtained by the reaction of an alkali cyano compound with a compound of formula (VI):

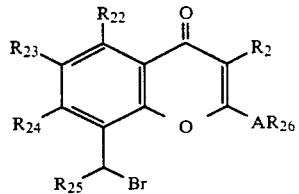

wherein $AR_{26}$, $R_2$, $R_{22}$, $R_{23}$, $R_{24}$ and $R_{25}$ are as defined above.

With compounds of formula (IV) when $R_{25}$ is methylene or arylidene, the compounds are obtained by the reaction of compounds of formula (IV) wherein $R_{25}$ is hydrogen, with N,N,N,N—tetramethyldiaminomethane or with an aromatic aldehyde or an heteroaromatic aldehyde.

The compounds of formula (IV) have been discovered to surprisingly possess immunomodulating properties. The inventors have now discovered that the compounds of formula (IV) possessed a surprisingly high activity with the immune system and that in particular they stimulated the activity of killer cells and induce the formation of interferon (INF).

STIMULATION OF THE ACTIVITY OF KILLER CELLS

The determination of the activity of killer cells was made in accordance with the following. Mice BALB/C were treated intravenously, either with 0.25 ml of HBSS or with 200 mg/kg of a compound of formula (IV). Twenty four hours after administration of the compound, the spleens of the animals were reduced to a state of suspension. Debris and cellular wastes are eliminated by sedimentation and the red corpuscles are lysed with distilled water. The cellular suspension obtained was then filtered over sterile gauze and washed twice with HBSS.

Different quantities of splenic cells are incubated with $1 \times 10^4$ tumored cells of the type YAC-1 stained with chromium 51. The length of incubation was 4 hours at 37° C. in a RPMI 1640-type medium supplemented with 5% of FBS, pencillin (100 U/ml) streptomycin (100 μg/ml), L-glutamine (20 mM), sodium pyruvate (1 mM), and nonessential amino acids (0.1 mM) in a buffered medium. The floating bodies are removed and a count effectuated.

The results are expressed in lytic units ($UL_{10}$): where $UL_{10}$ is the quantity necessary to effectuate lysis of $1 \times 10^4$ target cells. For example, it was discovered that the compound of formula 19, provided 80 UL. The compound of formula 25 provided 60 UL. The compound of formula 42 provided 110 UL. And the control animals treated with HBSS demonstrated no activity measurable in terms of lytic units (UL).

INTERFERON INDUCTION

Mice BALB/C received intravenously, either 0.25 ml of HBSS or 200 mg/kg of one compound of formula (IV). Interferon activity was determined by utilizing the method of viral vesicular stomatitis. A unit of IFN is the quantity of IFN in 1 ml of sample need to reduce the viral lysis by 50%. For example, it was discovered that with the compound of formulae 19, 25 and 67, an activity of 1000 units of IFN was obtained, whereas the control animals treated with HBSS demonstrated no induction in the production of IFN.

Other features of the invention will become apparent in the course of the following descriptions of exemplary embodiments which are given for illustration of the invention and are not intended to be limiting thereof.

EXAMPLES

Example 1 a) Oxo-1 Phenyl- 3-1H-Naphto (2,1-b) Pyran-5-Acetonitrile $C_{21}H_{13}NO_2$  MW=311,344

A mixture of 8.2 g (0.0224 mole) of bromomethyl-5-phenyl-3-[1H]-naphto(2.1-b)pyranol-1, of 4.9 g (0.031 mole) of tetraethylammonium cyanide in 250 ml of dichloroethane is stirred for 18 hours at room temperature. Evaporation is then carried out in a vacuum, the mixture is solidified using water, and the solid thus formed is filtered and dried. Weight obtained: 6.9 g (Yield: 98%); $PF_k = 260°$ C.; IR: $Vc=o=7039$ cm$^{-1}$, $Vc=N$; 2160 and 2220 cm$^{-1}$.

b) Oxo- 1-Phenyl-3-(1H)-Naphto (2.1-b) Pyran-5-Acetic Acid $C_{24}H_{14}O_4$   MW = 330.34   [Formula 1]

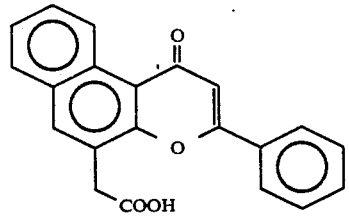

A mixture of 6.9 g (0.022 mole) of oxo-1-phenyl-3-[1H]-naphto(2.1-b)pyran-5-aceto-nitrile, 50 ml of acetic acid, 50 ml of water and 50 ml of H₂SO₄ in concentrated form is heated by reflux. The medium is then poured into water and frozen; the solid thus formed is centrifuged, dried, recrystallized in acetic acid. Weight obtained: 2.1 g (Yield: 28%); $PF_G = 291°-293°$ C.; IR: $V_{C=O}$ (acid) = 1700 cm$^{-1}$, $V_{C=O}$ (pyrone) = 1638 cm$^{-1}$; NMR (DMSO)δ in ppm in relation to TMS: 2H at 4.03 (s), 1H at 7.1 (s), 9H at 7.3 to 8.3 (n), 1H at 12.5 (exchangeable).

| Elemental analysis | C % | H % | O % |
|---|---|---|---|
| calculated: | 76.35 | 4.27 | 19.37 |
| found: | 73.85 | 4.01 | |

Using the same technique the following compounds are prepared:

Oxo-4-Phenyl-2-4H-Naphto (2.3-b) Pyran-1-Acetic acid $C_{24}H_{14}O_4$    MW = 330.34    [Formula 2]

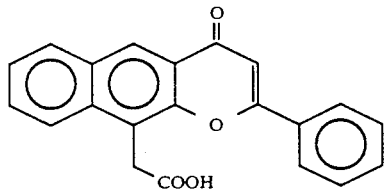

$PF_G = 276°-288°$ C.; IR: $V_{C=O}$ (acid) = 1720 cm$^{-1}$, $V_{C=O}$ (pyrone) = 7610 cm$^{-1}$; NMR (DMSO)δ in ppm in relation to TMS: 2H at 4.4 (s), 1H at 6.97 (s), 9H at 7.2 to 8.5 (m), 1H at 8.62 (s), 1H at 12.5 (exchangeable).

| Elemental analysis | C % | H % | O % |
|---|---|---|---|
| calculated: | 76.39 | 4.27 | 19.38 |
| found: | 79.89 | 4.39 | |

Oxo-4-Phenyl-2-4H-Naphto (1.2-b) Pyran-10-Acetic Acid $C_{21}H_{14}O_4$    MW 330.34    [Formula 3]

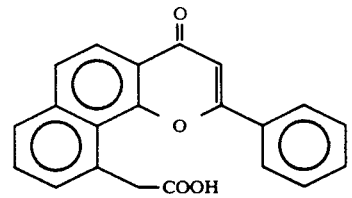

$PF_G = 259°-261°$ C.; IR: $V_{C=O}$ (acid) = 1710 cm$^{-1}$, $V_{C=O}$ (pyrone) = 7630 cm$^{-1}$; NMR (DMSO)δ in ppm in relation to TMS: 2H at 4.45(s), 1 H at 6.9 (s), 10H at 7.3 to 8.3 (m), 1H at 12.2 (exchangeable).

| Elemental analysis | C % | H % | O % |
|---|---|---|---|
| calculated: | 76.39 | 4.27 | 19.38 |
| found: | 76.24 | 4.07 | |

Methoxy-3-Oxo-4-Phenyl-2H-(1)-Benzopyran-8-Acetic Acid $C_{18}H_{14}O_5$    MW = 310.292    [Formula 4]

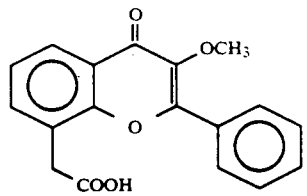

$PF_G = 187°-192°$ C.; IR $V_{C=O}$ (acid) = 1720 cm$^{-1}$, $V_{C=O}$ (pyrone) = 1610 cm$^{-1}$; NMR (DMSO)δ in ppm in relation to TMS: 3H at 3.8 (s), 2H at 4 (s), 8H at 7.4 to 8.3 (m), 1H 11.9 (exchangeable).

| Elemental analysis | C % | H % | O % |
|---|---|---|---|
| calculated: | 69.67 | 4.55 | 23.78 |
| found: | 69.90 | 4.55 | |

Methoxy-5-Oxo-4-Phenyl-2H-4H-(1)-Benzopyran-8-Acetic Acid $C_{18}H_{14}O_5$    MW = 310.292    [Formula 5]

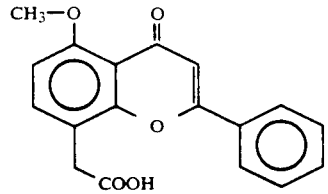

$PF_G = 245°-248°$ C.; IR $v_{C=O}$ (acid) = 1720 cm$^{-1}$, $V_{C=O}$ (pyrone) = 1640 cm$^{-1}$; NMR (DMSO)δ in ppm in relation to TMS: 5H at 4 (s), 1H at 7.2 (s), 7H at 7.7 to 8.7 (m), 1H at 12.2 (exchangeable).

| Elemental analysis | C % | H % | O % |
|---|---|---|---|
| calculated: | 69.67 | 4.55 | 29.78 |
| found: | 69.50 | 4.57 | |

Methoxy-2-Phenyl)-2-Oxo-4-4H-(1) Benzopyran-8-Acetic Acid $C_{18}H_{14}O_5$    MW = 310.292    [Formula 6]

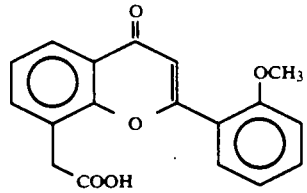

$PF_G = 203°-205°$ C.; IR $v_{C=O}$ (acid) = 1730 cm$^{-1}$; $V_{C=O}$ (pyrone) = 1610 cm$^{-1}$; NMR (DMSO)δ in ppm in relation to TMS: 5H at 4 (s), 1H at 7 (s), 7H at 7.1 to 8.1 (m), 1H at 12.8 (exchangeable).

| Elemental analysis | C % | H % | O % |
| --- | --- | --- | --- |
| calculated: | 69.67 | 4.55 | 25.78 |
| found: | 69.72 | 4.39 | |

Hydroxy-3-Oxo-4-Phenyl-2-4H-(1)-Benzopyran-8-Acetic Acid $C_{17}H_{12}O_3$    MW = 296.266    [Formula 7]

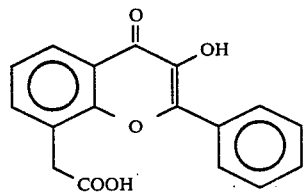

$PF_G = 221°-223°$ C.; IR vc=o (acid)=1700 cm$^{-1}$; Vc=0 (pyrone)=1610 cm$^{-1}$; NMR (DMSO)δ in ppm in relation to the TMS: 2H at 4 (s), 8H) at 7.3–8.4 (m), 1H at 9.6 (exchangeable), 1H at 12.3 (exchangeable).

| Elemental analysis | C % | H % | O % |
| --- | --- | --- | --- |
| calculated: | 68.92 | 4.08 | 27.00 |
| found: | 68.86 | 4.01 | |

Hydroxy-5-Oxo-4-Phenyl-2-4H-(1)-Benzopyran-8-Acetic Acid $C_{17}H_{12}O_5$    MW = 296.266    [Formula 8]

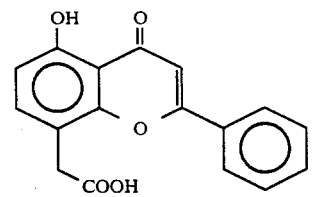

$PF_G = 233°-238°$ C.; IR vc=o (acid)=1700 cm$^{-1}$; Vc=0 (pyrone)=1680 cm$^{-1}$; NMR (DMSO)δ in ppm in relation to TMS: 2H at 3.8 (s), 1H at 6.8 (d), 1H at 7.1 (s), 6H at 7.4 to 8.2 (m), 1H at 42.4 (exchangeable).

| Elemental analysis | C % | H % | O % |
| --- | --- | --- | --- |
| calculated: | 68.92 | 4.08 | 27.00 |
| found: | 68.85 | 4.22 | |

Hydroxy-7-Oxo-4-Phenyl-2-4H-(1)-Benzopyran-8-Acetic Acid $C_{17}H_{12}O_5$    MW = 296.266    [Formula 9]

-continued

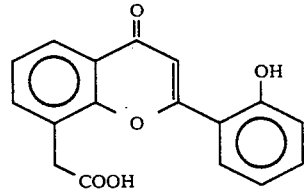

$PF_G = 227°-238°$ C.; IR vc=o (acid)=1700 cm$^{-1}$; Vc=0 (pyrone)=1630 cm$^{-1}$; NMR (DMSO)δ in ppm in relation to TMS: 2H at 3.8 (s), 8H at 6.8 to 8.2 (m), 2H at 10.8 to 11.1 (exchangeable).

| Elemental analysis | C % | H % | O % |
| --- | --- | --- | --- |
| calculated: | 68.92 | 4.08 | 27.00 |
| found: | 68.92 | 4.00 | |

Hydroxy-2-Phenyl)-2-Oxo-4-4H-(1)-Benzopyran-8-Acetic Acid $C_{17}H_{12}O_3$    MW = 296.266    [Formula 10]

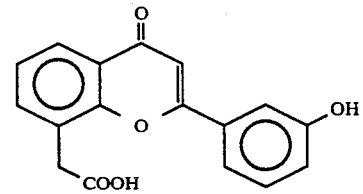

$PF_G = 288°-292°$ C.; IR Vc=o (acid)=1700 cm$^{-1}$; Vc=0 (pyrone)=1640 cm$^{-1}$; NMR (DMSO)δ in ppm in relation to TMS: 2H at 4 (s), 1H at 7 (S), 1H at 7 (s), 7H at 7.2 to 8.2 (m), 2H at 10.8 to 12.9 (exchangeable).

| Elemental analysis | C % | H % | O % |
| --- | --- | --- | --- |
| calculated: | 68.92 | 4.08 | 27.00 |
| found: | 68.75 | 3.88 | |

Hydroxy-3-Phenyl)-2-Oxo-4-4H-(1)-Benzopyran-8-Acetic Acid $C_{17}H_{12}O_5$    MW = 296.266    [Formula 11]

$PF_G = 259°-288°$ C.; IR vc=o (acid)=1720 cm$^{-1}$; Vc=0 (pyrone)=1630 cm$^{-1}$; NMR (DMSO)δ in ppm in relation to TMS: 2H at 4.1 (s), 1H at 7 (s), 7H at 7.1 to 8.2 (m), 1H to 10 at 10 (exchangeable), 1H at 12.8 (exchangeable).

| Elemental analysis | C % | H % | O % |
| --- | --- | --- | --- |
| calculated: | 68.92 | 4.08 | 27.00 |

| -continued | | | |
|---|---|---|---|
| Elemental analysis | C % | H % | O % |
| found: | 68.91 | 4.21 | |

Hydroxy-4-Phenyl)-2-Oxo-4-4H-(1)-Benzopyran-8-Acetic Acid $C_{17}H_{12}O_5$    MW = 296.266    [Formula 12]

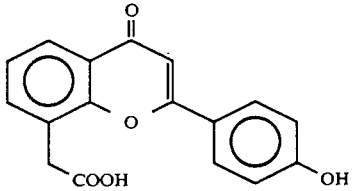

$PF_G$=261°-268° C.; IR Vc=o (acid)=1690 cm$^{-1}$; Vc=0 (pyrone)=1620 cm$^{-1}$; NMR (DMSO)δ in ppm in relation to TMS: 2H at 3.8 (s), 8H at 6.7 to 8 (m), 1H at 10.3 (exchangeable), 1H at 12.2 (exchangeable).

| Elemental analysis | C % | H % | O % |
|---|---|---|---|
| calculated: | 68.92 | 4.08 | 27.00 |
| found: | 68.61 | 4.20 | |

Chlorohydrate of (Diethylaminoethoxy-3-Phenyl)-2-Oxo-4-4H-Benzopyran-8-Acetic Acid $C_{23}H_{26}ClNO_3$    MW = 431.903    [Formula 13]

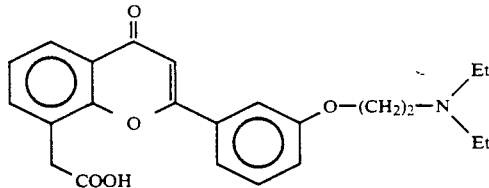

$PF_G$=176°-179° C.; IR Vc=o (acid)=1720 cm$^{-1}$, Vc=0 (pyrone)=1640 cm$^{-1}$; NMR (DMSO)δ in ppm in relation to TMS; 3H at 1.4 (t), 11H at 3 to 4.6 (m, of which 1H is interchangeable), 1H at 7.1 (s), 6H at 7.2 to 8.1 (m), 1H at 13.2 (interchangeable).

| Elemental analysis | C % | H % | Cl % | N % | O % |
|---|---|---|---|---|---|
| calculated: | 63.96 | 6.07 | 8.21 | 3.24 | 18.32 |
| found: | 63.69 | 5.88 | 8.09 | 3.01 | |

(Phenoxy-2-Phenyl-2-Oxo-4-4H-(1)-Benzopyran-8-Acetic Acid $C_{23}H_{16}O_3$    MW = 372.38    [Formula 14]

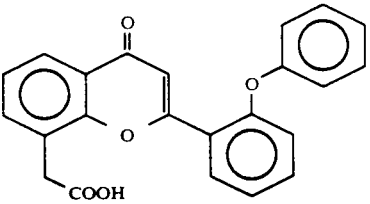

$PF_G$=218°-220° C.; IR Vc=o (acid)=1680 cm$^{-1}$, Vc=0 (pyrone)=1640 cm$^{-1}$; NMR (DMSO)δ in ppm in relation to TMS; 2H at 3.8 (s), 13H at 6.8 to 8 (m), 1H at 12.6 (interchangeable).

| Elemental analysis | C % | H % | O % |
|---|---|---|---|
| calculated: | 74.19 | 4.33 | 21.48 |
| found: | 73.88 | 4.56 | |

Fluoro-6-Oxo-4-Phenyl-2-4H-(1)-Benzopyran-8-Acetic Acid $C_{17}H_{11}FO_4$    MW = 298.26    [Formula 15]

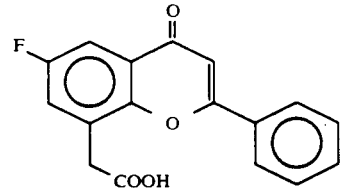

$PF_G$=225°-239° C.; IR Vc=o (acid)=1720 cm$^{-1}$, Vc=0 (pyrone)=1640 cm$^{-1}$; NMR (DMSO)δ in ppm in relation to TMS; 3H at 3 to 4 (m, of which 1H is interchangeable), 1H at 7 (s), 7H at 7, 1H at 8.4 (m).

| Elemental analysis | C % | H % | F % | O % |
|---|---|---|---|---|
| calculated: | 68.49 | 3.72 | 6.37 | 21.46 |
| found: | 68.42 | 3.92 | 6.28 | |

Fluoro-2-Phenyl)-2-Oxo-4-4H-(1)-Benzopyran-8-Acetic Acid $C_{17}H_{11}FO_4$    MW = 298.26    [Formula 16]

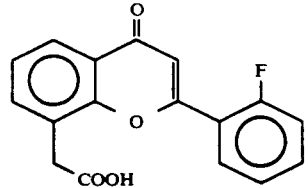

$PF_G$=193°-199° C.; IR Vc=o (acid)=1720 cm$^{-1}$, Vc=0 (pyrone)=1610 cm$^{-1}$; NMR (DMSO)δ in ppm in relation to TMS; 2H at 4 (s), 1H at 6.7 (s), 7H at 7.2 to 8.4 (m), 1H at 12.5 (interchangeable).

| Elemental analysis | C % | H % | F % | O % |
|---|---|---|---|---|
| calculated: | 68.49 | 3.72 | 6.37 | 21.46 |

| Elemental analysis | C % | H % | F % | O % |
|---|---|---|---|---|
| found: | 68.42 | 3.92 | 6.28 | |

Fluoro-4-Phenyl)-2-Oxo-4H-(1)-Benzopyran-8-Acetic Acid $C_{17}H_{11}FO_4$    MW = 298.26    [Formula 17]

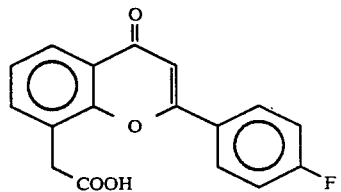

$PF_G$=215°-217° C.; IR Vc=o (acid)=1720 cm$^{-1}$, Vc=0 (pyrone)=1640 cm$^{-1}$; NMR (CF$_3$COOD)δ in ppm in relation to TMS; 2H at 4 (s), 8H at 7 to 9 (m).

| Elemental analysis | C % | H % | F % | O % |
|---|---|---|---|---|
| calculated: | 67.49 | 3.72 | 6.37 | 24.46 |
| found: | 68.54 | 3.80 | 6.33 | |

Fluoro-3-Phenyl)-2-Oxo-4-4H-(1)-Benzopyran-8-Acetic Acid $C_{17}H_{11}FO_4$    MW = 297.26    [Formula 18]

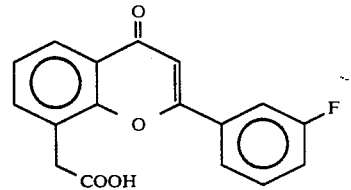

$PF_G$=201°-203° C.; IR Vc=o (acid)=1700 cm$^{-1}$, Vc=0 (pyrone)=1640 cm$^{-1}$; NMR (DMSO)δ in ppm in relation to TMS; 2H at 4 (s), 1H at 7.1 (s), 7H at 7.2 to 8 (m), 1H at 12.6 (interchangeable).

| Elemental analysis | C % | H % | F % | O % |
|---|---|---|---|---|
| calculated: | 68.49 | 3.72 | 6.37 | 21.46 |
| found: | 68.20 | 3.69 | 6.28 | |

Phenyl-4-Phenyl)2-Oxo-4-4H-(1)-Benzopyran-8-Acetic Acid $C_{23}H_{16}O_4$    MW = 356.36    [Formula 19]

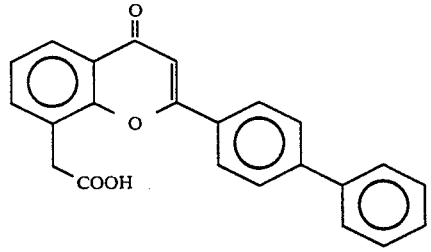

$PF_G$=229°-231° C.; IR Vc=o (acid)=1710 cm$^{-1}$, Vc=0 (pyrone)=1620 cm$^{-1}$; NMR (DMSO)δ in ppm in relation to TMS; 2H at 4 (s), 1H at 7 (s), 12H at 7.2 to 8.4 (m), 1H at 12.6 (interchangeable).

| Elemental analysis | C % | H % | O % |
|---|---|---|---|
| calculated: | 77.51 | 4.53 | 17.96 |
| found: | 77.42 | 4.41 | |

(Chloro-4-Phenyl)-2-Oxo-4-4H-(1)-Benzopyran-8-Acetic Acid $C_{17}H_{11}ClO_4$    MW = 314.71    [Formula 20]

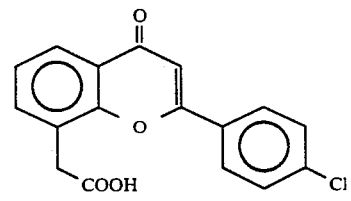

$PF_G$=238°-242° C.; IR Vc=o (acid)=1720 cm$^{-1}$, Vc=0 (pyrone)=1620 cm$^{-1}$; NMR (DMSO)δ in ppm in relation to TMS; 2H at 4 (s), 1H at 7 (s), 7H at 7.2 to 8.2 (m), 1H at 12.5 (interchangeable).

| Elemental analysis | C % | H % | Cl % | O % |
|---|---|---|---|---|
| calculated: | 64.87 | 3.52 | 11.27 | 20.34 |
| found: | 64.83 | 3.37 | 11.55 | |

(Carboxy-4-Phenyl)-2-Oxo-4-4H-(1)-Benzopyran-8-Acetic Acid $C_{18}H_{12}O_6$    MW = 324.27    [Formula 21]

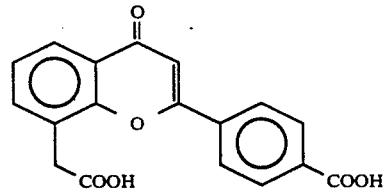

$PF_G$=312°-314° C.; IR Vc=o (acid)=170-1720 cm$^{-1}$, Vc=0 (pyrone)=1640 cm$^{-1}$.

| Elemental analysis | C % | H % | O % |
|---|---|---|---|
| calculated: | 66.67 | 3.73 | 29.69 |

-continued

| Elemental analysis | C % | H % | O % |
|---|---|---|---|
| found: | 66.76 | 3.73 | |

Fluoro-2-Phenyl)-4-Phenyl)-2-Oxo-4-4H-(1)Benzopyran-8-Acetic Acid $C_{23}H_{15}FO_4$   MW = 374.35   [Formula 22]

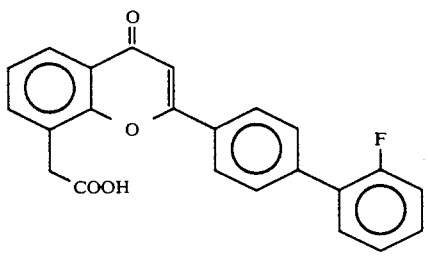

$PF_G=226°-228°$ C.; IR $V_{c=o}$ (acid)=1720 cm$^{-1}$, $V_{c=0}$ (pyrone)=1630 cm$^{-1}$; NMR (DMSO)δ in ppm in relation to TMS; 2H at 4 (s), 12H at 7 to 8.4 (m), 1H to 12.8 (interchangeable).

| Elemental analysis | C % | H % | F % | O % |
|---|---|---|---|---|
| calculated: | 73.79 | 4.04 | 5.08 | 17.10 |
| found: | 73.80 | 4.14 | 4.87 | |

(Nitro-2-Phenyl)-2-Oxo-4-4H-(1)-Benzopyran-8-Acetic Acid $C_{17}H_{11}NO_4$   MW = 325.28   [Formula 23]

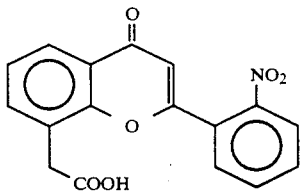

$PF_G=180°-182°$ C.; IR $V_{c=o}$ (acid)=1700 cm$^{-1}$, $V_{c=0}$ (pyrone)=1640 cm$^{-1}$; NMR (DMSO)δ in ppm in relation to TMS; 2H at 4 (s), 1H at 6.8 (s), 7H at 7.3 to 8.3 (m), 1H at 12.8 (interchangeable).

| Elemental analysis | C % | H % | N % | O % |
|---|---|---|---|---|
| calculated: | 62.77 | 3.41 | 4.31 | 29.51 |
| found: | 62.82 | 3.47 | 4.20 | |

(Nitro-3-Phenyl)-2-Oxo-4-4H-(1)-Benzopyran-8-Acetic Acid $C_{17}H_{11}NO_6$   MW = 325.28   [Formula 24]

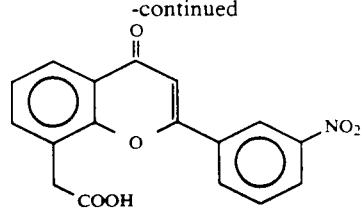

$PF_G=203°-208°$ C.; IR $V_{c=o}$ (acid)=1720 cm$^{-1}$, $V_{c=0}$ (pyrone)=1630 cm$^{-1}$; NMR (DMSO)δ in ppm in relation to TMS; 2H at 4 (s), 1H at 7.3 (s), 7H at 7.4 to 9 (m), 1H at 12.5 (interchangeable).

| Elemental analysis | C % | H % | N % | O % |
|---|---|---|---|---|
| calculated: | 62.77 | 3.41 | 4.31 | 29.51 |
| found: | 62.49 | 3.40 | 4.31 | |

(Nitro-4-Phenyl)-2-Oxo-4-4H-(1)-Benzopyran-8-Acetic Acid $C_{17}H_{11}NO_6$   MW = 325.28   [Formula 25]

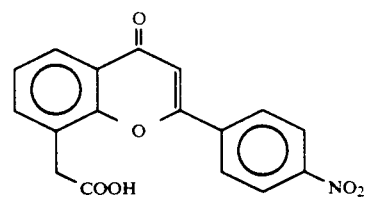

$PF_G=242°-244°$ C.; IR $V_{c=o}$ (acid)=1720 cm$^{-1}$, $V_{c=0}$ (pyrone)=1620 cm$^{-1}$; NMR (DMSO)δ in ppm in relation to TMS; 2H at 4 (s), 1H at 7 (s), 7H at 7.2 to 8.3 (m), 1H at 12.5 (interchangeable).

| Elemental analysis | C % | H % | N % | O % |
|---|---|---|---|---|
| calculated: | 62.77 | 3.41 | 4.31 | 29.51 |
| found: | 62.92 | 3.38 | 4.28 | |

(Amino-3-Phenyl)-2-oxo-4-4H-(1)-Benzopyran-8-Acetic Acid $C_{17}H_{13}NO_4$   MW = 295.28   [Formula 26]

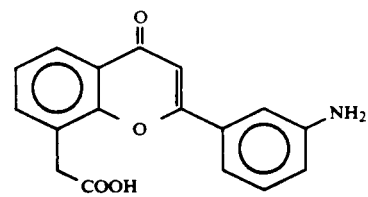

$PF_G=227°-139°$ C.; IR $V_{c=o}$ (acid)=1720 cm$^{-1}$, $V_{c=0}$ (pyrone)=1630 cm$^{-1}$; NMR (DMSO)δ in ppm in relation to TMS; 2H at 4 (s), 9H at 6.8 to 8 (m), 1H at 12.6 (interchangeable).

| Elemental analysis | C % | H % | N % | O % |
|---|---|---|---|---|
| calculated: | 69.14 | 4.44 | 4.74 | 21.67 |
| found: | 69.20 | 4.70 | 4.94 | |

(Amino-4-Phenyl)-2-oxo-4-4H-(1)-Benzopyran-8-Acetic Acid

C$_{17}$H$_{13}$NO$_4$    MW = 295.28    [Formula 27]

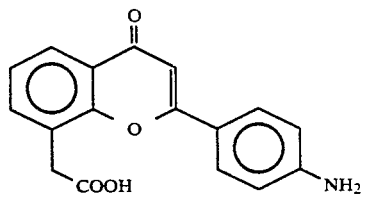

PF$_G$=189° C.; IR Vc=o (acid)=1700 cm$^{-1}$, Vc=0 (pyrone)=1620 cm$^{-1}$;

| Elemental analysis | C % | H % | N % | O % |
|---|---|---|---|---|
| calculated: | 69.14 | 4.44 | 4.74 | 21.67 |
| found: | 69.00 | 4.48 | 4.66 | |

Oxo-4-Phenyl-2-4H-(1)-Benzopyran-5-Acetic Acid

C$_{17}$H$_{12}$O$_4$    MW = 280.28    [Formula 28]

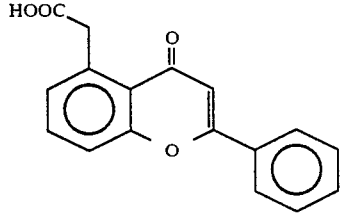

PF$_G$=240°-242° C.; IR Vc=o (acid)=1740 cm$^{-1}$, Vc=0 (pyrone)=1640 cm$^{-1}$; NMR (DMSO)δ in ppm in relation to TMS; 2H at 4 (s), 1H at 7 (s), 8H at 7.2 to 8.4 (m), 1H at 12.6 (interchangeable).

| Elemental analysis | C % | H % | O % |
|---|---|---|---|
| calculated: | 72.85 | 4.32 | 22.83 |
| found: | 73.00 | 4.16 | |

Oxo-4-Phenyl-2-4H-(1)-Benzopyran-7-Acetic Acid

C$_{17}$H$_{12}$O$_4$    MW = 280.28    [Formula 29]

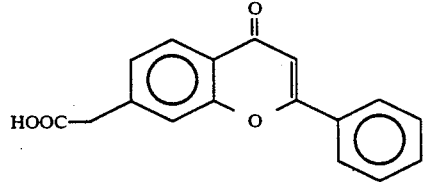

PF$_G$=237°-239° C.; IR Vc=o (acid)=1740 cm$^{-1}$, Vc=0 (pyrone)=1620 cm$^{-1}$; NMR (DMSO)δ in ppm in relation to TMS; 2H at 3.7 (s), 1H at 6.8 (s), 7H at 7.2 to 8 (m), 1H at 12.5 (interchangeable).

| Elemental analysis | C % | H % | O % |
|---|---|---|---|
| calculated: | 72.85 | 4.32 | 22.83 |

| Elemental analysis | C % | H % | O % |
|---|---|---|---|
| found: | 72.73 | 4.33 | |

Trifluoromethyl-2-Oxo-4-4H-(1)-Benzopyran-8-Acetic Acid

C$_{12}$H$_7$F$_3$O$_4$    MW = 272.17    [Formula 30]

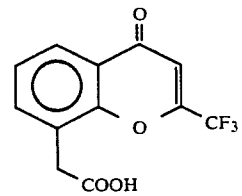

PF$_G$=141°-143° C.; IR Vc=o (acid)=1700 cm$^{-1}$, Vc=0 (pyrone)=1650 cm$^{-1}$.

| Elemental analysis | C % | H % | F % | O % |
|---|---|---|---|---|
| calculated: | 52.95 | 2.59 | 20.94 | 23.52 |
| found: | 52.72 | 2.64 | 20.35 | |

Oxo-4-Phenyl-2-4H-(1)-Benzothiopyran-8-Acetic Acid

C$_{17}$H$_{12}$O$_3$S    MW = 296.34    [Formula 31]

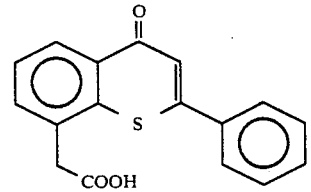

PF$_G$=198°-200° C.; IR Vc=o (acid)=1720 cm$^{-1}$, Vc=0 (pyrone)=1610 cm$^{-1}$; NMR (DMSO)δ in ppm in relation to TMS; 2H at 4 (s), 1H at 7.3 (s), 7H at 7.3 to 8.4 (m), 1H at 12.5 (s), 1H at 7.3 (s), 7H at 7.3 to 8.4 (m), 1H at 12.5 (interchangeable).

| Elemental analysis | C % | H % | O % | S % |
|---|---|---|---|---|
| calculated: | 68.40 | 4.08 | 16.20 | 10.82 |
| found: | 69.04 | 4.29 | | 11.04 |

Oxo-4-Phenyl-2-4H-(1)-Benzothiopyran-8-Acetic Acid S,S-Dioxide

C$_{17}$H$_{12}$O$_5$S    MW = 328.34    [Formula 32]

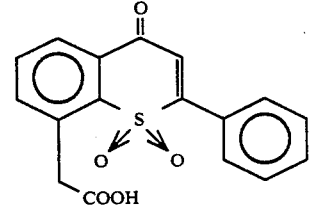

PF$_G$=184°-187° C.; IR Vc=o (acid)=1700 cm$^{-1}$, Vc=0 (pyrone)=1660 cm$^{-1}$; NMR (DMSO)δ in ppm in relation to TMS; 2H at 4 (s), 1H at 7 (s), 7H at 7.2 to 8.2 (m), 1H at 12.6 (interchangeable).

| Elemental analysis | C % | H % | O % | S % |
|---|---|---|---|---|
| calculated: | 62.18 | 3.68 | 24.36 | 9.77 |
| found: | 62.29 | 3.68 |  | 9.65 |

Oxo-4-Phenyl-2-Dihydro-1-4-Quinoline-8-Acetic Acid

C$_{17}$H$_{13}$NO$_3$     MW = 279.29     [Formula 33]

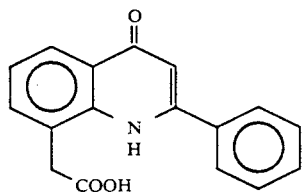

PF$_G$=236°-238° C.; IR Vc=o (acid)=1680 cm$^{-1}$, Vc=0 (pyrone)=1620 cm$^{-1}$; NMR (DMSO)δ in ppm in relation to TMS; 2H at 4 (s), 8H at 7 to 8.3 (m), 1H at 8.5 (interchangeable).

| Elemental analysis | C % | H % | N % | O % |
|---|---|---|---|---|
| calculated: | 73.11 | 4.69 | 5.01 | 17.18 |
| found: | 73.10 | 4.62 | 5.04 |  |

Oxo-4-Phenyl-2-4H (1)-Benzoselenopyran-8-Acetic Acid

C$_{17}$H$_{12}$O$_3$Se     MW = 343.24     [Formula 34]

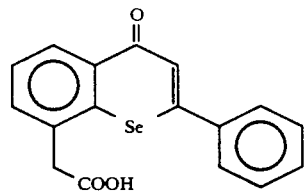

PF$_G$=182°-184° C.; IR Vc=o (acid)=1700 cm$^{-1}$, Vc=0 (pyrone)=1600 cm$^{-1}$; NMR (DMSO)δ in ppm in relation to TMS; 2H at 4 (s), 8H at 7.4 to 8.6 (m), 1H at 12.5 (interchangeable).

| Elemental analysis | C % | H % | O % | Se % |
|---|---|---|---|---|
| calculated: | 59.49 | 3.52 | 13.98 | 23.00 |
| found: | 59.30 | 3.26 |  | 22.91 |

Oxo-7-7H-Benzo(c)Xanthenyl-11-Acetic Acid

C$_{19}$H$_{12}$O$_4$     MW = 304.31     [Formula 35]

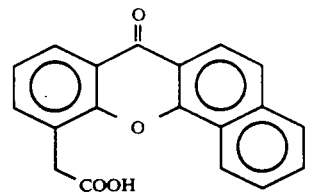

PF$_G$=270°-272° C.; IR Vc=o (acid)=1720 cm$^{-1}$, Vc=0 (pyrone)=1620 cm$^{-1}$; NMR (DMSO)δ in ppm in relation to TMS; 2H at 4 (s), 9H at 7.4 to 9.2 (m), 1H at 12.5 (interchangeable).

| Elemental analysis | C % | H % | O % |
|---|---|---|---|
| calculated: | 74.99 | 3.97 | 21.03 |
| found: | 73.34 | 3.93 |  |

Oxo-4-7-7H-Dibenzo(c,h)Xanthenyl-1-Acetic Acid

C$_{23}$H$_{14}$O$_4$     MW = 354.37     [Formula 36]

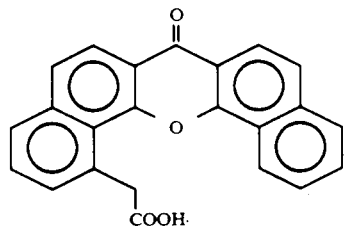

PF$_G$=276°-278° C.; IR Vc=o (acid)=1700 cm$^{-1}$, Vc=0 (pyrone)=1620 cm$^{-1}$; NMR (DMSO)δ in ppm in relation to TMS; 2H at 4 (s), 11H at 7.4 to 8.8 (m), 1H at 12.5 (interchangeable).

| Elemental analysis | C % | H % | O % |
|---|---|---|---|
| calculated: | 77.96 | 3.98 | 18.06 |
| found: | 77.94 | 3.97 |  |

Carboxymethyl-4-Phenyl)-2-4H-(1) Benzopyranone-4

C$_{17}$H$_{12}$O$_4$     MW = 280.17     [Formula 37]

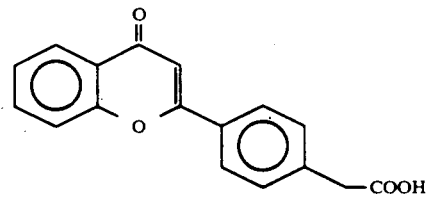

PF$_G$=204° C.; IR Vc=o (acid)=1720 cm$^{-1}$, Vc=0 (pyrone)=1640 cm$^{-1}$.

| Elemental analysis | C % | H % | O % |
|---|---|---|---|
| calculated: | 72.84 | 4.32 | 22.84 |
| found: | 72.08 | 4.33 | |

Carboxymethyl-3-Phenyl)-2-4H-(1) Benzopyranone-4

$C_{17}H_{12}O_4$  MW = 280.27  [Formula 38]

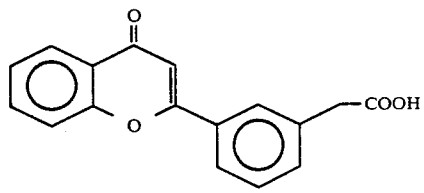

$PF_G = 181°-183°$ C.; IR Vc=o (acid)=1720 cm$^{-1}$, Vc=0 (pyrone)=1620 cm$^{-1}$; NMR (DMSO)δ in ppm in relation to TMS; 2H at 3.8 (s), 1H at 7 (s), 8H at 7.4 to 8.2 (m), 1H at 12.4 (interchangeable).

| Elemental analysis | C % | H % | O % |
|---|---|---|---|
| calculated: | 72.84 | 4.32 | 22.84 |
| found: | 73.08 | 4.41 | |

Carboxymethyl-2-Phenyl)-2-4H-(1) Benzopyranone-4

$C_{17}H_{12}O_4$  MW = 280.27  [Formula 39]

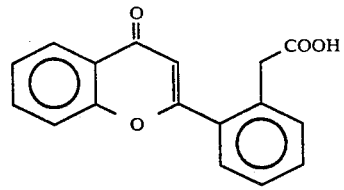

$PF_G = 179°-181°$ C.; IR Vc=o (acid)=1730 cm$^{-1}$, Vc=0 (pyrone)=1630 cm$^{-1}$; NMR (DMSO)δ in ppm in relation to TMS; 2H at 3.9 (s), 1H at 6.6 (s), 8H at 7.2 to 8.2 (m), 1H at 12.4 (interchangeable).

| Elemental analysis | C % | H % | O % |
|---|---|---|---|
| calculated: | 72.84 | 4.32 | 22.84 |
| found: | 73.79 | 4.34 | |

((Oxo-4-Phenyl-2-4H-(1) Benzopyran-8-yl) Methyl)

$C_{20}H_{21}O_5P$  MW = 372.39  [Formula 40]

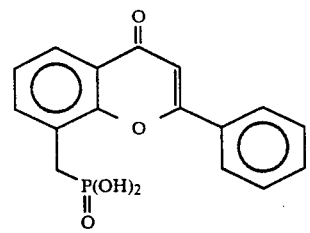

$PF_G = 107°-109°$ C.; IR Vc=0 (pyrone)=1640 cm$^{-1}$; NMR (CDCl$_3$)δ in ppm in relation to TMS; 6H at 1.2 (d), 2H at 3.57 (d), 4H at 3.7 to 4.4 (m), 1H at 6.85 (s), 8H at 7.2 to 8.4 (m).

| Elemental analysis | C % | H % | O % | P % |
|---|---|---|---|---|
| calculated: | 64.51 | 5.69 | 21.48 | 8.32 |
| found: | 64.59 | 5.67 | | 8.17 |

((Oxo-4-Phenyl-2-4H-(1) Benzopyran-8-yl) Methyl) Phosphonic Acid $C_{16}H_{13}O_5$  MW = 316.24  [Formula 41]

$PF_G = 331°-334°$ C.; IR V OH=3400 to 2200 cm$^{-1}$, Vc=0 (pyrone)=1620 cm$^{-1}$; NMR (DMSO)δ in ppm in relation to TMS; 2H at 3.45 (d), 1H at 7.03 (s), 8H at 7.2 to 8.4 (m), 2H at 9.7 (interchangeable).

| Elemental analysis | C % | H % | O % | P % |
|---|---|---|---|---|
| calculated: | 60.76 | 4.14 | 29.30 | 9.80 |
| found: | 60.77 | 4.17 | | 9.83 |

Example 2

(Phenyl-2-Oxo-4-4H-(1) Benzopyran-8-yl)-2-Acrylic Acid

C$_{18}$H$_{12}$O$_4$   MW = 292.27   [Formula 42]

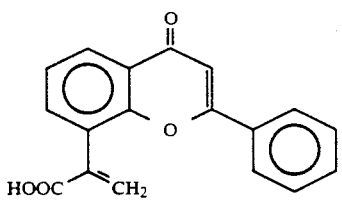

8.4 g (0.03 mole) of oxo-4-phenyl-2-4H-{4}-benzopyran-8-acetic and 81 ml of N,N,N',N' tetramethyldiaminomethane are mixed. 81 ml acetic acid are then added to the reaction mixture cooled in an ice bath. The temperature rises to 65° C., then falls to 20°C. Stirring continues for one (1) hour, then the mixture is poured into water. The solid formed is centrifuged, dried, and recrystallized in acetic acid. Weight obtained: 3.4 g (yield: 38.6%); PF$_G$=240°-247° C.; IR Vc=o (acid)=1689 cm$^{-1}$, Vc=0 (pyrone)=1620 cm$^{-1}$; NMR (DMSO)δ in ppm in relation to TMS; 2H at 6.3 (d), 1H at 7 (s), 8H at 7.3 to 8.2 (m), 1H at 13 (interchangeable).

| | Elemental analysis | | |
|---|---|---|---|
| | C % | H % | O % |
| calculated: | 73.96 | 4.14 | 21.90 |
| found: | 74.21 | 4.05 | |

Example 3

Phenyl-3-(Phenyl-2-Oxo-4-4H-[1] Benzopyran-8-yl)-2-Acrylic Acid

C$_{24}$H$_{16}$O$_4$   MW = 368.36   [Formula 43]

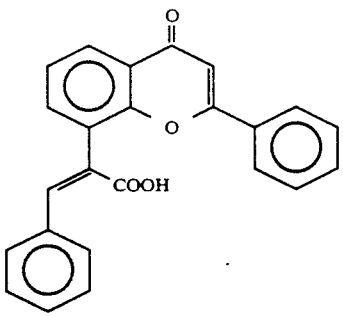

A mixture of 9.2 g (0.87 mole) of benzaldehyde, 16.8 g (0.06 mole) of oxo-4-phenyl-2-4H-[1]-benzopyran-acetic acid, 30.9 ml of acetic anhydride, and 8.32 ml of triethylamine is refluxed for ten (10) minutes. The mixture is then poured into 30 ml of water. The precipitate formed is centrifuged, dried and recrystallized in acetic acid. Weight obtained: 9.8 g (yield: 44.3%); PF$_G$=215°-220° C.; IR Vc=o (acid)=1680 cm$^{-1}$, Vc=0 (pyrone)=1630 cm$^{-1}$; NMR (CMSOδ in ppm in relation to TMS; 15H at 6.8 (m) 1H, 12.5 (interchangeable).

| | Elemental analysis | | |
|---|---|---|---|
| | C % | H % | O % |
| calculated: | 78.25 | 4.39 | 17.31 |
| found: | 77.90 | 4.11 | |

Using the same technique, the following compounds were prepared:

(Bromo-2-Phenyl)-3-(Phenyl-2-Oxo-4-4H-[1]Benzopyran-8-yl)-3-Acrylic Acid

C$_{24}$H$_{15}$BrO$_4$   MW = 447.27   [Formula 44]

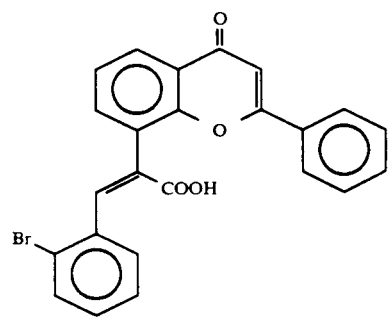

PF$_G$=217°-219° C.; IR Vc=o (acid)=1680 cm$^{-1}$, Vc=0 (pyrone)=1640 cm$^{-1}$; NMR (CMSOδ in ppm in relation to TMS; 14H at 6.8 to 8.1 (m) 1H at 12.8 (interchangeable).

| | Elemental analysis | | | |
|---|---|---|---|---|
| | C % | H % | Br % | O % |
| calculated: | 64.44 | 3.38 | 17.87 | 14.31 |
| found: | 64.29 | 3.37 | 17.58 | |

(Pyridinyl-4)-3-(Phenyl-2-Oxo-4-4H-[1]Benzopyran-8-yl)-3-Acrylic Acid

C$_{23}$H$_{15}$NO$_4$   MW = 369.36   [Formula 45]

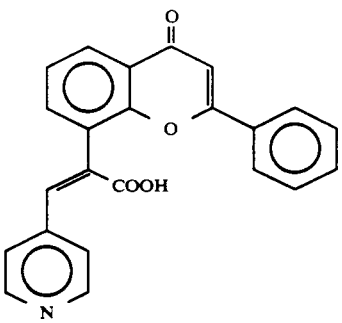

PF$_G$=272°-283° C.; IR Vc=o (acid)=1700 cm$^{-1}$, Vc=0 (pyrone)=1640 cm$^{-1}$; NMR (DMSO)δ in ppm in relation to TMS; 14H at 6.8 to 8.4 (m) 1H at 12.8 (interchangeable).

| | Elemental analysis | | | |
|---|---|---|---|---|
| | C % | H % | N % | O % |
| calculated: | 74.79 | 4.09 | 3.79 | 17.33 |

|  | Elemental analysis | | | |
|---|---|---|---|---|
|  | C % | H % | N % | O % |
| found: | 74.54 | 4.00 | 3.79 | |

(Pyridinyl-3)-3-(Phenyl-2-Oxo-4-4H-[1]Benzopyran-3-Acrylic Acid $C_{23}H_{15}NO_4$    MW = 369.36    [Formula 46]

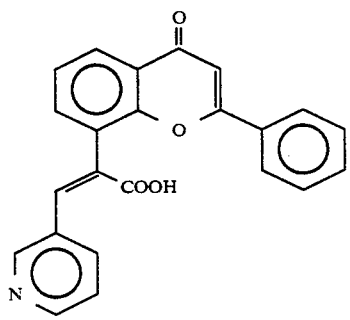

$PF_G=118°-124°$ C.; IR Vc=o (acid)=1720 cm$^{-1}$, Vc=0 (pyrone)=1630 cm$^{-1}$; NMR (DMSO)δ in ppm in relation to TMS; 14H at 7 to 8.5 (m), 12.5 (interchangeable).

$C_{21}H_{23}ClN_2O_2$    MW = 370.87    [Formula 47]

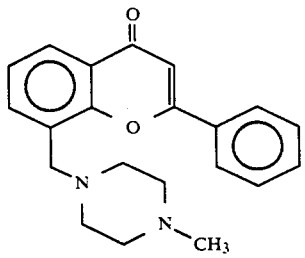

Example 4

(Chlorohydrate of [(Methyl-4-Piperazinyl) Methyl]-8-Phenyl-2-4H-[1]Benzopyranone-4

|  | Elemental analysis | | | |
|---|---|---|---|---|
|  | C % | H % | N % | O % |
| calculated: | 74.79 | 4.09 | 3.79 | 17.33 |
| found: | 74.36 | 4.09 | 3.50 | |

18.9 g (0.06 mole) of Bromomethyl-8-oxo-4-phenyl-2-4H-[1]Benzopyranone, 6.57 g (0.066 mole) of N-methyl piperzaine, and 8.3 g (0.06 mole) of potassium carbonate in 200 ml of toluene are refluxed for 8 hours. Insolubles are filtered, and the solvent is evaporated in a vacuum. The solid obtained is recrystallized in hexane. Weight obtained: 9.69 g. $PF_G=139°$ C.; IR Vc=0 (pyrone)=1640 cm$^{-1}$. Using an HCl treatment in CHCl$_3$, the chlorohydrate is obtained: $PF_G=244°-246°$ C.

|  | Elemental analysis | | | | |
|---|---|---|---|---|---|
|  | C % | H % | Cl % | N % | O % |
| calculated: | 68.00 | 6.25 | 9.56 | 7.56 | 8.63 |
| found: | 68.34 | 5.86 | 9.80 | 7.61 | |

Using the same technique, the following compounds were prepared:

(Bromohydrate of N[Imidazolinyl-2], N [(Oxo-4-Phenyl-2-4H-[1]Benzopyran-8-yl) Methyl]-Dichloro-2-6-Aniline $C_{25}H_{20}BrCl_2N_3O_2$    MW = 545.26    [Formula 48]

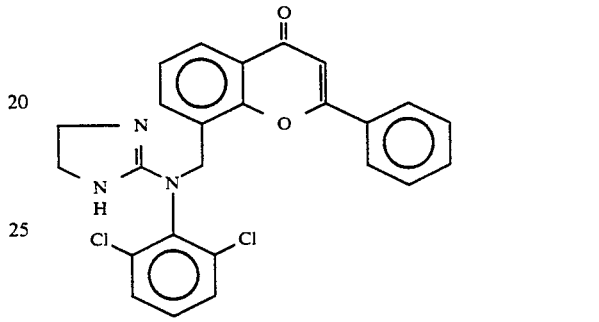

$PF_G=289°-290°$ C.; IR Vc=o (pyrone)=1640 cm$^{-1}$; V NH=3000-3200 cm$^{-1}$; NMR (DMSO)δ in ppm in relation to TMS; 4H at 3.4 (s), 2H at 5.5 (s), 1H at 7 (s), 11H at 7.2 to 8.3 (m) 2H at 8.5 to 9.5 (interchangeable).

|  | Elemental analysis | | | | | |
|---|---|---|---|---|---|---|
|  | C % | H % | Br % | Cl % | N % | O % |
| calculated: | 55.06 | 3.70 | 14.66 | 13.00 | 7.71 | 5.87 |
| found: | 55.14 | 3.63 | 14.56 | 13.09 | 7.07 | |

[(Oxo-4-Phenyl-2-4H-(1) Benzopyran-8-yl Methyl Amino]-4-Benzoic Acid $C_{23}H_{17}NO_4$    MW = 371.396    [Formula 49]

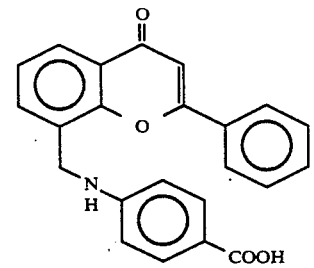

$PF_G=269°-271°$ C.; IR Vc=o (acid)=1710 cm$^{-1}$, Vc=0 (pyrone)=1640 cm$^{-1}$; NMR (DMSO)δ in ppm in relation to TMS; 2H at 4.8 (m), 13H at 6.9 to 8.27 (m), 1H at 12.6 (interchangeable).

|  | Elemental analysis | | | |
|---|---|---|---|---|
|  | C % | H % | N % | O % |
| calculated: | 74.38 | 4.61 | 3.77 | 17.24 |

N-[(Oxo-4-Phenyl-2-4H-(1)Benzopyran-8-yl)Methyl]N-Methyl, Amino-4-Benzoic Acid C$_{24}$H$_{19}$NO$_4$   MW = 385.424   [Formula 50]

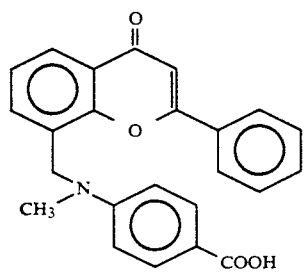

PF$_G$=260°-262° C.; IR Vc=o (acid)=1710 cm$^{-1}$, Vc=0 (pyrone)=1640 cm$^{-1}$; NMR (DMSO)δ in ppm in relation to TMS; 3H at 3.2 (s), 2H at 5 (s), 13H at 6.8 to 8.4 (m), 1H at 12.6 (interchangeable).

| | Elemental analysis | | | |
|---|---|---|---|---|
| | C % | H % | N % | O % |
| calculated: | 74.79 | 4.97 | 3.63 | 16.60 |
| found: | 74.51 | 4.81 | 3.47 | |

[(Oxo-4-Phenyl-2-4H-[1]Benzopyran-8-yl Methylamino]-3, Methyl-3, Propanediol-1-3

C$_{20}$H$_{24}$NO$_4$   MW = 339.398   [Formula 51]

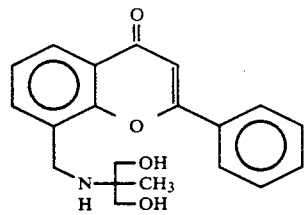

PF$_G$=150°-152° C.; IR Vc=o (pyrone)=1630 cm$^{-1}$ V OH=3380 cm$^{-1}$; NMR (DMSO)δ in ppm in relation to TMS; 3H at 1 (s), 4H at 3.2 (d), 2H at 4 (s), 2H at 4.5 (t, (interchangeable), 1H at 7 (s), 8H at 7.2 to 8.2 (m).

| | Elemental analysis | | | |
|---|---|---|---|---|
| | C % | H % | N % | O % |
| calculated: | 70.78 | 6.24 | 4.13 | 18.25 |
| found: | 70.51 | 6.42 | 4.37 | |

-continued

| | Elemental analysis | | | |
|---|---|---|---|---|
| | C % | H % | N % | O % |
| found: | 74.08 | 4.59 | 3.91 | |

Chlorohydrate of (Aminomethyl)-8-Phenyl-2-4H-[1]Benzopyranone-4

C$_{16}$H$_{14}$ClNO$_4$   MW = 287.19   [Formula 52]

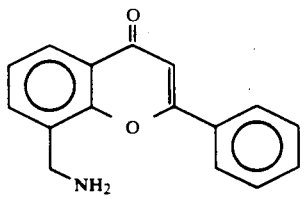

PF$_G$=275°-279° C.; IR V NH$_3^+$=3100 to 2600 cm$^{-1}$; Vc−(pyrone)=1620 cm$^{-1}$; NMR (DMSO)δ in ppm in relation to TMS; 2H at 4.4 (s), 1H at 7.1, 8H at 7.3 to 8.4 (m), 3H at 8.8 (interchangeable).

| | Elemental analysis | | | | |
|---|---|---|---|---|---|
| | C % | H % | Cl % | N % | O % |
| calculated: | 64.76 | 5.1 | 11.95 | 4.72 | 13.48 |
| found: | 65.05 | 4.73 | 12.08 | 4.46 | |

Phenyl-2-(Trimethoxy-3,4,5-Phenylaminomethyl)-8-4H-[1]Benzopyranone-4

C$_{24}$H$_{23}$NO$_5$   MW = 417.47   [Formula 53]

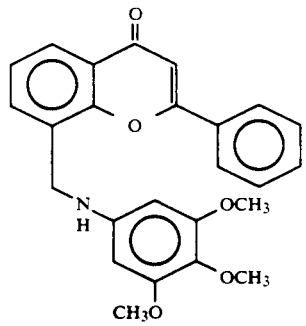

PF$_G$=219°-2221° C.; IR V NH=3350 cm$^{-1}$, Vc=o (pyrone)=1620 cm$^{-1}$; NMR (CF$_3$COOD)δ in ppm in relation to TMS; 6H at 3.15 (s), 3H at 3.35 (s), 2H at 4.93 (s), 1H at 6.1 (s), 11H at 7 to 8.3 (m).

| | Elemental analysis | | | |
|---|---|---|---|---|
| | C % | H % | N % | O % |
| calculated: | 74.93 | 5.55 | 3.35 | 19.16 |
| found: | 71.65 | 5.58 | 3.35 | |

Example 5

(Acetyloxy-1-Ethyl)-8-Phenyl-2-4H-[1]Benzopyranone-4

$C_{19}H_{16}O_4$   MW = 308.32   [Formula 54]

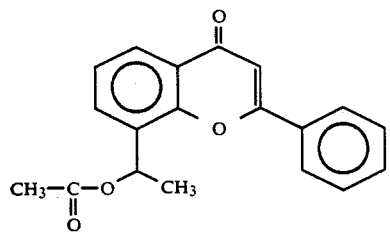

61.2 g (0.186 mole) of (bromo-1-ethyl)-8-phenyl-2-4H-[1]benzopyranone-4 and 20.1 g (0.204 mole) of potassium acetate in 290 ml of DMF are mixed and heated, with stirring to 45° C. Heating is stopped and the reaction mixture is returned to room temperature for 3 hours, with stirring. After one night at rest, the mixture is poured into ice water. The precipitate formed is filtered and recrystallized in alcohol. Weight obtained: 51 g (yield: 88.9%);

$PF_G$=137° C.; IR Vc=o (ester)=1740 cm$^{-1}$, Vc=o (pyrone)=1640 cm$^{-1}$; NMR (CDCl$_3$)δ in ppm in relation to TMS; 3H at 1.7 (d), 3H at 2.1 (s), 1H at 6.6 (g), 1H at 6.8, 8H at 7.2 to 8.4 (m).

Example 6

(Hydroxy-1-Ethyl-8-Phenyl-2-4H-[1]Benzopyranone-4

$C_{17}H_{14}O_3$   MW = 266.3   [Formula 55]

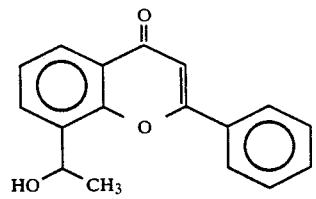

194.3 g (0.63 mole) of (acetyloxy-1-ethyl)-8-phenyl-2-4H-[1]benzopyranone-4 68.8 g (0.818 mole) of sodium bocarbonate are mixed in 239 ml of ethanol and 1628 ml of water. The mixture is kept under reflux for 5 hours. The mixture is heat-filtered, the filtrate is evaporated in a vacuum, the residue is taken up in water and recrystallized in toluene. Weight obtained: 152.9 g (yield: 91%);

$PF_G$=154°-157° C; IR V OH=3350 cm$^{-1}$, Vc=O (pyrone)=1620 cm$^{-1}$; NMR (CDCl$_3$)δ in ppm in relation to TMS; 3H at 1.62 (d), 1H at 2.8 (exchangeable).

| | Elemental analysis | | |
|---|---|---|---|
| | C % | H % | O % |
| calculated: | 76.67 | 5.30 | 18.03 |
| found: | 76.50 | 5.19 | |

Example 7

Acetyl-8-Phenyl-2-4H-1 Benzopyranone-4

$C_{17}H_{12}O_3$   MW = 264.28   [Formula 56]

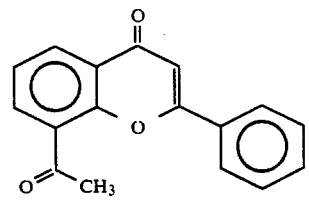

59.5 g (0.223 mole) of (hydroxy-1-ethyl)-8-phenyl-2-4H-[1]benzopyranone-4 are placed in 670 ml of dioxane. The medium is heated until a solution is obtained. This is then cooled to 20° C., and a reagent solution, prepared using 19.7 g (0.19 mole) of CrO$_3$, 50 ml of water, 13.6 ml of concentrated H$_2$SO$_4$ is added in a dropwise manner. This mixture is kept for three hours at room temperature while being stirred, the insoluble is filtered, the filtrate is evaporated in a vacuum and the residue obtained is recrystallized in methyl isobutylcetone. Weight obtained: 43.3 g (yield: 73.4%);

$PF_G$=125°-126° C.; IR Vc=o (cetone)=1675 cm$^{-1}$, Vc=0 (pyrone)=1690 cm$^{-1}$; NMR (CDCl$_3$)δ in ppm in relation to TMS; 3H at 2.8 (s), 1H at 6.8 (s), 8H at 7.3 to 8.6 (m).

| | Elemental analysis | | |
|---|---|---|---|
| | C % | H % | O % |
| calculated: | 77.26 | 4.58 | 18.16 |
| found: | 77.23 | 4.53 | |

Example 8

(Bromoacetyl)-8-Phenyl-2-4H-[1]Benzopyranone-4

$C_{17}H_{11}BrO_3$   MW = 343.18   [Formula 57]

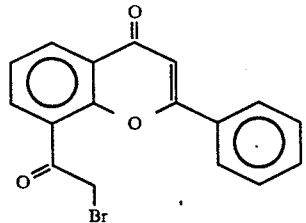

To a solution of 40 g (0.19 mole) of acetyl-8-phenyl-2-4H-[1]benzopyranone-4 in 750 ml of dioxane, 56.9 g (0.151 mole) of phenyltriethylammoniumtribromide are added. The mixture is stirred for 48 hours at room temperature, filtered, and the precipitate obtained is washed in water and recrystallized in acetone. Weight obtained: 42.9 g (yield: 82%);

$PF_G$=142° C.; IR Vc=o −1630 cm$^{-1}$, NMR (CDCl$_3$)δ in ppm in relation to TMS; 2H at 4.64 (s), 1H at 6.8 (s), 8H at 7.2 to 8.6 (m).

Example 9

(Amino 2-Thiazol-4-yl)-8-Phenyl-2-2H-[1]Benzopyranone-4

C₁₈H₁₂N₂O₂S    MW = 320.37    [Formula 58]

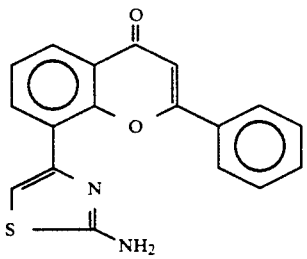

A mixture of 5 g (0.0146 mole) of (bromoacetyl)-8-phenyl-2-4H-[1]benzopyranone-4 and 2.22 g g (0.029 mole) thiourea in 100 ml of ethanol is heated for three hours under reflux, then poured into 200 ml of ice water. The precipitate formed is filtered, washed in water and recrystallized in a mixture of water and DMF. Weight obtained: 2.8 g (yield: 59%); IR V NH₂=3300 to 3350 cm⁻¹ Vc=o=1630 cm⁻¹; NMR (CDCl₃)δ in ppm in relation to TMS; 2H at 3.34 (interchangeable).

| | Elemental analysis | | | | |
|---|---|---|---|---|---|
| | C % | H % | N % | O % | S % |
| calculated: | 67.48 | 3.78 | 8.74 | 9.99 | 10.01 |
| found: | 67.57 | 3.65 | 8.84 | | 10.06 |

Using this same technique, the following compounds were prepared:

[Methyl-2-Thiazol-4yl)-8-Phenyl-2-4H-[1]Benzopyranone-4

C₁₉H₁₃NO₂S    MW = 319.37    [Formula 59]

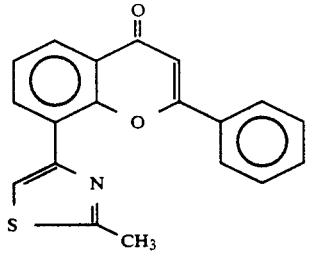

PF<sub>G</sub>=148°-153° C.; IR Vc=o (acid)=1639 cm⁻¹, NMR (CDCl₃)δ in ppm in relation to TMS; 3H at 2.8 (s), 1H at 6.8 (s), 9H at 7.2 to 8.5 (m).

| | Elemental analysis | | | | |
|---|---|---|---|---|---|
| | C % | H % | N % | O % | S % |
| calculated: | 71.45 | 4.10 | 4.39 | 10.02 | 10.04 |
| found: | 71.39 | 4.03 | 4.36 | | 10.30 |

(Imidazo [2,1-B]Thiazol-6-yl)-8-Phenyl-2-4H-[1]Benzopyranone-4

C₂₀H₁₂N₂O₂S    MW = 344.39    [Formula 60]

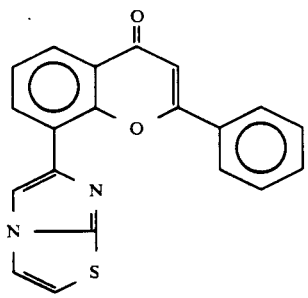

PF<sub>G</sub>=229°-233° C.; IR Vc=o=1630 cm⁻¹, NMR (DMSO+CF₃COOD)δ in ppm in relation to TMS; 1H at 7 (s), 11H at 7.4 to 8.8 (m).

| | Elemental analysis | | | | |
|---|---|---|---|---|---|
| | C % | H % | N % | O % | S % |
| calculated: | 69.75 | 3.51 | 8.14 | 9.28 | 9.31 |
| found: | 69.50 | 3.59 | 8.01 | | 9.37 |

(Imidazo [1,2,-A]Pyridin-2-yl)-8-Phenyl-2-4H-[1]Benzopyranone-4

C₂₂H₁₄N₂O₂    MW = 338.35    [Formula 61]

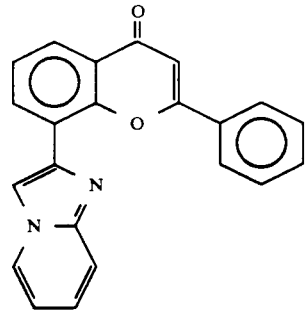

PF<sub>G</sub>=203°-205° C.; IR Vc=o=1635 cm⁻¹, NMR (CDCL₃)δ in ppm in relation to TMS; 1H at 6.8 (s), 13H at 7 to 8.7 (m).

| Elemental analysis | C % | H % | N % | O % |
|---|---|---|---|---|
| calculated | 78.09 | 4.17 | 8.28 | 9.46 |
| found | 78.16 | 4.12 | 8.26 | |

(Indolizin-2-yl)-8-Phenyl-2-4H-[1]Benzopyranone-4

$C_{23}H_{15}NO_2$    MW = 337.36    [Formula 62]

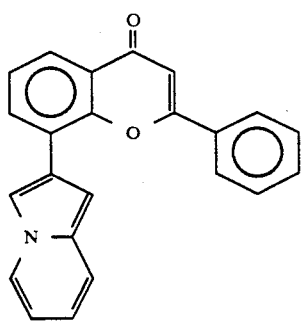

PF$_G$=204°–207° C.; IR Vc=o 1639 cm$^{-1}$, NMR (CDCL$_3$)δ in ppm in relation to TMS; 1H at 6.8 (s), 1H at 7.3 to 8.3 (m).

| Elemental analysis | C % | H % | N % | O % |
|---|---|---|---|---|
| calculated | 81.88 | 4.48 | 4.15 | 9.49 |
| found | 82.03 | 4.60 | 4.16 | |

Phenyl-2-(Phenyl-2-Thiazol-4-yl)-8-4H-[1]Benzopyranone-4

$C_{24}H_{15}O_2S$    MW = 381.46    [Formula 63]

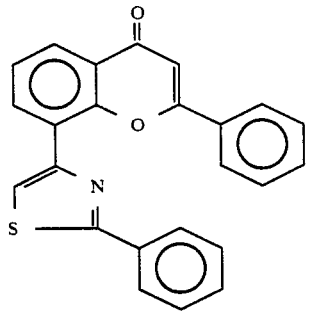

PF$_G$=199°–202° C.; IR Vc=o=1650 cm$^{-1}$, NMR (CF$_3$COOD)δ in ppm in relation to TMS; 15H at 7.4 to 8.8.

| Elemental analysis | C % | H % | N % | O % | S % |
|---|---|---|---|---|---|
| calculated | 75.57 | 3.96 | 3.67 | 8.39 | 8.41 |
| found | 75.42 | 4.03 | 3.64 | | 8.15 |

(Dihydro-2-3-Imidazo[2,1-B]Thiazol-6-yl)-8-Phenyl-2-4H-[1]Benzopyranone-4

$C_{20}H_{14}N_2O_2S$    MW = 346.40    [Formula 64]

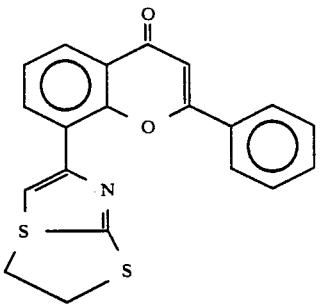

PF$_G$=226°–230° C.; IR Vc=o =1635 cm$^{-1}$, NMR (DMSO)δ in ppm in relation to TMS; 4H at 4 to 5 (m), 1H at 7 (s), 9H at 7.4 to 8.3 (m).

| Elemental analysis | C % | H % | N % | O % | S % |
|---|---|---|---|---|---|
| calculated | 69.34 | 4.07 | 8.09 | 9.24 | 9.26 |
| found | 69.21 | 4.19 | 8.32 | | 9.02 |

Example 10

Acetoxymethyl-10-Phenyl-2-4H-Naphto[1,2-b]Pyranone-4

$C_{22}H_{16}O_4$    MW = 334.37    [FORMULA 65]

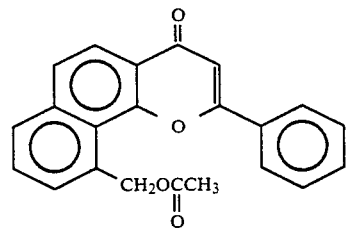

A mixture of 19.8 g (0.054 mole) of bromomethyl-10-phenyl-2-4H-naphto[1,2-b]pyranone-4, 5.3 g (0.054 mole) of potassium acetate, and 110 ml of DMF is heated to 45° with stirring. This mixture is allowed to return to room temperature while still being stirred for one hour. It is poured into a mixture of water and ice, and the solid obtained is then filtered and used in the following step, without further purification. Weight obtained: 18.5 g (quantitative yield); PF$_G$=170° C.; IR Vc=o (ester)=1740 cm$^{-1}$, Vc=o (pyrone) =1635 cm$^{-1}$; NMR (CDCl$_3$)δ in ppm in relation to TMS: 3H at 2.1 (s), 2H at 5.9 (s), 1H at 6.9 (s), 10H at 7.2 to 8.6 (m).

Hydroxymethyl-10-Phenyl-2-4H-Naphto[1,2-b]Pyranone-4

$C_{20}H_{14}O_3$    MW = 302.33    [FORMULA 66]

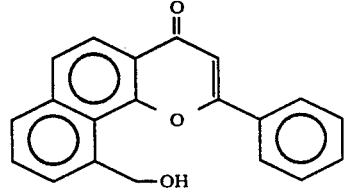

A mixture of 18.9 G (0.054 mole) of acetoxymethyl-10-phenyl-2-4H-naphto [1,2-b pyranone-4, 100 ml of ethanol and 39 g (0.07 mole) of potassium in tablet form is heated in a reflux for two hours. It is then poured into a water-ice mixture and acidified using 6N HCl. The precipitate obtained is filtered, dried, and used in the following step without further purification. Weight obtained: 16.2 g (yield=99%): $I_R$ V OH=3400 cm$^{-1}$; $V_c$ =o =1630 cm$^{-1}$; NMR (DMSO) δ in ppm in relation to TMS: 1H at 3.5 (s, large), 2H at 5.4 (s), 1H at 7 (s), 10H at 7.2 to 8.4.

Oxo-4-Phenyl-2-4H-Naphto[1,2-b]Pyranone-4

$C_{20}H_{12}O_4$    MW = 316.31    [FORMULA 67]

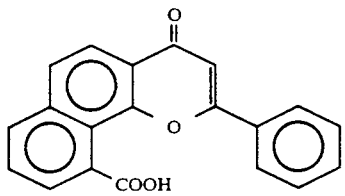

A mixture of 16.2 g (0.0536 mole) of hydroxymethyl-10-phenyl-2-4H-naphto [1,2-b]pyranone 4, 430 ml of pyridine, and 100 ml of water is heated to 60° C. 31.7 g (0.2 mole) of potassium permanganate is added over two hours in portions, then the mixture is heated for 4 hours in a reflux. It is then cooled, and treated with a watery solution of sodium metasulfite, until discoloration is obtained. It is poured into 1 liter of water, the insoluble is filtered, and the organic phase is poured off. After evaporation in a vacuum, the residue is taken up again by the water, acidified using 6N HCl. The precipitate obtained is filtered and recrystallized in acetic acid. Weight obtained: 1.1g (yield 6.5%); mp=278°-280° C.; IR Vc=o (acid)=1700 cm$^{-1}$, Vc=o (pyrone) =1620 cm$^{-1}$; NMR (DMSO) δ in ppm in relation to TMS: 1H at 7.15 (s), 10H at 7.4 to 8.4 (m), 1H at 13.5 (interchangeable).

| Elemental Analysis | C % | H % | O% |
|---|---|---|---|
| calculated | 75.96 | 3.82 | 20.24 |
| found | 75.58 | 3.77 | |

Example 11

Oxo-4-Phenyl-1-4H-[1]-Benzopyran-8-Acetate of (Ethoxycarbonyl)-1-Ethyl $C_{20}H_{20}O_6$    MW = 380.38    [FORMULA 68]

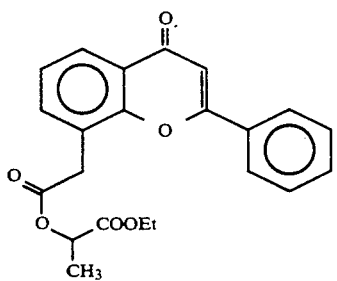

To a suspension of 30.6 g (0.109 mole) of oxo-4-phenyl-2-4H-1-benzopyran-8-acetic acid in 1.9 l of boiling ethanol is added dropwise a solution of 7.2 g (0.109 mole) of potassium in 100 ml of ethanol. The solution obtained is stirred for 30 minutes, allowed to return to room temperature, and evaporated in a vacuum. The residum is taken up using 300 ml of ethanol and evaporated in a vacuum, then taken up agin using 30 ml of benzene and evaporated in a vacuum. 546 ml of methyl isobutylketone (MIBK) is added to the residuum, followed by a solution of 21.7 g (0.12 mole) of ethyl α-bromopropionate in 55 ml of MIBK. This mixture is heated in a reflux for 3 hours; next, 12 g (0.066 mole) of ethyl α-bromopropionate is added before continuing heating for 5 hours in a reflux. Heat-filtratioin is carried out, and the filtrate is evaporated in a vacuum. The residuum is triturated in hexane in order to obtain a precipitate which is filtered, washed with hexane and recrystallized in isopropanol. Weight obtained: 36.2 g (yield: 87%); mp =104°-106° C.; IR Vc=o (pyrone) =1730 cm$^{-1}$, Vc=o (pyrone)=1640 cm$^{-1}$; NMR (CDCl$_3$) δ in ppm in relation to TMS: 3H at 1.2 (t), 3H at 1.46 (d), 2H at 4.1 (s), 2H at 4.18 (q), 1H at 5.18 (q), 1H at 6.8 (s), 8H at 7.2 to 8.4 (m). (interchangeable).

Hydroxy-4-methyl-5-(Oxo-4-Phenyl-2-4H-[1]-Benzopyran-8-yl)-3-5H-Furanone-2

$C_{20}H_{14}O_5$    MW = 334.31    [FORMULA 69]

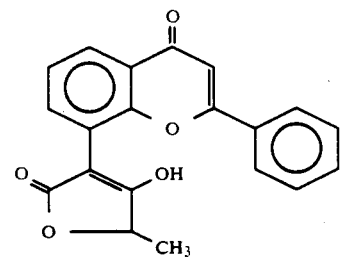

To a suspension of 2.62 g (0.109 mole) of sodium hydride in 226 ml of HMPT, is added dropwise to a solution of 41.7 g (0.109 mole) of oxo-4-phenyl-2-4H-[1]-benzopyran-8-acetate of (ethylcarbonyl)-1-ethyl in 260 ml of HMPT. This mixture is stirred overnight in an atmosphere of argon at room temperature, and is then carefully hydrolized using 2 l of 6N HCl. The precipitate obtained is filtered and recrystallized. Weight obtained: 28.3 g (yield 77%); mp=265°-268° C.; IR V OH =3400 to 2200 cm$^{-1}$, Vc=o (lactone)=1740 cm$^{-1}$; Vc=o (pyrone)=1600 cm$^{-1}$; NMR (DMSO) δ in ppm in relation to TMS: 3H at 1.6 (d), 1H at 5.2 (q), 1H at 7.1 (s), 9H at 7.2 to 8.6.

| Elemental Analysis | C % | H % | O% |
|---|---|---|---|
| calculated | 71.85 | 4.22 | 23.93 |
| found | 71.55 | 4.11 | |

Using the same technique, the following compounds were obtained:

(Chloro-4-Phenyl)-5-Hydroxy-4-(Oxo-4-Phenyl-2-4H-[1]-Benzopyran-8-yl]-3-5H-Furanone-2

$C_{25}H_{15}ClO_5$    MW = 430.83    [FORMULA 70]

-continued

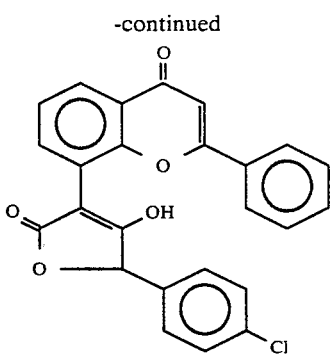

mp=265°-273° C.; IR Vc=o (lactone)=1750 cm⁻¹, Vc=o (pyrone)=1660 cm⁻¹; NMR (DMSO)δ in ppm in relation to TMS: 1H at 6.16 (s), 1H at 7 (s), 13H at 7.1 to 8.4.

| Elemental Analysis | C % | H % | Cl % | O % |
|---|---|---|---|---|
| calculated | 69.69 | 3.51 | 8.23 | 18.57 |
| found | 69.41 | 3.52 | 8.27 | |

Methyl-3-Hydroxy-4-(Oxo-4-Phenyl-2-4H-[1]-Benzo-pyran-8-yl)-5-5H-Furanone-2

C₂₀H₁₄O₅    MW = 334.31    [FORMULA 71]

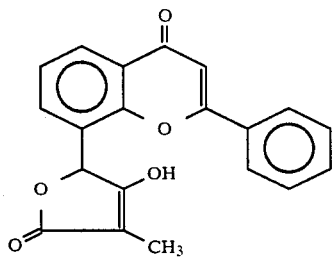

mp=160° C.; I_R v c=o (lactone)=1760 cm⁻¹, Vc=o (pyrone)=1640 cm⁻¹; NMR (DMSO)δ in ppm in relation to TMS: 3H at 1.8 (s), 1H at 6.55 (s), 1H at 7.75 (s), 9H at 7.5 to 8.3 (m).

| Elemental Analysis | C % | H % | O % |
|---|---|---|---|
| calculated | 71.85 | 4.22 | 23.93 |
| found | 71.80 | 4.22 | |

Example 12

Chlorhydrate of [(N,N-Diethylamino)-2-Ethoxy]-4-methyl-5-[Oxo-4-Phenyl-2-4H-[1]-Benzopyran-8-yl]-3-5H-Furanone-2

C₂₆H₂₈ClNO₅    MW = 469.95    [FORMULA 72]

-continued

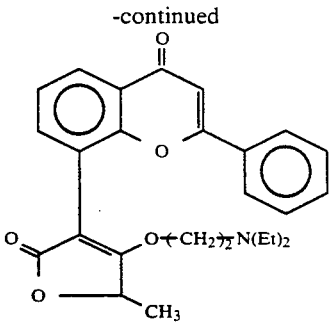

A mixture of 20 g (0.06 mole) of hydroxy-4-methyl-5-(oxo-4-phenyl-2-4H-[1]-benzopyran-8-yl)-3°-5H-furanone-2, 9.93 g (0.72 mole) of potassium carbonate, and 0.36 g (0.002 mole) of potassium iodide in 490 ml of MIBK is heated for 1 hour at. reflux. Next, a solution of 10.6 g (0.078 mole) of 2-(diethylamino)ethyl chloride in 90 ml of MIBK is added, and heating is continued for 7 hours. The minerals are heat filtered and the filtrate is evaporated in a vacuum. The residum is washed twice in hexane then solubilized in the minimum amount of acetone and diluted using hexane. A light insoluble is filtered, the filtrate is evaporated in a vacuum and the residuum is dissolved in 200 ml of ethanol. This product is cooled in an ice bath and HCl is bubbled through until a pH of 2 is achieved. By adding ether, a precipitate is obtained, which is filtered and recrystallized in an ethanol-ether mixture. Weight obtained: 16.9 g (yield 60%); mp=168°-169° C.; IR Vc=o (lactone)=1740 cm⁻¹, Vc=o (pyrone)=1640 cm⁻¹; NMR (DMSO-CDCl₃)δ in ppm in relation to TMS: 6H at 0.9 (t), 3H at 1.5 (d), 6H at 2.6 to 3.3 (m), 2H at 4.2 (t), 1H at 5.2 (q), 1H at 6.75 (s), 8H at 7.3 to 8.2.

| Elemental Analysis | C % | H % | Cl % | N % | O % |
|---|---|---|---|---|---|
| calculated | 66.45 | 6.00 | 7.55 | 2.98 | 17.02 |
| found | 66.30 | 6.20 | 7.55 | 2.83 | |

Using the same technique, the following compounds were obtained:

[Dihydro-2-5-methy-5-Oxo-2-(Oxo-4-Phenyl-2-4H-[1]-Benzopyran-8-yl)-3-Furan-4-yl]Ethyl Oxyacetate

C₂₄H₂₀O₇    MW = 420.4    [FORMULA 73]

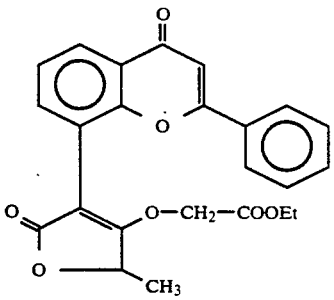

mp=153° C.; IR Vc=o NMR (ester and lactone)=1755 cm⁻¹, Vc=o (pyrone)=1640 cm⁻¹ NMR (CDCl₃) δ in ppm in relation to TMS: 3H at 1 (t), 3H at 1.7 (d), 2H at 3.9 (q), 2H at 4.5 (s), 1 H at 5.18 (q), 1H at 6.9 (s), 8H at 7.2 to 8.5.

Dihydro-2-5-methyl-5-Oxo-2-(Oxo-4-Phenyl-2-4H-[1]-Benzopyran-8-yl)-3-Furan-4-yl]Oxyacetic Acid $C_{22}H_{16}O_7$  MW = 392.39  [FORMULA 74]

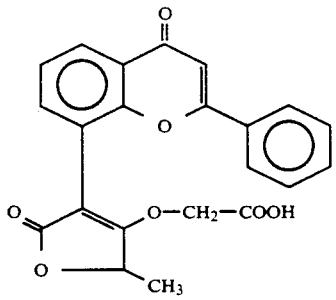

mp=257°-259° C.; IR V OH =2400 cm$^{-1}$, Vc=o (lactone)=1740 cm$^{-1}$, Vc=o (acid)=1710 cm$^{-1}$, Vc=o (pyrone)=1620 cm$^{-1}$; NMR (DMSO) δ in ppm in relation to TMS: 3H at 1.6 (d), 1H at 4 (interchangeable), 2H at 4.66 (s), 1H at 5.4 (q), 1H at 7.08 (s), 8H at 7.2 to 8.4 (m).

| Elemental Analysis | C % | H % | O % |
|---|---|---|---|
| calculated | 67.34 | 4.11 | 28.55 |
| found | 67.20 | 4.00 | |

Dimethyl Carbamothioate of O-[Dihydro-2,5-Methyl-5-Oxo-2-(Oxo-4-Phenyl-2-4H-[1]-Benzopyran-8-yl)-3-Furn-4-yl]

$C_{23}H_{19}NO_5S$  MW = 421.46

[FORMULA 75]

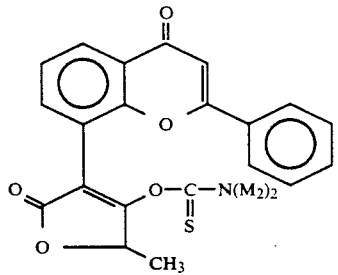

mp=173°-175° C.; IR Vc=o (lactone)=1740 cm$^{-1}$, Vc=o (pyrone)=1630 cm$^{-1}$; NMR (CDCl$_3$)δ in ppm in relation to TMS: 3H at 1.66 (d), 6H at 2.8 (s), 1H at 6.16 (q), 1H at 6.8 (s), 8H at 7.2 to 8.4 (m).

| Elemental Analysis | C % | H % | N % | O % | S % |
|---|---|---|---|---|---|
| calculated | 65.54 | 4.70 | 3.32 | 18.98 | 7.61 |
| found | 65.42 | 4.52 | 3.32 | | 7.64 |

Example 13

Acetylthiomethyl-8-Oxo-4-Phenyl-2-4H-[1]-Benzopyrane $C_{18}H_{14}O_3S$  MW = 310.38

[FORMULA 76]

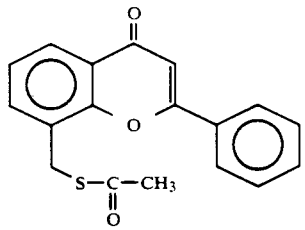

To a mixture of 17.4 g (0.152 mole) of potassium thioacetate in 120 ml of DMF is added 48 g (0.152 mole) of bromomethyl-8-phenyl-2-4H-[1]-benzopyranone-4, by portions while being stirred. This is stirred for 1 hour at room temperature and then poured into a water-ice mixture. The precipitate obtained is filtered and recrystallized in ethyl acetate. Weight obtained: 38 g (yield: 80%); mp=160° C.; IR Vc=o (ester)=1690 cm$^{-1}$, Vc=o (pyrone)=1655 cm$^{-1}$; NMR (CDCl$_3$) δ in ppm in relation to TMS: 3H at 2.4 (s), 2H at 4.5 (s), 1H at 6.9 (s), 8H at 7.2 to 8.4 (m).

Example 14

Mercaptomethyl-8-Phenyl-2-4H-[1]-Benzopyranone-4

$C_{16}H_{12}O_2S$  MW = 268.34

[FORMULA 77]

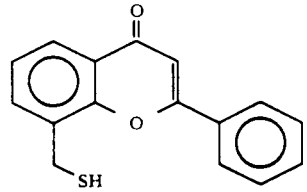

To a mixture of 38 g (0.122 mole) of thioacetylmethyl-8-phenyl-2-4H-[1]-benzopyranone-4 and 230 ml of ethanol are added at one time 150 ml of saturated ethanol in anhydrous HCl. This is heated for 18 hours in a reflux. This mixture is cooled and the precipitate obtained is heated and recrystallized in 162° C.; IR Vc=o =1640 cm$^{-1}$; NMR (CDCl$_3$) δ in ppm in relation to TMS: 1H at 2 (t), 2H at 4.1 (d), 1H at 6.8 (s), 8H at 7.2 to 8.4 (m) (interchangeable).

| Elemental Analysis | C % | H % | O % | S % |
|---|---|---|---|---|
| calculated | 71.62 | 4.51 | 11.92 | 11.95 |
| found | 71.45 | 4.48 | | 11.84 |

Using the same technique, the following compounds were prepared:

(Oxo-4-Phenyl-2-4H-[1]-Benzopyran-8-yl)-methyl]-methyl Thioacetate $C_{19}H_{16}O_4S$  MW = 340.4

[FORMULA 78]

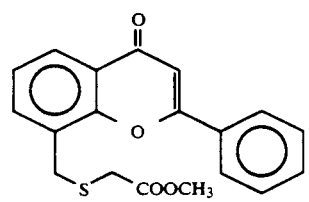

mp=110° C.; IR Vc=o (ester)=1720 cm⁻¹, Vc=o (pyrone)=1650 cm⁻¹ NMR (CDCl₃) δ in ppm in relation to TMS: 2H at 3.2 (s), 3H at 3.7 (s), 2H at 4.2 (s), 1H at 6.8 (s), 8 H at 7.2 to 8.4 (m).

(Oxo-4-Phenyl-2-4H-[1]-Benzopyran-8-yl) Methyl-Thioacetic Acid $C_{18}H_{14}O_4S$  MW = 326.37

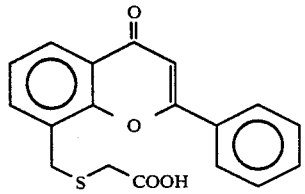

[FORMULA 79]

mp=202°-204° C.; IR V OH=3100-2400 cm⁻¹, IR Vc=o (acid)=1720 cm⁻¹, Vc=o (pyrone)=1640 cm⁻¹ NMR (DMSO) δ in ppm in relation to TMS: 2H at 3.2 (s), 2H at 4.25 (s), 1H at 6.8 (s), 9H at 7.2 to 8.4 (m).

| Elemental Analysis | C % | H % | O % | S % |
|---|---|---|---|---|
| calculated | 66.24 | 4.32 | 19.61 | 9.81 |
| found | 66.51 | 4.34 | | 10.11 |

Oxalate of Diethylamino-2-Ethoxymethyl)-8-Phenyl-2-4H-[1]-Benzopyranone-4

$C_{24}H_{27}NO_7$  MW = 441.48

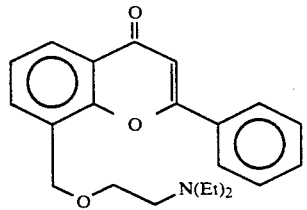

[FORMULA 80]

mp=162°-164° C.; IR Vc=o=1660 cm⁻¹; NMR (DMSO) δ in ppm in relation to TMS: 3H at 1.2 (t), 6H at 2.95 to 3.5 (m), 1H at 3.8 to 4.2 (m), 2H at 5.05 (s), 2H at 5.4 (interchangeable), 1H at 7.1 (s), 8H 7.5 to 8.5 (m).

| Elemental Analysis | C % | H % | N % | O % |
|---|---|---|---|---|
| calculated | 65.29 | 6.16 | 3.17 | 25.37 |
| found | 65.18 | 6.10 | 3.07 | |

[[Hydroxy-2-(Hydroxymethyl)-1-Ethoxy]methyl]-8-Phenyl-2-4H-[1]-Benzopyranone-4

$C_{19}H_{18}O_5$  MW = 326.33

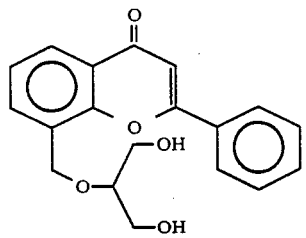

[FORMULA 81]

mp=162° C.; IR V OH =3300 cm⁻¹; IR Vc=o 1620 cm⁻¹, NMR (DMSO) δ in ppm in relation to TMS: 5H at 3.3 to 3.7 (m), 2H at 4.5 (interchangeable), 2H at 5 (s), 1H at 6.93 (s), 8H at 7.2 to 8.2 (m).

| Elemental Analysis | C % | H % | O % |
|---|---|---|---|
| calculated | 69.93 | 5.56 | 24.51 |
| found | 70.00 | 5.57 | |

Example 15

Oxo-4-Phenyl-2-4H-[1]-Benzopyran-8-Acetamide $C_{17}H_{13}NO_3$  MW = 279.28

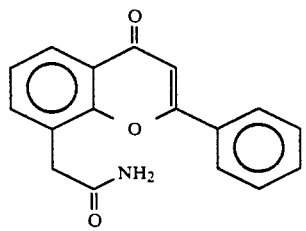

[FORMULA 82]

A suspension of 5 G (0.0178 mole) of oxo-4-phenyl-2-4H-[1]-benzopyran-8-acetic acid in 180 ml of dioxane is heated until it dissolves. A solution of 3.5 g (0.0124 mole) of N,N'-carboxyldiamidazol in 30 ml of dioxane is added and the mixture is heated for 1 hour to 80° C. It is then cooled to 20° C and approximately 10 ml (0.4 mole) liquified anhydrous ammonia at −33° C. is slowly added. The mixture is stirred for 10 minutes at 20° C., then for 3 hours at 80° C. This is left overnight, filtered, washed with hexane, then with hot 5% sodium bicarbonate solution, then with water; it is next recrystallized in ethanol. Weight obtained: 3.3 g (yield 66%); mp=232°-258° C.; IR V NH =3370 to 3200 cm⁻¹; IR vc =o (acid)=1660 cm⁻¹, Vc=o (pyrone)=1630 cm⁻¹; NMR (CDCl₃+CF₃COOD) δ in ppm in relation to TMS: 2H at 4.33 (s), 9H at 7.5 to 8.7 (m), 2H at 11.5.

| Elemental Analysis | C % | H % | N % | O % |
|---|---|---|---|---|
| calculated | 73.13 | 4.69 | 5.01 | 17.19 |
| found | 73.13 | 4.69 | 5.00 | |

Example 16

Oxo-4-Phenyl-2-4H-[1]-Benzopyran-8-Thioacetamide $C_{17}H_{23}NO_2S$  MW = 295.35

-continued

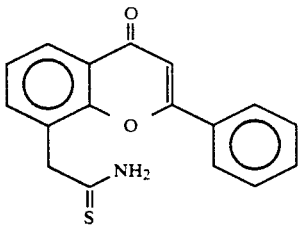

[FORMULA 83]

In a mixture of 60 g (0.229 mole) of oxo-4-phenyl-2-4H-[1]-benzopyran-8-acetonitrile, 16.2 ml (0.116 mole) of triethylamine and 900 ml of pyridine, a stream of $H_2S$ is bubbled through for 3 hours. A nitrogen stream is then passed through this mixture and it is poured into 5 l of ice water, acidified to a pH 5-6 with HCl, filtered, washed in ether, dried, and crystallized in DMF. Weight obtained: 24.7 g (yield: 36%); mp=223°-224° C.; IR V NH =3250 and 3080 cm$^{-1}$; IR Vc=o =1620 cm$^{-1}$; NMR (DMSO) δ in ppm in relation to TMS: 2H at 4.15 (s), 1H at 6.9 (s), 8H at 7.2 to 8.4 (m), 2H at 9.4 (s).

| Elemental Analysis | C % | H % | N % | O % | S % |
|---|---|---|---|---|---|
| calculated | 69.13 | 4.44 | 4.74 | 10.83 | 10.86 |
| found | 69.22 | 4.38 | 4.80 | | 10.68 |

Example 17

Phenyl-2-[(Phenyl-4-THIAZOL-2-yl)methyl]-8-4H-[1]-Benzopyranone-4

$C_{25}H_{17}NO_2$  MW = 395.46

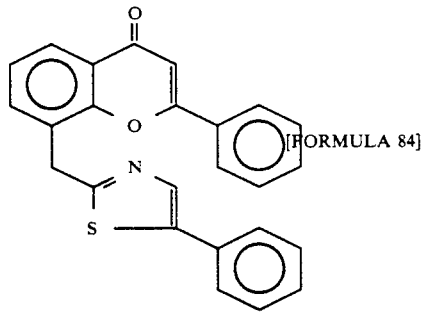

[FORMULA 84]

A mixture of 5 g (0.0169 mole) of oxo-4-phenyl-2-4H-[1]-benzopyran-8-thioacetamide, 4g (0.0203 mole) of d-bromoacetophenone and 120 ml of methoxyethanol is heated for five hours of reflux, then cooled and left overnight at −20° C. The solid obtained is filtered and recrystallized in MIBK then in acetone. Weight obtained: 3.3 g (yield: 49%); IR Vc=o 1620 cm$^{-1}$; NMR (CDCl$_3$) δ in ppm in relation to TMS: 2H at 4.7 (s), 1H at 6.75 (s), 14 H at 7.1 to 8.3 (m).

| Elemental Analysis | C % | H % | N % | O % | S % |
|---|---|---|---|---|---|
| calculated | 75.92 | 4.33 | 3.54 | 8.09 | 8.11 |
| found | 75.73 | 4.23 | 3.52 | | 8.31 |

Using this same technique, the following compounds were prepared:

[(Oxo-4-Phenyl-2-4H-[1]-Benzopyran-8-yl)methyl]-2-Thiazol-4-Ethyl Carboxylate $C_{22}H_{17}NO_4S$  MW = 391.43

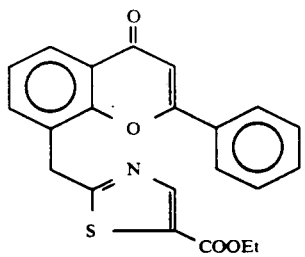

[FORMULA 85]

mp=152°-153° C.; IR Vc=o (ester)=1710 cm$^{-1}$, Vc =o (pyrone)=1640 cm$^{-1}$; NMR (CDCl$_3$) δ in ppm in relation to TMS: 3H at 1.3 (t) 2H at 4.4 (q), 2H at 4.73 (s), 1H at 6.7 (s), 9H at 7.1 to 8.3 (m).

[Oxo-4-Phenyl-2-4H-{12}-Benzopyran-8-yl)methyl-2-Thiazol-4-Carboxylic Acid $C_{20}H_{13}NO_4S$  MW = 362.38

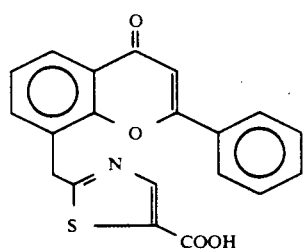

[FORMULA 86]

mp=237°-240° C.; IR V OH=3100 to 2400 cm$^{-1}$; IR Vc=o (acid)=1720 cm$^{-1}$, Vc=o (pyrone),=1620 cm$^{-1}$ NMR (DMSO) δ in ppm in relation to TMS: 1H at 3.4 (exchangeable), 2H at 4.7 (s), 1H at 6.9 (s), 8H at 7.2 to 8.15 (m), 1H at 8.2 (s).

| Elemental Analysis | C % | H % | N % | O% | S % |
|---|---|---|---|---|---|
| calculated | 66.10 | 3.61 | 3.85 | 17.61 | 8.82 |
| found | 69.83 | 3.60 | 3.87 | | 8.60 |

Example 18

[Oxo-4-Phenyl-2-4H-[1]-Benzopyran-8-yl)methylene]-2-Hydrazine Carbothioamide $C_{17}H_{13}N_3O_2S$  MW = 323.36

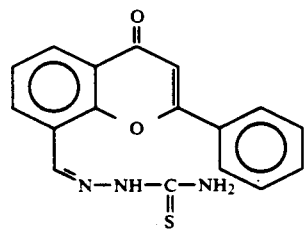

[FORMULA 87]

A suspension of 5 g (0.02 mole) of (oxo-4-phenyl-2-4H-[1]-benzopyran-8-yl) carboxaldehyde in 120 ml of dioxane was heated until dissolution. This was cooled to 25° C., a solution of 2 g (0.022 mole) of thiosemicarbazide in 40 ml of dioxane was added and this was heated for 5 minutes at 90° C., then left to return to 25° C. while stirring. The precipitate was filtered and recrystallized in methoxyethanol. Weight obtained: 48 g (yield: 41%); mp=258°–262° C.; IR V NH =3400 to 3100 cm$^{-1}$, V C =0: 7640 cm$^{-1}$.

| Elemental Analysis | C % | H % | N % | O % | S % |
|---|---|---|---|---|---|
| calculated: | 63.14 | 4.05 | 13.00 | 9.90 | 9.92 |
| found: | 63.12 | 4.04 | 13.00 | | 9.87 |

Using the same method, the following compound was prepared:

Dihydro-4,5-[1H]-Imidazol-2-yl-Hydrazone Bromhydrate of (Oxo-4-Phenyl-2-4H-[1]-Benzopyran-8-yl) Carboxaldehyde $C_{19}H_{17}BrN_4O_4$  MW = 413.28

[FORMULA 88]

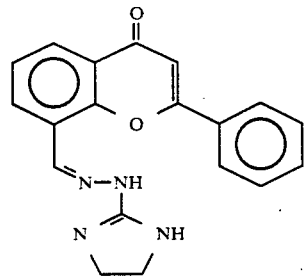

mp=301°–303° C.; IR: V NH=3300 cm$^{-1}$; V C=N–C=O=1660 and 1640 cm$^{-1}$; NMR (DMSO) δ in ppm in relation to TMS: 2H to 3.4 (s), 4H to 3.8 (s), 1H to 7.1 (s), 10H from 7.3 to 9 (m of which 1H is exchangeable).

| Elemental Analysis | C % | H % | Br % | N % | O % |
|---|---|---|---|---|---|
| calculated: | 55.21 | 4.15 | 19.34 | 13.56 | 7.74 |
| found: | 54.96 | 4.09 | | 13.62 | |

Example 19

(Oxo-4-Tetrahydro-2,3,5,6-4H-Pyran-2-yl)-8-Phenyl-2-4H-[1]-Benzopyranone-4

$C_{20}H_{16}O_4$  MW = 320.33  [FORMULA 89]

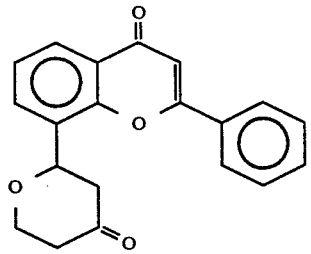

20 g (0.08 mole) of oxo-4-phenyl-2-4H-[1]-benzopyran-8-carboxaldehyde were added in parts to a mixture of 22.8 g (0.16 mole) of trimethylsilyloxy-2-butadiene-1-3 and 12 g (0.088 mole) of anhydrous ZnCl$_2$ in 500 ml of anhydrous dioxane. This was brought to reflux for 8 hours under nitrogen and then left under stirring for 48 hours at room temperature. A slight insoluble product was filtered and 1 liter of a solution of 5% NaHCO$_3$ was added to the filtrate. The insoluble product formed was filtered and the filtrate was extracted using ethyl acetate, then dried and evaporated under a vacuum. The residue was dissolved in 300 ml of methanol and brought to reflux for 3 hours. After having been cooled to 25° C., 3.6 ml of acetic acid were added and this was left under stirring for one night. This was evaporated under a vacuum and the residue was recrystallized in MIBK. Weight obtained: 9.2 g (yield: 30%); mp=220°–221° C.; IR V C=O (pyranone)=7695 cm$^{-1}$, V C=O (pyrone)=1640 cm$^{-1}$; NMR (CDCl$_3$)δ in ppm in relation to TMS: 4H from 2.3 to 3.2 (m), 2H from 3.7 to 4.7 (m), 1H to 5.3 (dd), 1H to 6.8 (s), 8H from 7.1 to 8.3 (m).

| Elemental Analysis | C % | H % | O % |
|---|---|---|---|
| calculated: | 74.98 | 5.03 | 19.98 |
| found: | 75.03 | 4.81 | |

Example 20

(Hydroxy-4-Tetrahydro-3,4,5,6-2H-Pyran-2-yl)-8-Phenyl-2-4H-[1]-Benzopyranone-4

$C_{20}H_{18}O_4$  MW = 322.34  [FORMULA 90]

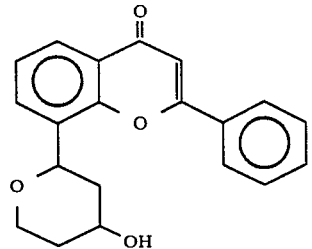

A mixture of 6.8 g (0.021 mole) of the compound of Example 18,116 ml of dioxane and 58 ml of methanol was heated until dissolution. It was cooled to 35° C and 0.9 g (0.023 mole) of NABH$_4$ were added in parts. This was then brought to reflux for 3 hours. After having been cooled, water was added and the precipitate obtained was filtered and recrystallized in isopropanol. Weight obtained: 3 g (yield: 43%); mp=187°–190° C.; IR VOH 3400°–3200 cm$^{-1}$; Vc=o =1610 cm$^{-1}$ NMR CDCP$_3$) δ in ppm in relation to TMS: 4H at 1 to 2.76 m; 4H from 3.2 to 4.4 (m, of which 1H is exchangeable), 1H to 4.9 (dd) 1H to 6.8 (s), 8H from 7.2 to 8.2 (m).

| Elemental Analysis | C % | H % | O % |
|---|---|---|---|
| calculated: | 74.52 | 5.63 | 19.85 |
| found: | 74.82 | 5.52 | |

Example 21

Oxo-4-4-(Oxo-Phenyl-2-4H-[1]-Benzopyran-8-yl)-4-Buten-2-oic Acid $C_{19}H_{12}O_5$  MW = 320.29  [FORMULA 91]

-continued

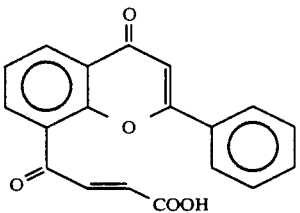

A mixture of 2 g (0.0076 mole) of acetyl-8-phenyl-2-4H-[1]-benzopyranone-4, 1.4 g (0.019 mole) of glyoxylic acid and 25 ml of acetic acid was brought to reflux for 2 hours. This was then poured into water and the precipitate formed was filtered. This was heat dissolved with a solution of 5% NaHCO$_3$ and acidified using acetic acid. The precipitate was filtered, washed with water and recrystallized in the dioxane-hexane mixture. Weight obtained: 0.5 g (yield: 20.6%); mp=217°-218° C.; IR V C=O (acid) 1710 cm$^{-1}$, V C=O (ketone)=1760 cm$^{-1}$, V C=O (pyrone)=1620 cm$^{-1}$; NMR (DMSO) δ in ppm in relation to TMS 1H to 3.8 (exchangeable), 1H from 6.5 to 8.5 (m).

| Elemental analysis | C % | H % | O % |
|---|---|---|---|
| calculated: | 71.24 | 3.78 | 24.98 |
| found: | 71.17 | 3.52 | |

Example 22

(Oxo-4-Phenyl-2-4H-[1]-Benzopyran-8-yl)-2-Hydroxy-2-Acetic Acid

C$_{17}$H$_{12}$O$_5$    MW = 296.28    [FORMULA 92]

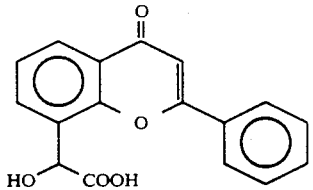

A mixture of 8.75 g (0.134 mole) of potassium cyanide, 125 ml of water, 1.25 l of dioxane, 53 g (0.5 mole) of Na$_2$CO$_3$ and 15.32 g (0.061 mole) of oxo-4-phenyl-2-4H-benzopyran-8-carboxaldehyde was stirred at room temperature for 1 hour. 75 ml of acetic acid were then added and this was stirred for 6 hours at room temperature. It was poured into 4 liters of water. The precipitate obtained was washed with water and recrystallized in an acetic acid-water mixture. Weight obtained 2.5 g (Yield: 14%); IR V OH—3450 cm$^{-1}$, V C=O (acid)=1720 cm$^{-1}$, V C=O (pyrone)=1620 cm$^{-1}$; NMR (DMSO) δ in ppm in relation to TMS: 1H at 3.4 (interchangeable), 1H at 5.6 (s), 1H at 7(s), 9H at 7.3 to 8.3 (m, of which 1H is interchangeable).

| Elemental analysis | C % | H % | O % |
|---|---|---|---|
| calculated: | 68.92 | 4.08 | 27.00 |
| found: | 68.98 | 4.19 | |

Example 23

(Oxo-4-Phenyl-2-4H-[1]-Benzopyran-8-yl)-2-Hydroxy-2-Ethyl Acetate

C$_{19}$H$_{16}$O$_5$    MW = 324.32    [Formula 93]

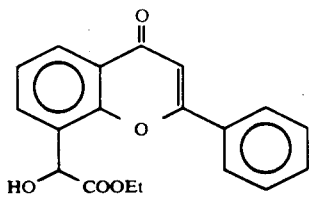

A mixture of 29 g (0.098 mole) of (oxo-4-phenyl-2-4H-[1]-benzopyran-8-yl)-2-hydroxy-2 acetic acid and 35 ml of concentrated H$_2$SO$_4$ in 585 ml of ethanol are brought to reflux for 5 hours. The mixture was then poured into water, extracted using ethyl acetate, dried, evaporated and the white solid obtained was recrystalized in MIBK-hexane. Weight obtained: 20.3 g (Yield: 64%); MP$_K$=135° C.; IR: V OH=3420 cm$^{-1}$, V C=O (ester)=1730 cm$^{-1}$, V C=O (pyrone)=1640 cm$^{-1}$.

Example 24

(Oxo-4-Phenyl-2-4H-[1]Benzopyran-8-yl)-2-Oxo-2-Ethyl Acetate

C$_{19}$H$_{14}$O$_5$    MW = 322.3    [Formula 94]

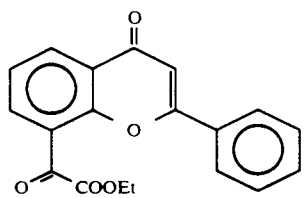

0.79 g (0.0077 mole) of CrO$_3$ and 0.84 g (0.0077 mole) of chlorotrimethylsilane were dissolved in 10 ml of methylene chloride. A solution of 2.5 g (0.0077 mole) of (oxo-4-phenyl-2-4H-[1]benzopyran-8-yl)-2-hydroxy-2-ethyl acetate in 20 ml of methylene chloride was added while cooling the red solution obtained. This was stirred at room temperature for 3 hours 50 minutes. The medium was then passed on a silica column and eluted with CHCl$_3$. This was evaporated and the residue was recrystallized in hexane. Weight obtained: 0.9 g (Yield: 36.3%); MP$_K$=85-°90° C.; IR V C=O (ester)=1730 cm$^{-1}$, V C=O (ketone)=1690 cm$^{-1}$, V C=O (pyrone)=1640 cm$^{-1}$, NMR (CDCl$_3$), δ in ppm in relation to TMS: 3H to 1.3 (t), 2H to 4.3 (q), 1H to 6.8 (s), 8H to 7.25 to 8.7 (m).

Example 25

(Oxo-4-Phenyl-2-4H[1]Benzopyran-8-yl)-2-Oxo-2-Acetate Acid

C$_{17}$H$_{10}$O$_5$    MW = 294.25    [Formula 95]

-continued

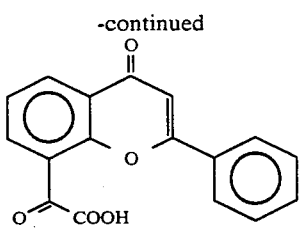

The mixture of 9.3 g (0.0288 mole) of (oxo-4-phenyl-2-4H-[1]benzopyran-8-yl)-2-oxo-2-ethyl acetate, 4.85 g (0.057 mole) of sodium bicarbonate, 150 ml of ethanol and 115 ml of water was refluxed for 4 hours 30 minutes. The ethanol was then evaporated, 150 ml of water were added, the mixture was acidified with ½ HCl and the precipitate obtained was filtered and recrystallized in dioxane. Weight obtained: 2.3 g (Yield 27%), $MP_G=232°-235°$ C., IR V C=O (acid)=1740 cm$^{-1}$, V C=O (ketone)=1690 cm$^{-1}$, V C=O (pyrone)=1660 cm$^{-1}$. NMR (DMSO) δ in ppm in relation to TMS: 1H to 7.3 (s), 9H to 7.4 to 8.5 (m, 1H of which is exchangeable).

| Elemental analysis | C % | H % | O % |
| --- | --- | --- | --- |
| calculated: | 69.39 | 3.91 | 27.19 |
| found: | 69.11 | 3.95 | |

Example 26

Methyl-2-(Oxo-4-Phenyl-2-4H-[1]Benzopyran-8-Y)-2-Methyl Propanoate $C_{20}H_{18}O_4$    MW = 322.34    [Formula 96]

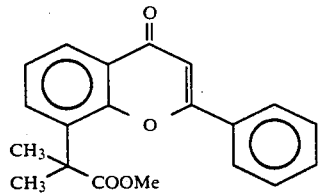

A solution of 6.7 g (0.023 mole) of oxo-4-phenyl-2-4H-[1]benzopyran-8-methyl acetate in 120 ml of DMF was added slowly to a suspension of 2.33 g (0.0485 mole of sodium hydride in 10 ml of DMF. This was stirred for one hour at room temperature, then 6.6 cm (0.1 mole) of methyl iodide in 5 ml of DMF was added dropwise. This was stirred for 6 hours at room temperature and then 6.6 ml of CIH$_3$ in 5 ml of DMF was added. This was stirred for one night, 15 ml of acetic acid were added, it was concentrated to 50 ml, water was added and the ethyl acetate was extracted. This was dried, evaporated under a vacuum and recrystallized in methanol. Weight obtained: 3.5 g (Yield 42%); $MP_K=157°$ C.; IR V C=O (ester)=1720 cm$^{-1}$, V C=O (pyrone)=1650 cm$^{-1}$; NMR (CDCl$_3$) δ in ppm in relation to TMS: 6H to 1.75 (s), 3H to 3.6 (s), 1H to 6.87 (s), 8H to 7.2 to 8.4 (m).

Example 27

Methyl-2-(Oxo-4-Phenyl-2-4H-[1]Benzopyran-8-yl)-2-Propionic Acid $C_{19}H_{16}O_4$    MW = 308.318    [Formula 97]

-continued

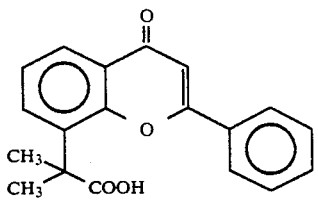

A mixture of 5.7 g (0.0177 mole) of methyl-2-(oxo-4-phenyl-2-4H-[1]benzopyran-8-yl)-2-methyl propanoate, 95 ml of acetic acid, 95 ml of concentrated sulfuric acid and 95 ml of concentrated hydrochloric acid were refluxed for 2 hours. This was then stirred for 12 hours at room temperature and brought again to reflux for 3 hours. It was cooled and the precipitate formed was filtered and stabilized in 250 ml of a 5% bicarbonate solution. It was acidified with ½ HCl and the precipitate was dried, washed with water and recrystallized in acetic acid. Weight obtained 3.1 g (Yield: 56.8%); $MP_G=255°-260$; IR V C=O (acid)=1720 cm$^{-1}$, V C=O (pyrone)=1620 cm$^{-1}$; NMR (CF$_3$COOD) δ in ppm in relation to TMS: 6H to 2 (s), 9H from 7.6 to 8.6 (m), 1H to 11.7 (exchangeable).

| Elemental analysis | C % | H % | O % |
| --- | --- | --- | --- |
| calculated: | 74.01 | 5.23 | 20.76 |
| found: | 73.93 | 5.25 | |

Example 28

Oxo-4-Phenyl-2-4H[1]-Benzopyran-8-Carboxaldehyde Oxime (8)

$C_{16}H_{11}NO_3$    MW = 265.256    [Formula 98]

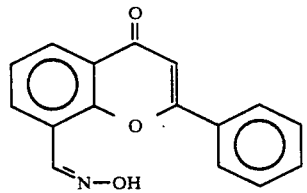

A mixture of 10 g (0.04 mole) of oxo-4-phenyl-2-4H-[1]benzopyran-8-carboxaldehyde, 3.7 g (0.054 mole) of hydroxylamine hydrochlorate, 7.1 g (0.10 mole) of sodium acetate, 20 ml of water and 40 ml of ethanol was brought to reflux for 1 hours. After cooling, the product formed was dried and recrystallized in dioxane. Weight obtained: 6.3 g (Yield: 59.4%); $MP_G=230°-238°C$.; IR V OH=3200 to 2800 cm$^{-1}$, V C=O; NMR (CF$_3$COOD), δin ppm in relation to TMS: 10 H from 7.8 to 9.5 (m).

| Elemental analysis | C % | H % | N % | O % |
| --- | --- | --- | --- | --- |
| calculated: | 72.44 | 4.18 | 5.28 | 18.10 |
| found: | 72.74 | 4.24 | 5.03 | |

Using the same method, the following compound was prepared:

Acetyl-8-Phenyl-2-4H-[1]-Benzopyranone-4- Oxime (8)

C17H13NO3    MW = 279.282    [Formula 99]

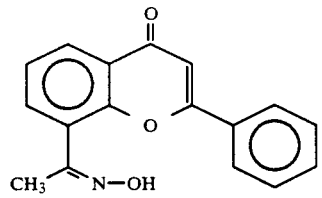

| Elemental analysis | C % | H % | N % | O % |
|---|---|---|---|---|
| calculated: | 73.10 | 4.69 | 5.02 | 17.19 |
| found: | 73.00 | 4.70 | 4.99 | |

Example 29

(Morpholin-4-yl)-3-(Oxo-4-Phenyl-2-4H-[1]-Benzopyran-8-yl)-2-Glutaronitrile

C24H21N3O3    MW = 399.43    [Formula 100]

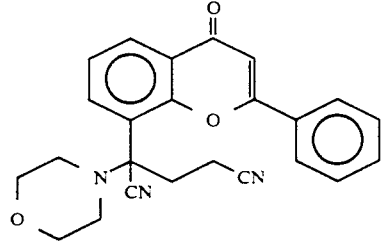

A solution of 1.33 g (0.025 mole) of acrylonitrile in 10 ml of dioxane was added dropwise to a mixture of 7 g (0.02 mole) of (morpholin-4-yl)- -(oxo-4-phenyl-2-4H-[1]benzopyran-8-yl)-2 acetonitrile. After 18 hours at room temperature, a slightly insoluble material was filtered and evaporated under a vacuum. The residue was recrystallized in isopropanol. Weight obtained: 3.1 g (Yield: 38.8%); MP$_K$=110° C.; IR V C≡N=2250 cm$^{-1}$, V C=1640 cm$^{-1}$; NMR (CDCl3) δ in ppm in relation to TMS: 8H from 1.8 to 3.2 (m); 4H to 3.9 (t), 1H to 7 (s), 8H from 7.4 to 8.6 (m).

Example 30

Oxo-4-(Oxo-4-Phenyl-2-4H-[1]Benzopyran-8-yl)-4-Butyric Acid

C19H14O5    MW = 322.3    [Formula 101]

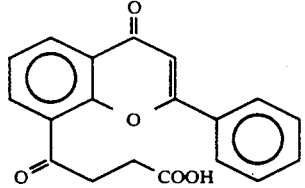

A mixture of 3 g (0.0075 mole) of the compound of Example 29, 30 ml of 6N hydrochloric acid and 30 ml of acetic acid was refluxed for 4 hours. This was then poured into water and ice, the product was dried, it was replaced in a solution of 5% NaHCO3 and acidified. The precipitate formed was dried and recrystallized in the MIBK-dioxane mixture. Weight obtained: 1.1 g (Yield: 45.5%); MP$_F$=207°-209° C.; IR V C=O (acid)=1720 cm$^{-1}$, V C=O (ketone)=1680 cm$^{-1}$, V C=O (pyrone)=1620 cm$^{-1}$; NMR (DMSO) δ in ppm in relation to TMS: 4H from 2.4 to 3.6 (m), 1H to 7.1 (s), 8H from 7.4 to 8.4 (m), 1H to 12.1 (exchangeable).

| Elemental analysis | C % | H % | O % |
|---|---|---|---|
| calculated: | 70.80 | 4.38 | 24.82 |
| found: | 70.50 | 4.43 | |

Example 31

Hydroxy-4-(Oxo-4-Phenyl-2°-4H-[1]Benzopyran-8-y)-Butyric Acid

C19H16O5    MW = 324.32    [Formula 102]

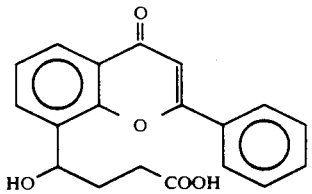

By treating 5 g (0.0155 mole) of the product of Example 30 with 9.5 g (0.0468 mole) of aluminum isopropylate in 100 ml of isopropanol and 40 ml of dioxane for 6 hours at reflux, 1.9 g of isopropyl hydroxy ester (MP$_K$=145° C.) was obtained after recrystallization in hexane. This was placed in 10 ml of water, 17 m with 0.45 g of sodium bicarbonate. The medium was brought to reflux for 4 hours 30 minutes, evaporated and the residue was replaced in water. The insoluble material was filtered, acidified with acetic acid, dried, and recrystallized in dioxane. Weight obtained: 0.7 g MP$_G$=198°-202° C.; IR V OH=3350 cm$^{-1}$, V C=O (acid)=1700 cm$^{-1}$, V C=O (pyrone)=1620 cm$^{-1}$; NMR (DMSO) δ in ppm in relation to TMS: 4H from 1.7 to 2.9 (m), 2H from 5.3 to 5.8 (m, of which 1H is exchangeable), 1H to 7.1 (s), 8H from 7.4 to 8.4 (m), 1H to 11.8 (exchangeable).

| Elemental analysis | C % | H % | O % |
|---|---|---|---|
| calculated: | 70.36 | 4.97 | 24.67 |
| found: | 70.56 | 4.72 | |

Example 32

Acetamido-2-Ethoxycarbonyl-2-(Oxo-4-Phenyl-2-4H-[1]Benzopyran-8-yl)-2 Ethyl Propionate C25H25NO7    MW = 451.46    [Formula 103]

-continued

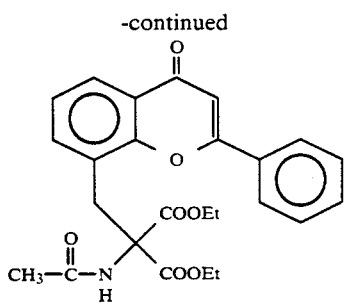

17.5 g (0.08 mole) of diethyl acetamidomalonate was added at 20° C. in 20 minutes to a suspension of 3 g (0.08 mole) of sodium hydride in 100 ml of toluene. This was left under stirring for 1 hour, then 25 g (0.08 mole) of bromomethyl-8-phenyl-2°-4H-[1]benzppyranone-4 were added in one hour. This was brought to a reflux for 8 hours and then hot filtered. The filtrate was evaporated under a vacuum, the residue was replaced in water, the solid was dried and recrystallized in ethanol. Weight obtained: 24.4 g (Yield: 67.6%); $MP_K=200°$ C.; IR V NH=3370 cm$^{-1}$ V C=O (ester)=1720 cm$^{-1}$ and 1760 cm$^{-1}$, V C=O (amide)=7670 cm$^{-1}$, V C=O (pyrone)=1640 cm$^{-1}$.

Example 33

Amino-2-(Oxo-4-Phenyl-2-4H-[1]Benzopyran-8-yl)-3-Propionic Acid Hydrochlorate $C_{18}H_{16}ClNO_4$    MW = 345.78    [Formula 104]

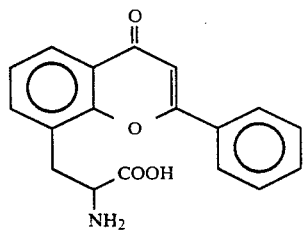

A mixture of 10 g (0.022 mole) of the compound of Example 32 and 400 ml of ½ HCl was brought to reflux for 4 hours. After a night of rest, the precipitate formed was dried and recrystallized in the ACOH-water mixture. Weight obtained: 4.4 g (Yield: 57.6%), $MP_G=243°$ C.; IR V OH, $NH_3^{(+)}=3500-2500$ cm$^{-1}$, V C=O (acid)=1740 cm$^{-1}$, V C=O (pyrone)1625 cm$^{-1}$; NMR (DMSO) δ in ppm in relation to TMS: 3H from 3.4 to 4.4 (m) 12H to 7.1 (s), 1H from 7.4 to 10 (m, of which 4H are exchangeable).

| Elemental analysis | C % | H % | Cl % | N % | O % |
|---|---|---|---|---|---|
| calculated: | 62.52 | 4.66 | 10.26 | 4.05 | 18.51 |
| found: | 62.66 | 4.89 | 10.35 | 4.11 | |

Following the experimental protocol outlined in Example 1 supra, the following compounds were prepared Following the experimental protocol outlines in Example 1 supra, the following compounds were prepared.

2-(2-Aminophenyl)-4-Oxo-4H-[1]Benzopyran-8-Acetic Acid $C_{17}H_{13}NO_4$    MW = 295.28    [Formula 105]

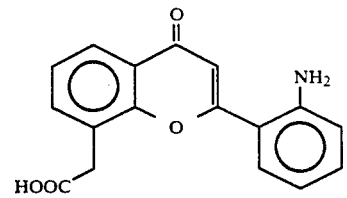

$PF_G=189°$ νC.; IR νC=0 (acid) 1710 cm$^{-1}$, νC=0 (pyrone)=1610 cm$^{-1}$

| Elemental analysis | C % | H % | N % | O % |
|---|---|---|---|---|
| calculated: | 69.14 | 4.44 | 4.74 | 21.61 |
| found: | 68.92 | 4.25 | 4.45 | |

2-(2-Chlorophenyl)-4-Oxo-4H-[1]Benzopyran-8-Acetic Acid $C_{17}H_{11}ClO_4$    MW = 314.715    [Formula 106]

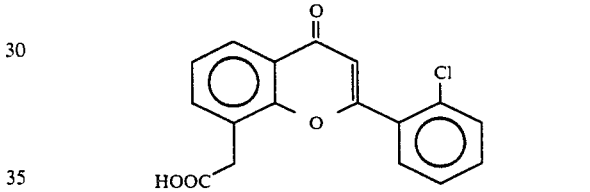

$PF_G=169°$ C.; IR νC=0 (acid)=1710 cm$^{-1}$, νC=0 (pyrone)=1620 cm$^{-1}$; NMR (DMSO) δ in ppm relative to TMS: 2 H at 4.3 (s), 8 H from 7.5 to 8.7 (m), 1 H at 11.7 (exchangeable).

| Elemental analysis | C % | H % | Cl % | O % |
|---|---|---|---|---|
| calculated: | 64.87 | 3.52 | 11.27 | 20.34 |
| found: | 65.09 | 3.48 | 11.53 | |

2-(3-Chlorophenyl)-4-Oxo-4H-[1]Benzopyran-8-Acetic Acid $C_{17}H_{11}ClO_4$    MW = 314.715    [Formula 107]

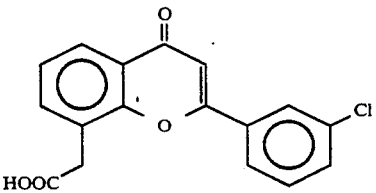

$PF_G=220°-222°$ C.; IR νC=0 (acid)=1730 cm$^{-1}$; νC=0 (pyrone)=1620 cm$^{-1}$; NMR (DMSO) δ in ppm relative to TMS: 2 H at 4 (s), 1 H from 7.5 (s), 7 H from 7.3 to 8.3 (m), 1 H at 13 (exchangeable).

| Elemental analysis | C % | H % | Cl % | O % |
|---|---|---|---|---|
| calculated: | 64.87 | 3.52 | 11.27 | 20.34 |

| -continued | | | | |
|---|---|---|---|---|
| Elemental analysis | C % | H % | Cl % | O % |
| found: | 64.59 | 3.53 | 11.28 | |

2-(2-Acetamidophenyl)-4-Oxo-4H-[1]Benzopyran-8-Acetic Acid

C$_{19}$H$_{15}$NO$_5$    MW = 337.318    [Formula 109]

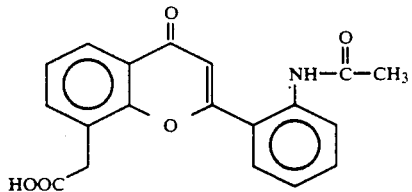

PF$_G$=196°-201° C.; IR $\nu$C=0 (acid)=1720 cm$^{-1}$; $\nu$C=0 (amide)=1660 cm$^{-1}$; $\nu$C=0 (pyrone)=1620 cm$^{-1}$; NMR (DMSO) δ in ppm relative to TMS: 3 H at 2 (s), 2 H at 3.8 (s), 1 H at 6.5 (s), 7 H from 7.3 to 8.2 (m), 1 H at 8.8 (exchangeable), 1 H at 11.5 (exchangeable).

| Elemental analysis | C % | H % | Cl % | O % |
|---|---|---|---|---|
| calculated: | 67.65 | 4.48 | 4.15 | 23.72 |
| found: | 67.42 | 4.24 | 4.11 | |

2-(4-Acetylphenyl)-4-Oxo-4H-[1]Benzopyran-8-Acetic Acid

C$_{19}$H$_{14}$O$_5$    MW = 322.302    [Formula 110]

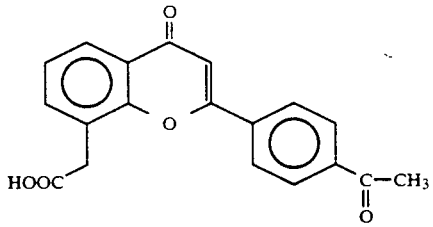

PF$_G$=253°-255° C.; IR $\nu$C=0 (pyrone)=1620 cm$^{-1}$; NMR (CF$_3$COOD) δ in ppm relative to TMS: 3 H at 2.8 (s), 2 H at 4.3 (m), 8 H from 7.7 to 8.5 (m).

| Elemental analysis | C % | H % | O % |
|---|---|---|---|
| calculated: | 70.80 | 4.38 | 24.82 |
| found: | 70.61 | 4.31 | |

2-(4-Acetamidophenyl)-4-Oxo-4H-[1]Benzopyran-8-Acetic Acid

C$_{19}$H$_{15}$NO$_5$    MW = 337.318    [Formula 111]

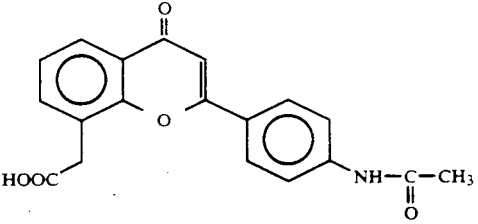

PF$_G$=284°-288° C. IR $\nu$C=0 (acid)=1720 cm$^{-4}$; $\nu$C=0 (amide+pyrone) =1630 cm$^{-4}$; NMR (DMSO) δ in ppm relative to TMS: 3 H at 2 (s), 2 H at 4 (s), 1 H at 6.8 (s), 7 H from 7.1 to 8.1 (m), 1 H at 9.8 (exchangeable), 1 H at 12 (exchangeable).

| Elemental analysis | C % | H % | N % | O % |
|---|---|---|---|---|
| calculated: | 67.65 | 4.48 | 4.15 | 23.72 |
| found: | 67.70 | 4.40 | 4.12 | |

2-(2-Diethylaminoethoxyphenyl)-4-Oxo-4H-[1]-Benzopyran-8-Acetic Acid

C$_{23}$H$_{25}$ClNO$_5$    MW = 431.903    [Formula 112]
(chlorhydrate)

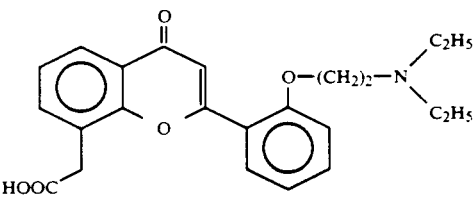

PF$_G$=1780°-182° C. C$_1$(chlorhydrate); IR $\nu$C=0 (acid)=1720 cm$^{-4}$; $\nu$C=0 (pyrone)=1640 cm$^{-4}$; NMR (DMSO) δ in ppm relative to TMS: 6 H at 1 (t), 6 H from 2.8 to 3.8 (m), 1 H from 3.9 to 4.2 (m), 8 H from 6.8 to 8 (m), 1 H at 11 (exchangeable).

| Elemental analysis | C % | H % | Cl % | N % | O % |
|---|---|---|---|---|---|
| calculated: | 63.96 | 6.07 | 8.21 | 3.24 | 18.52 |
| found: | 63.96 | 6.12 | 8.19 | 3.24 | |

2-(3-Nitro-4-Chlorophenyl)-4-Oxo-4H-[1]-Benzopyran-8-Acetic Acid

C$_{17}$H$_{10}$ClNO$_4$    MW = 359.715    [Formula 113]

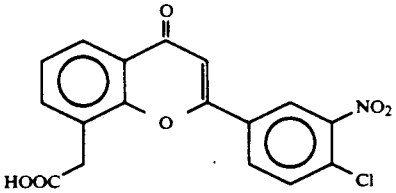

PF$_G$=232°-234° C. IR $\nu$C=0 (acid)=1720 cm$^{-1}$; $\nu$C=0 (pyrone)=1640 cm$^{-4}$; NMR (DMSO) δ in ppm relative to TMS: 2 H at 4 (s), 7 H from 7 to 8.8 (m), 1 H at 12.1 (exchangeable).

| Elemental analysis | C % | H % | Cl % | N % | O % |
|---|---|---|---|---|---|
| calculated: | 56.76 | 2.80 | 9.86 | 3.89 | 26.69 |
| found: | 56.82 | 2.69 | 9.78 | 3.90 | |

2-(2,4-Dimethoxyphenyl-4-Oxo-4H-[1]-Benzopyran-8-Acetic Acid $C_{19}H_{16}O_6$    MW = 340.185    [Formula 114]

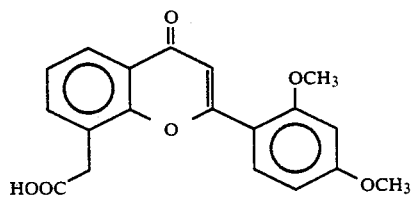

$PF_G$=225°-227° C. IR $\nu C=O$ (acid)=1710 cm$^{-1}$; $\nu C=O$ (pyrone)=1620 cm$^{-1}$; NMR (DMSO) δ in ppm relative to TMS: 2 H at 3.5 (s), 3 H from 3.9 (s), 3 H at 4 (s), 7 H from 6.8 to 8, 1 H at 12.2 (exchangeable).

| Elemental analysis | C % | H % | O % |
|---|---|---|---|
| calculated: | 67.05 | 4.74 | 28.21 |
| found: | 67.23 | 4.63 | |

2-(4-Diethylaminoethoxyphenyl)-4-Oxo-4H-[1]-Benzopyran-8-Acetic Acid $C_{23}H_{26}ClNO_2$    MW = 431.92    [Formula 115]
(chlorhydate)

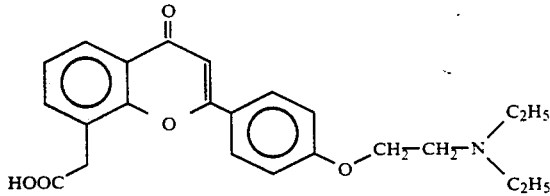

$PF_G$=194°-199° C. (chlorhydate); IR $\nu C=O$ (acid)=1720 cm$^{-1}$; $\nu C=O$ (pyrone)=1630 cm$^{-1}$; NMR (DMSO) δ in ppm relative to TMS: 8 H from 3 to 4.7 (m), 8 H from 6.8 to 8.3 (m), 1 H from 10.4 to 10.8 (exchangeable).

| Elemental analysis | C % | H % | Cl % | N % | O % |
|---|---|---|---|---|---|
| calculated: | 63.96 | 6.07 | 8.21 | 3.24 | 18.57 |
| found: | 63.50 | 6.04 | 8.30 | 3.45 | |

2-(4-Carbamolyphenyl)-4-Oxo-4H-[1]-Benzopyran-8-Acetic Acid $C_{18}H_{13}NO_5$    MW = 323.292    [Formula 116]

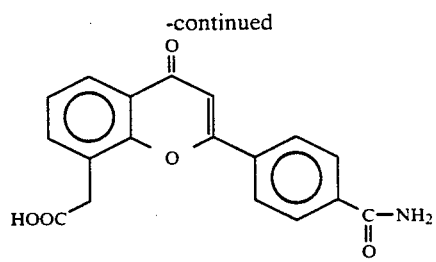

$PF_G$=228°-290° C.; IR $\nu C=O$ (acid)=1710 cm$^{-1}$; $\nu C=O$ (amide+pyrone)=1640 cm$^{-1}$

| Elemental analysis | C % | H % | N % | O % |
|---|---|---|---|---|
| calculated: | 66.87 | 4.05 | 4.33 | 24.75 |
| found: | 66.35 | 4.35 | 4.46 | |

[[Methyl-2-Thiazolyl-4-Phenyl-2-Oxo-4-4H[1]Benzopyran-8-Acetic Acid $C_{21}H_{15}NO_4S$    MW = 377.398    [Formula 117]

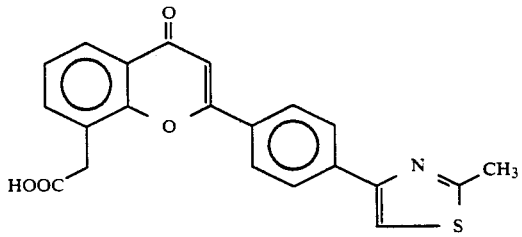

$PF_G$=246°-248° C. IR $\nu C=O$ (acid)=1720 cm$^{-1}$; $\nu C=O$ (pyrone)=1620 cm$^{-1}$; NMR (DMSO) δ in ppm relative to TMS: 3 H at 4 (s), 2H at 3.8, 1 H at 7 (s), 8 H from 7.1 to 8.1 (m), 1 H at 12.6 (exchangeable).

| Elemental analysis | C % | H % | N % | O % | S % |
|---|---|---|---|---|---|
| calculated: | 66.83 | 4.01 | 3.71 | 16.96 | 8.50 |
| found: | 66.73 | 3.95 | 3.66 | | 8.56 |

2-(2-Chlorophenyl)-4-Oxo-4H-[1]-Benzopyran-8-Acetic Acid $C_{19}H_{17}N_3O_4$    MW = 351.35    [Formula 118]

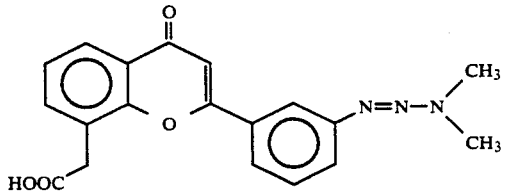

$PF_G$=173°-175° C. IR $\nu C=O$ (acid)=1710 cm$^{-1}$; $\nu C=O$ (pyrone)=1620 cm$^{-1}$; NMR (DMSO) δ in ppm relative to TMS: 6 H at 3.25 (s), 2H at 4 (s), 1 H at 7 (s), 7 H from 7.2 to 8 (m), 1 H at 12.3 (exchangeable).

| Elemental analysis | C % | H % | N % | O % |
|---|---|---|---|---|
| calculated: | 64.95 | 4.88 | 11.96 | 18.22 |

-continued

| Elemental analysis | C % | H % | N % | O % |
|---|---|---|---|---|
| found: | 64.72 | 4.85 | 12.04 | |

2-(2-Amino-4-Thiazolylphenyl)-4-Oxo-4H-[1]-Benzopyran-8-Acetic Acid

C$_{20}$H$_{14}$O$_4$S    MW = 378.388    [Formula 119]

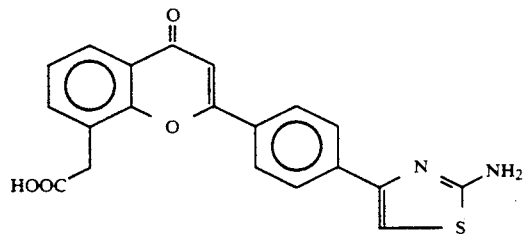

PF$_G$=263°-265° C. IR $\nu$C=O (acid)=1710 cm$^{-1}$; $\nu$C=O (pyrone)=1620 cm$^{-1}$; NMR (DMSO) δ in ppm relative to TMS: 2 H at 4 (s), 11 H from 7 to 8.2 (m, with 2 H exchangeable), 1 H at 12.9 (exchangeable).

| Elemental analysis | C % | H % | O % |
|---|---|---|---|
| calculated: | 67.05 | 4.75 | 28.21 |
| found: | 67.70 | 4.54 | 7.12 |

2-(3,5-Dimethoxyphenyl)-4-Oxo-4H-[1]-Benzopyran-8-Acetic Acid

C$_{19}$H$_{16}$O$_6$    MW = 340.318    [Formula 120]

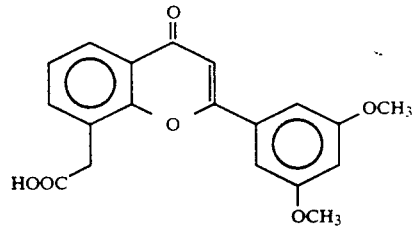

PF$_G$=261°-263° C. IR $\nu$C=O (acid)=1720 cm$^{-1}$; $\nu$C=O (pyrone)=1630 cm$^{-1}$; NMR (DMSO) δ in ppm relative to TMS: 6 H at 3.9 (s), 2 H at 4 (s), 7 H from 6.5 to 8 (m), 1 H at 12.9 (exchangeable).

| Elemental analysis | C % | H % | O % |
|---|---|---|---|
| calculated: | 67.05 | 4.74 | 28.21 |
| found: | 67.20 | 4.54 | |

2-(4-Pyridyl)-4-Oxo-4H-[1]-Benzopyran-8-Acetic Acid

C$_{16}$H$_{11}$NO$_4$    MW = 281.256    [Formula 121]

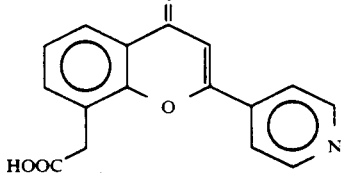

PF$_G$=275°-277° C. IR $\nu$C=O (acid)=1720 cm$^{-1}$; $\nu$C=O (pyrone)=1600 cm$^{-1}$; NMR (DMSO+CF$_3$COOD)δ in ppm relative to TMS: 2 H at 4 (s), 8H from 7.3 to 8.8 (m).

| Elemental analysis | C % | H % | N % | O % |
|---|---|---|---|---|
| calculated: | 68.32 | 3.94 | 4.98 | 22.76 |
| found: | 67.94 | 4.09 | 5.12 | |

2-(2-Pyridyl)-4-Oxo-4H-[1]-Benzopyran-8-Acetic Acid

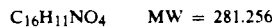
C$_{16}$H$_{11}$NO$_4$    MW = 281.256    [Formula 122]

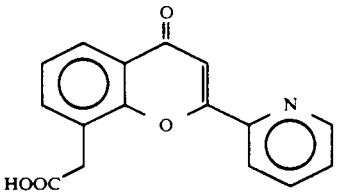

PF$_G$=221°-223° C. IR $\nu$C=O (acid)=1720-1740 cm$^{-1}$; $\nu$C=O (pyrone)=1640 cm$^{-1}$; NMR (DMSO) δ in ppm relative to TMS: 2 H at 4.1 (s), 1 H at 7.2 (s) 7 H from 7.25 to 9 (m), 1 H at 13 (exchangeable).

| Elemental analysis | C % | H % | N % | O % |
|---|---|---|---|---|
| calculated: | 68.32 | 3.94 | 4.98 | 22.76 |
| found: | 68.50 | 3.89 | 4.86 | |

2-(4-Hexylphenyl)-4-Oxo-4H-[1]-Benzopyran-8-Acetic Acid

C$_{23}$H$_{24}$O$_4$    MW = 364.422    [Formula 123]

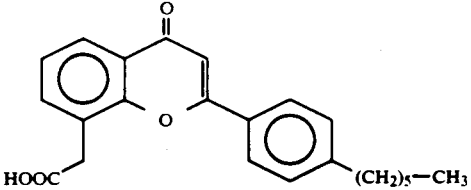

PF$_G$=154°-156° C. IR $\nu$C=O (acid)=1720 cm$^{-1}$; $\nu$C=O (pyrone)=1620 cm$^{-1}$; NMR (DMSO) δ in ppm relative to TMS: 13 H from 0.7 to 2.8 (m), 2 H at 4 (s), 1 H at 7 (s), 7 H from 7.2 to 8.1 (m), 1 H at 12.9

| Elemental analysis | C % | H % | O % |
|---|---|---|---|
| calculated: | 75.80 | 6.64 | 17.56 |
| found: | 75.50 | 6.49 | |

2-(3-Methylphenyl)-4-Oxo-4H-[1]-Benzopyran-8-Acetic Acid $C_{18}H_{14}O_4$    MW = 294.292    [Formula 124]

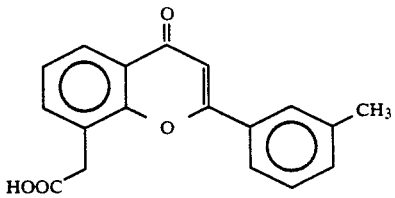

PF$_G$=252°-254° C. IR $\nu$C=O (acid)=1720 cm$^{-1}$; $\nu$C=O (pyrone)=1620 cm$^{-1}$; NMR (CF$_3$COOD) δ in ppm relative to TMS: 3 H at 2.55 (s), 2H at 4.5 (m), 8 H from 7.5 to 8.6 (m).

| Elemental analysis | C % | H % | O % |
|---|---|---|---|
| calculated: | 73.46 | 4.80 | 21.75 |
| found: | 73.74 | 4.86 | |

2-(4-Benzoylphenyl)-4-Oxo-4H-[1]-Benzopyran-8-Acetic Acid $C_{24}H_{16}O_4$    MW = 384.368    [Formula 125]

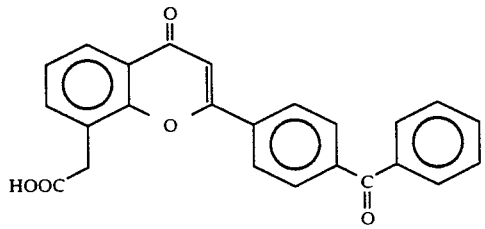

PF$_G$=257°-259° C. IR $\nu$C=O (acid)=1720 cm$^{-1}$; $\nu$C=O (benzoyl)=1650 cm$^{-1}$; $\nu$C=O (pyrone)=1620 cm$^{-1}$; NMR )CF$_3$COOD)δ in ppm relative to TMS: 2 H at 4.5 (s), 13 H from 7.5 to 8.7 (m).

| Elemental analysis | C % | H % | O % |
|---|---|---|---|
| calculated: | 74.99 | 4.20 | 20.81 |
| found: | 75.11 | 4.09 | |

2-(4-Undecylphenyl)-4-Oxo-4H-[1]-Benzopyran-8-Acetic Acid $C_{28}H_{34}O_4$    MW = 434.552    [Formula 126]

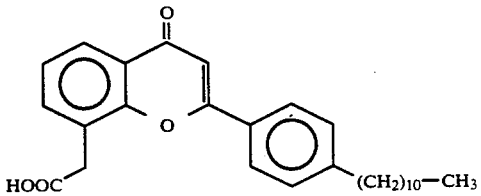

PF$_G$=150°-152° C. IR $\nu$C=O (acid)=1710 cm$^{-1}$; $\nu$C=O (pyrone)=1620 cm$^{-1}$; NMR (CF$_3$COOD) δ in ppm relative to TMS: 23 H from 0.6 to 1.7 (m), 2 H at 4.5 (s), 8 H from 7.5 to 8.4 (m).

| Elemental analysis | C % | H % | O % |
|---|---|---|---|
| calculated: | 77.39 | 7.89 | 14.73 |
| found: | 77.34 | 7.87 | |

Nitro-3-, Phenyl-4-Phenyl)-2-Oxo-4H-[1]-Benzopyran-8-Acetic Acid $C_{23}H_{15}NO_6$    MW = 401.358    [Formula 127]

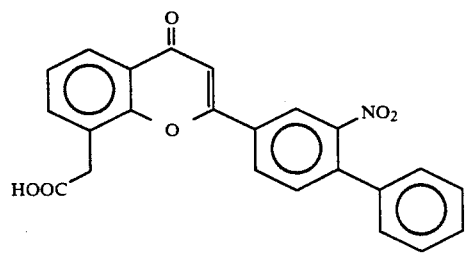

PF$_G$=270°-272° C. IR $\nu$C=O (acid)=1720 cm$^{-1}$; $\nu$C=O (pyrone)=1620 cm$^{-1}$; NMR (DMSO) δ in ppm relative to TMS: 2 H at 4 (s), 12 H from 7.2 to 8.7 (m), 1 H at 12.9 (exchangeable).

| Elemental analysis | C % | H % | N % | O % |
|---|---|---|---|---|
| calculated: | 68.88 | 3.77 | 3.49 | 23.92 |
| found: | 68.72 | 3.66 | 3.35 | |

2-(4-Trifluoromethylphenyl)-4-Oxo-4H-[1]-Benzopyran-8-Acetic Acid $C_{18}H_{11}F_3O_4$    MW = 348.268    [Formula 128]

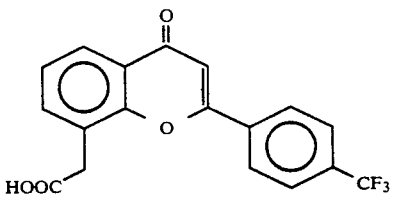

PF$_G$=216°-218° C. IR $\nu$C=O (acid)=1720 cm$^{-1}$; $\nu$C=O (pyrone)=1640 cm$^{-1}$; NMR (DMSO) δ in ppm relative to TMS: 2 H at 4 (s), 8 H from 7.1 to 8.4 (m), 1 H at 12.8 (exchangeable).

| Elemental analysis | C % | H % | F % | O % |
|---|---|---|---|---|
| calculated: | 63.07 | 3.18 | 16.37 | 18.38 |
| found: | 63.02 | 3.32 | 16.37 | |

2-(4-Dimethyltriazenylphenyl)-4-Oxo-4H-[1]-Benzopyran-8-Acetic Acid $C_{19}H_{17}N_3O_4$    MW = 351.35    [Formula 129]

-continued

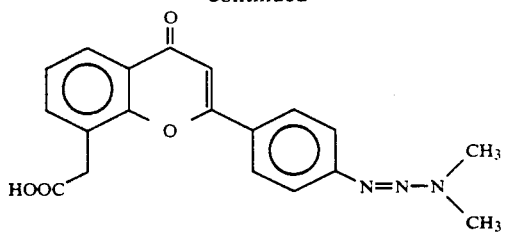

$PF_G=209°-211°$ C. IR $\nu C=O$ (acid)=1720 cm$^{-1}$; $\nu C=O$ (pyrone)=1620 cm$^{-1}$; NMR (DMSO) δ in ppm relative to TMS: 6 H at 3.3 (s), 2H at 4 (s), 1 H at 7 (s), 7 H from 7.2 to 8.1 (m), 1 H at 12.8 (exchangeable).

| Elemental analysis | C % | H % | N % | O % |
|---|---|---|---|---|
| calculated: | 64.95 | 4.88 | 11.96 | 18.22 |
| found: | 64.75 | 4.95 | 12.25 | |

2-(3-Nitro-4-Methoxyphenyl)-4-Oxo-4H-[1]-Benzopyran-8-Acetic Acid $C_{18}H_{13}NO_7$    MW = 355.292    [Formula 130]

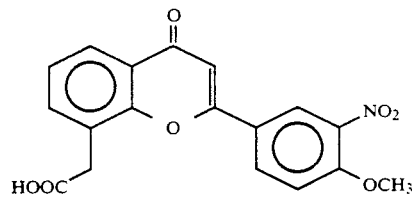

$PF_G=254°-256°$ C. IR $\nu C=O$ (acid)=1720 cm$^{-1}$; $\nu C=O$ (pyrone)=1620 cm$^{-1}$; NMR (CF$_3$COOD): 3 H at 4.1 (s), 2 H at 4.3 (s), 7 H from 7.1 to 6 (m).

| Elemental analysis | C % | H % | N % | O % |
|---|---|---|---|---|
| calculated: | 60.85 | 3.69 | 3.94 | 31.52 |
| found: | 61.07 | 3.68 | 4.16 | |

2-(4-Terbutylphenyl)-4-Oxo-4H-[1]-Benzopyran-8-Acetic Acid $C_{21}H_{20}O_4$    MW = 336.37    [Formula 131]

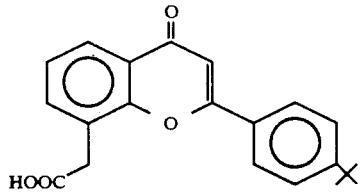

$PF_G=240°-242°$ C. IR $\nu C=O$ (acid)=1720 cm$^{-1}$; $\nu C=O$ (pyrone)=1610 cm$^{-1}$; NMR (DMSO) δ in ppm relative to TMS: 6 H at 1.2 (s), 2H at 4.5 (s), 8 H from 7.1 to 8.3 (m), 1 H at 12.9 (exchangeable).

| Elemental analysis | C % | H % | O % |
|---|---|---|---|
| calculated | 74.98 | 5.99 | 19.03 |
| found: | 74.76 | 5.85 | |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound of one of the following formulae:

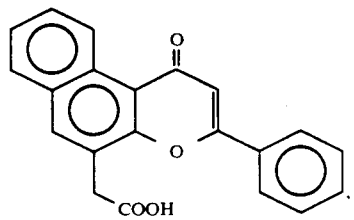
(1)

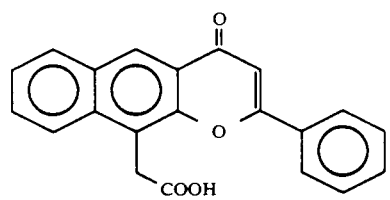
(2)

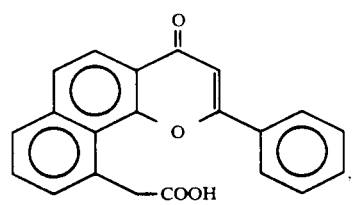
(3)

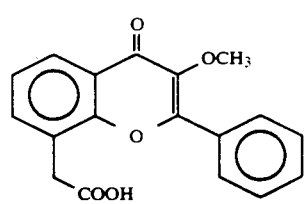
(4)

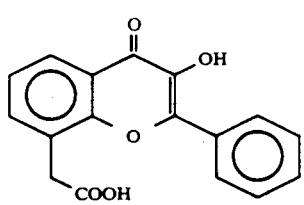
(7)

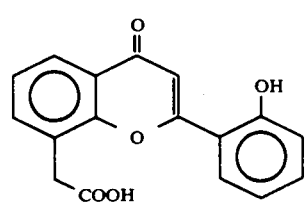
(10)

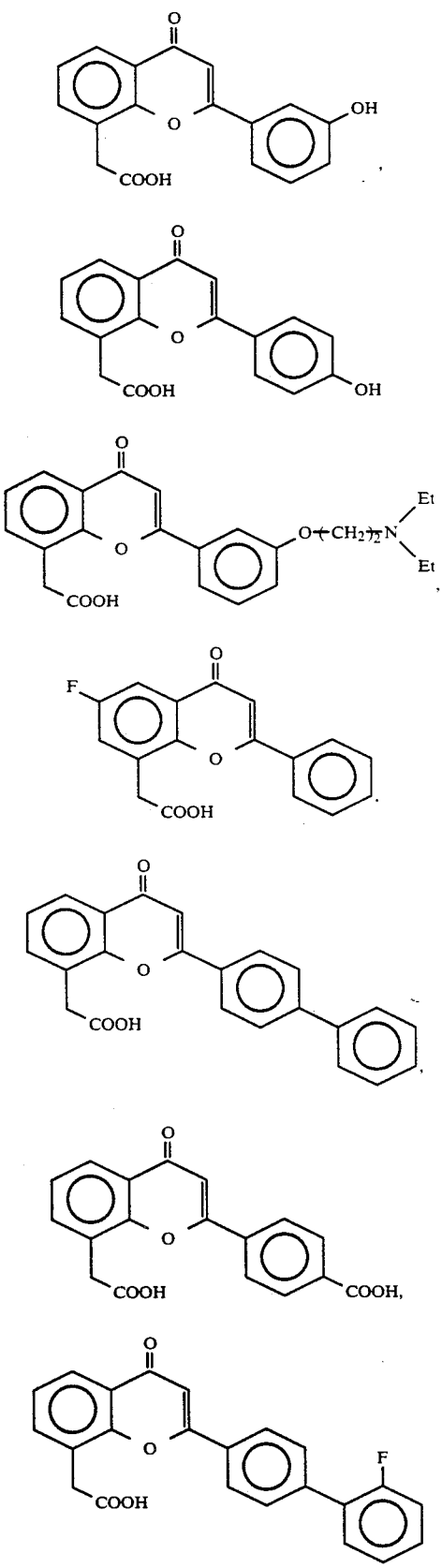

-continued
(32)
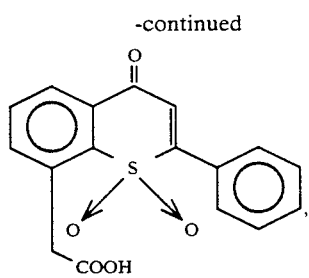
(33)
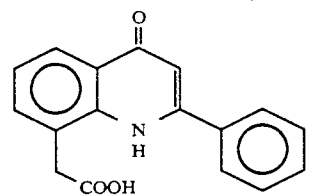
(34)
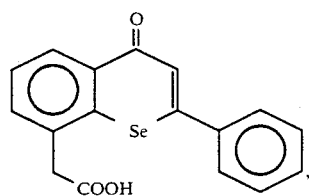
(35)
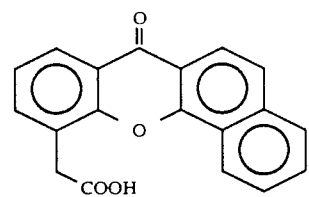
(36)
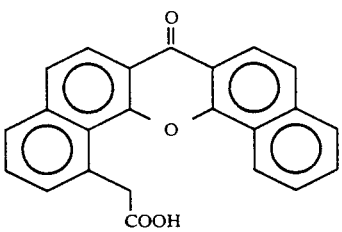
(37)
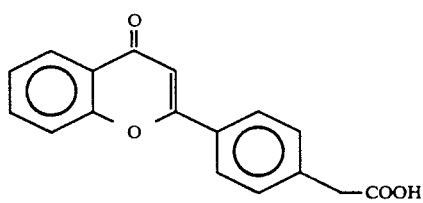
(38)
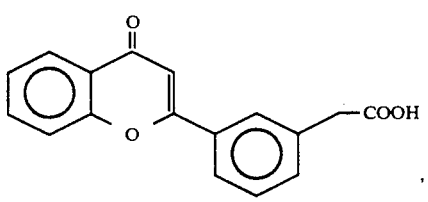
-continued
(39)
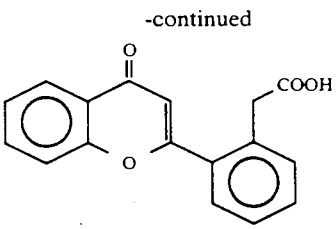
(40)
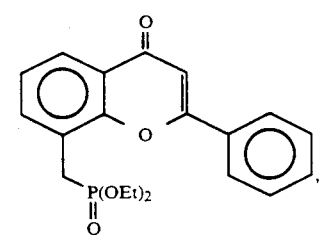
(41)
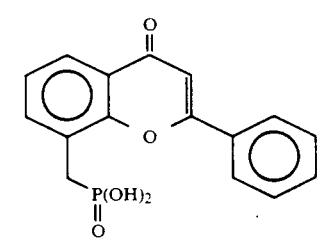
(42)
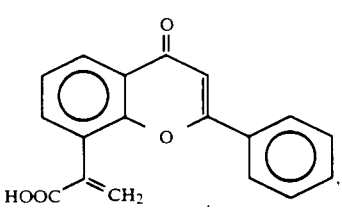
(43)
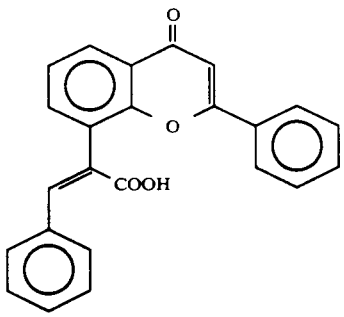
(44)
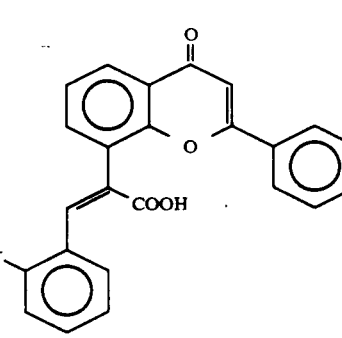

-continued

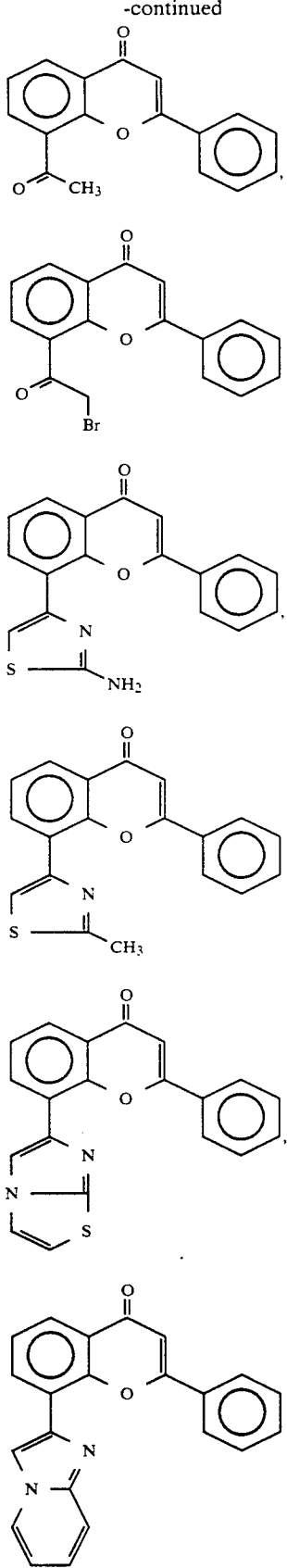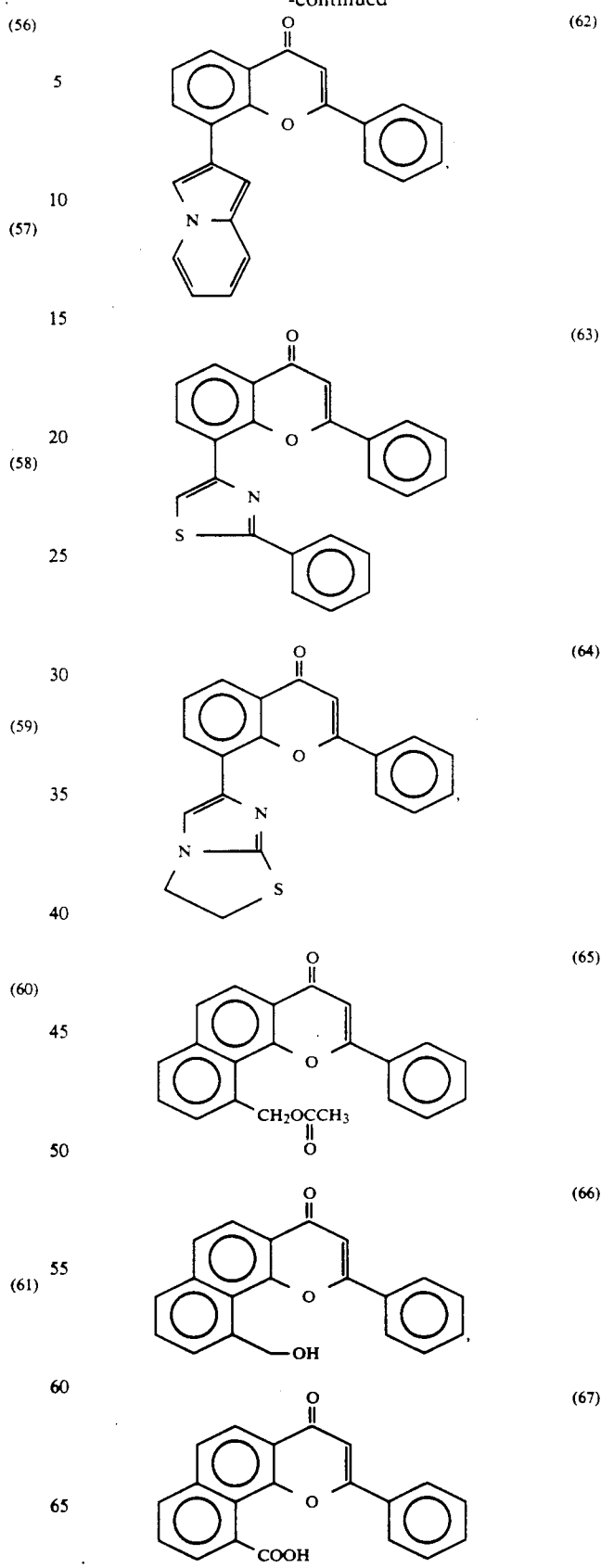

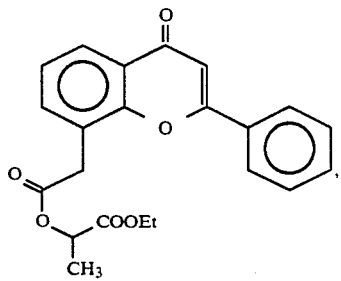 (68)
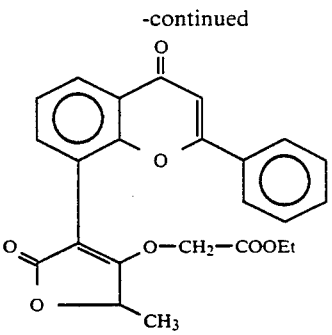 (73)
(69)
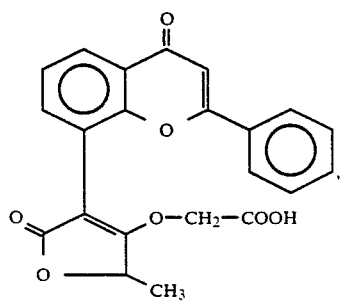 (74)
(70)
(75)
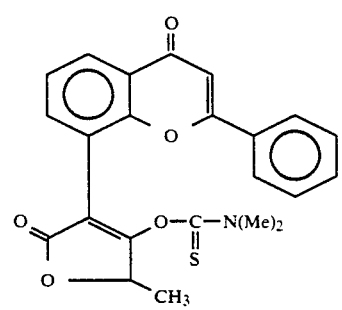
(71)
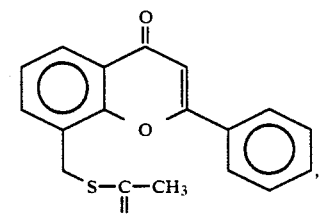 (76)
(72)
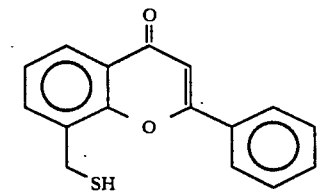 (77)
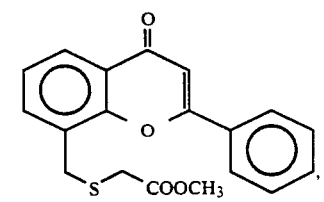 (78)

-continued
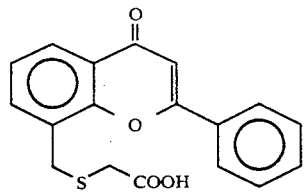 (79)
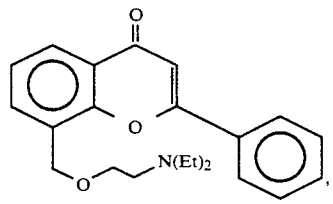 (80)
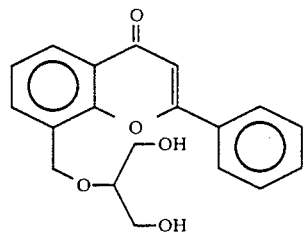 (81)
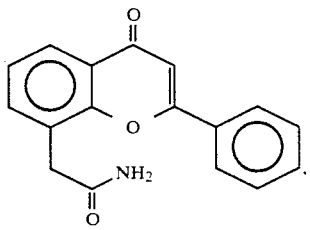 (82)
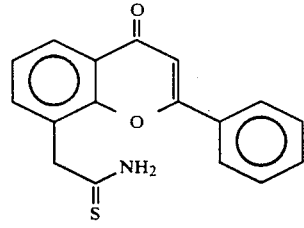 (83)
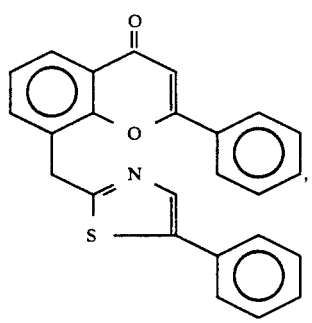 (84)
-continued
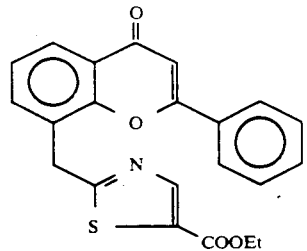 (85)
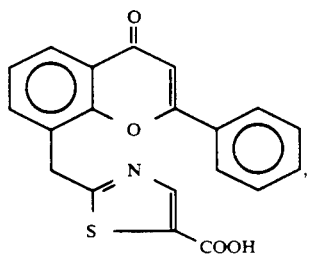 (86)
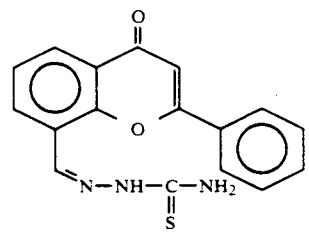 (87)
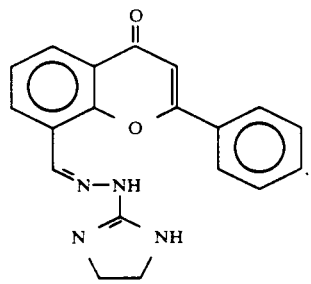 (88)
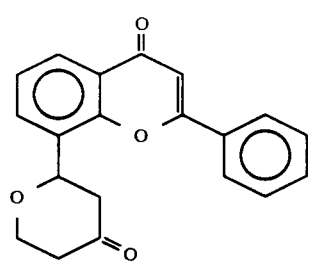 (89)
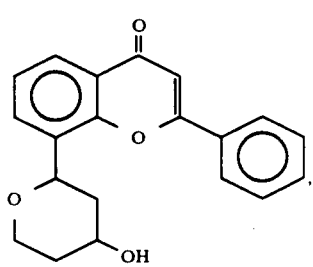 (90)

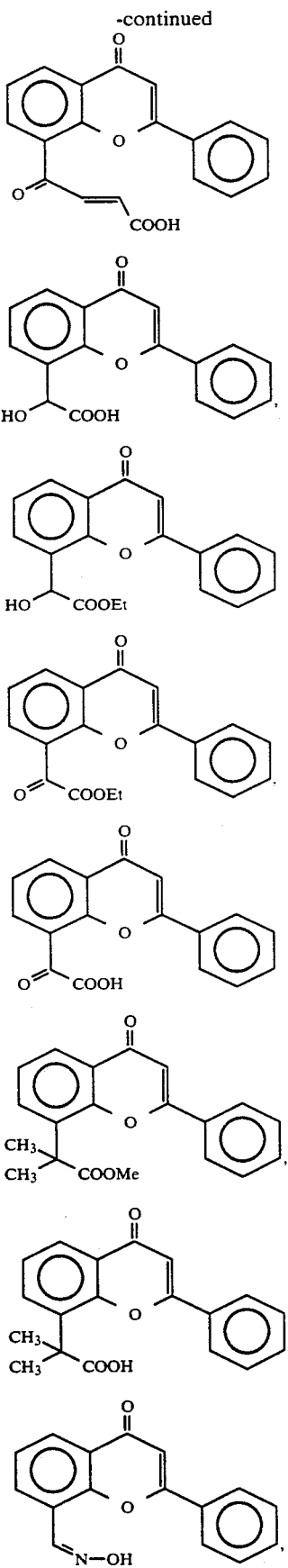
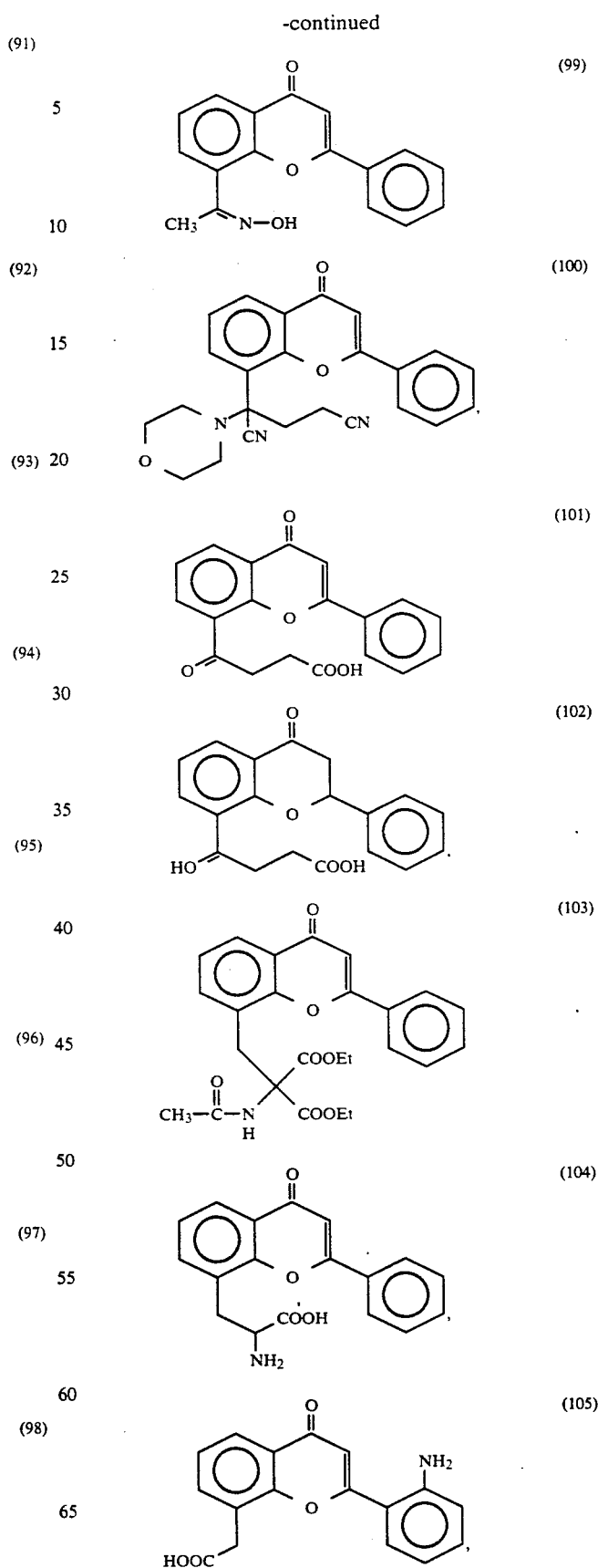

-continued
(109) 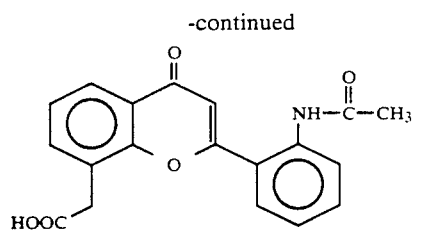
(110) 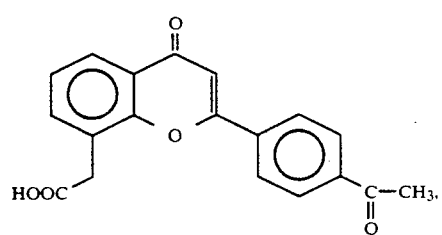
(111) 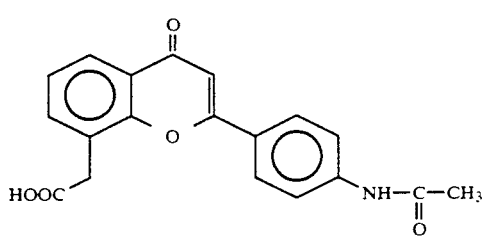
(112) 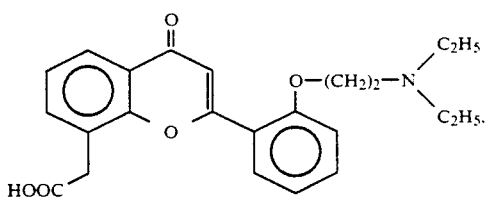
(113) 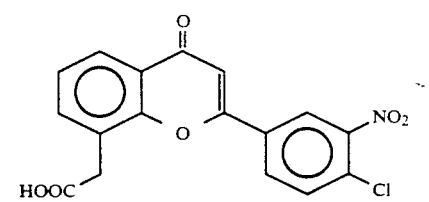
(115) 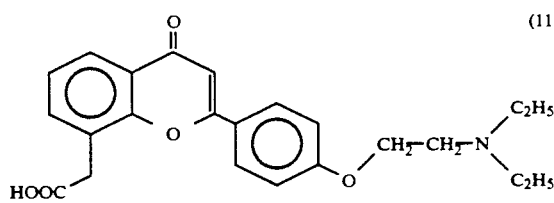
(116) 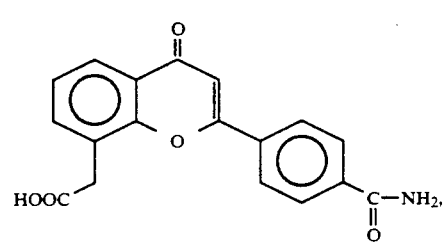
-continued
(117) 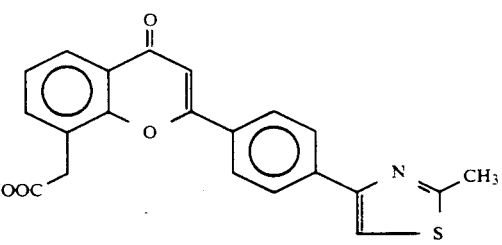
(118) 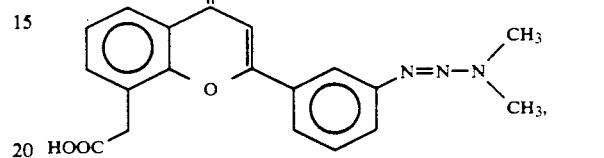
(119) 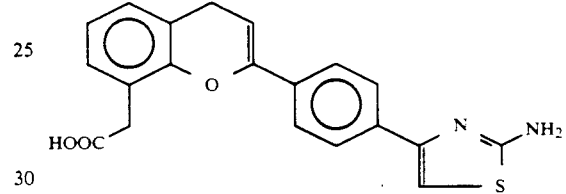
(121) 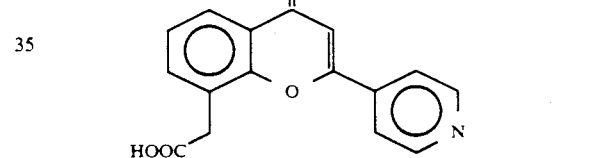
(122) 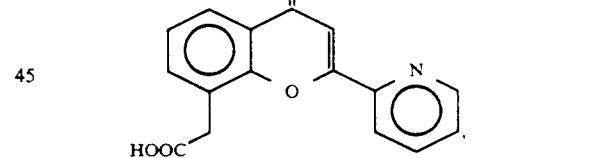
(123) 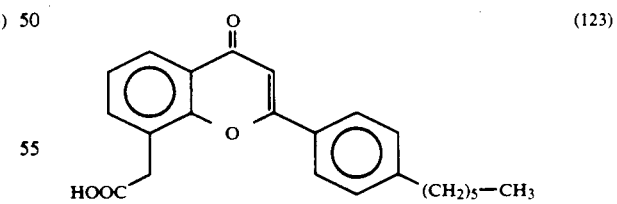
(125) 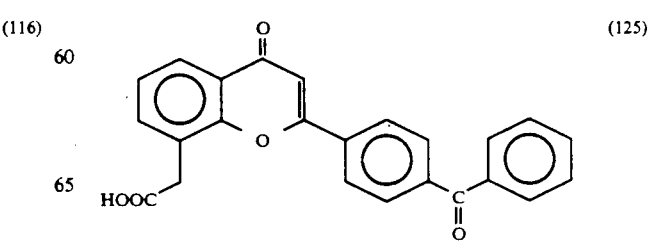

-continued
(126)
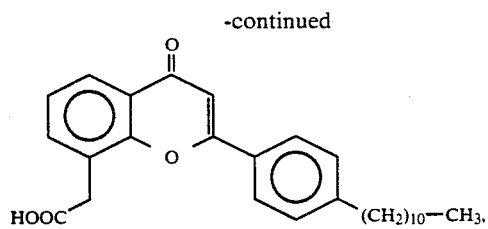
(127)
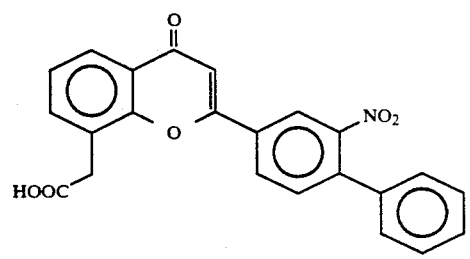
(129)
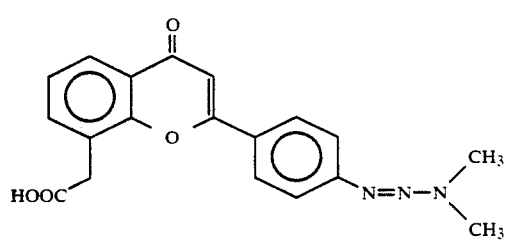
or
(130)
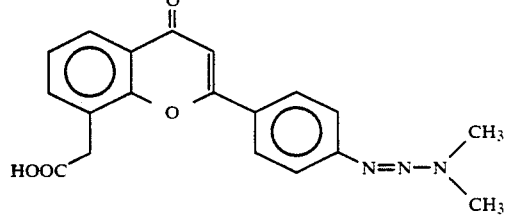
2. The compound of claim 1, of one of the following formulae:
(1)
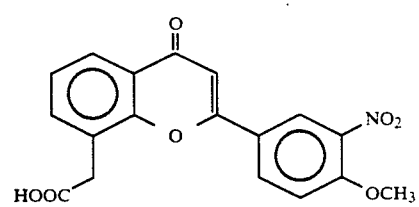
(2)
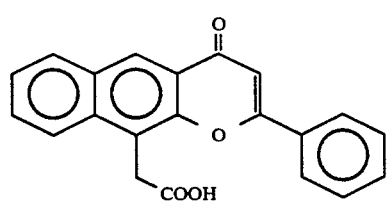
-continued
(3)
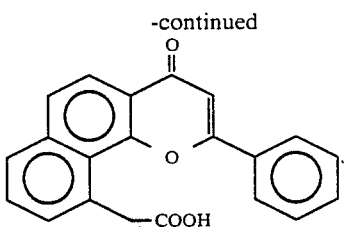
(4)
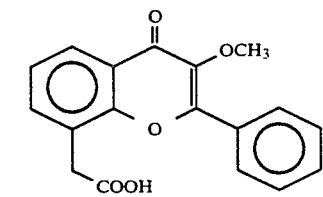
(7)
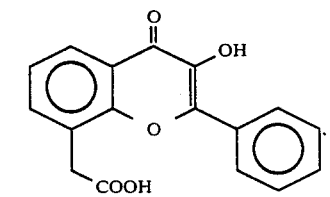
(10)
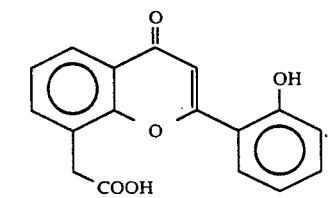
(11)
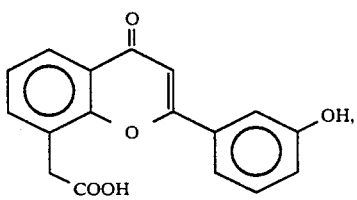
(12)
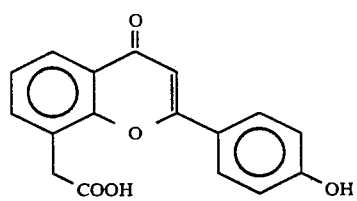
(27)
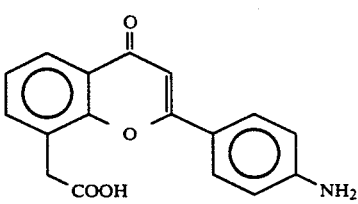
(30)
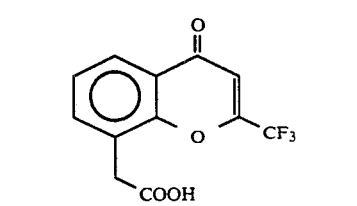

-continued
(105) 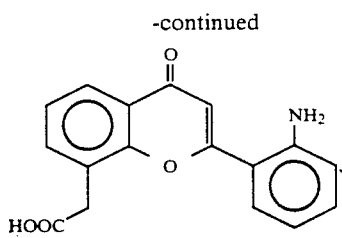
(109) 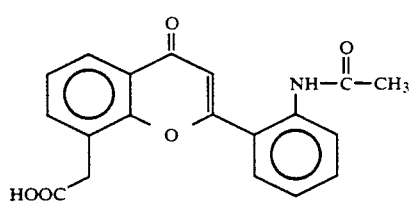
(110) 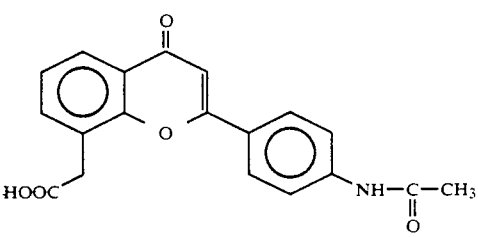
(111) 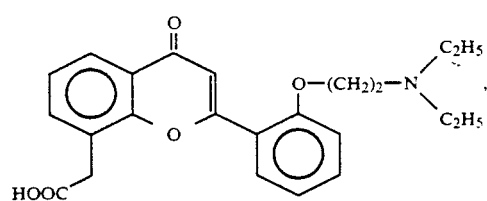
(112) 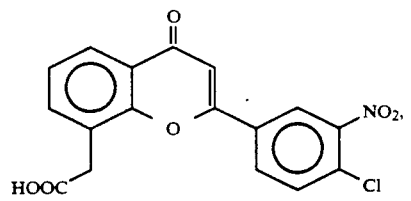
(113) 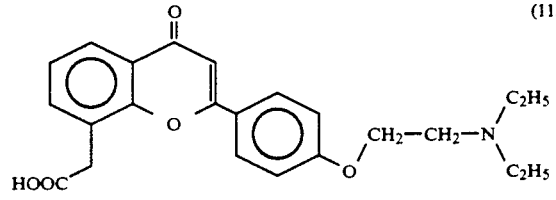
(115) 
-continued
(116) 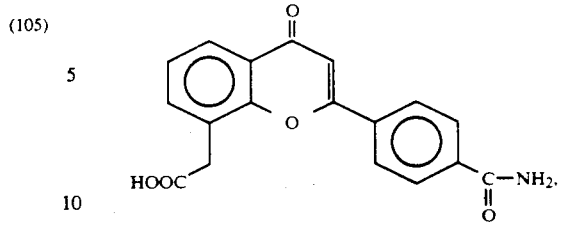
(117) 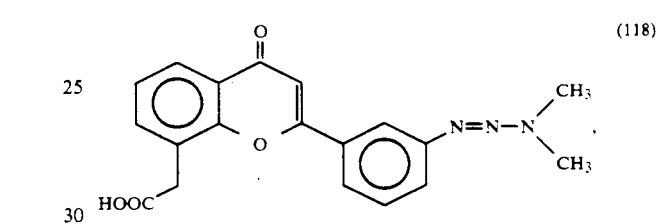
(118) 
(111) 
(119) 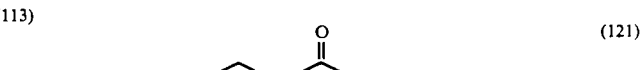
(121) 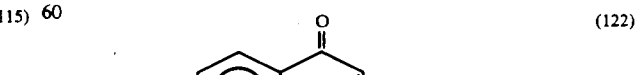
(122) 

-continued
(123)
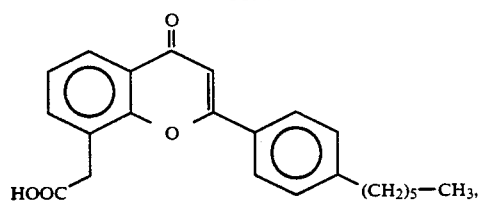
(125)
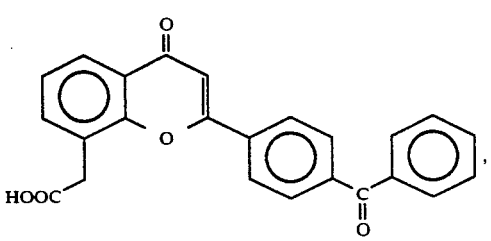
(126)
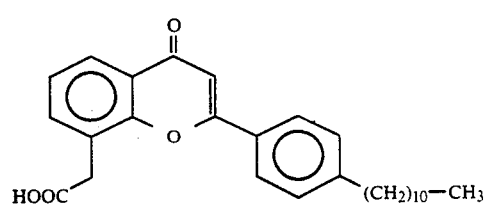
(127)
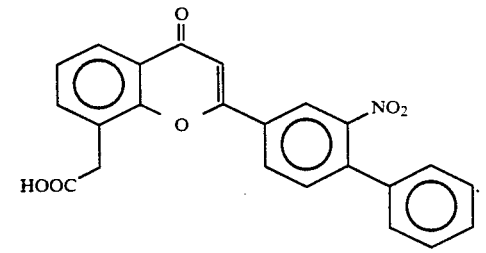
(129)
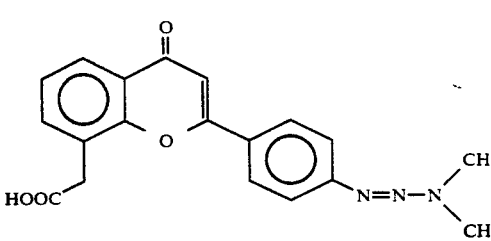
(130)
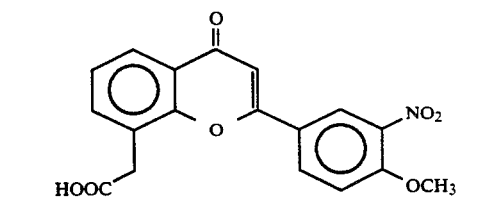
(42)
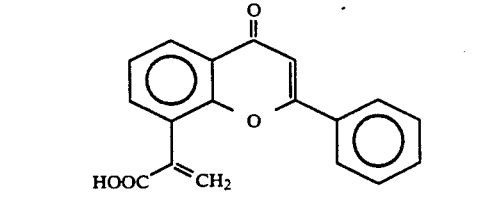
-continued
(43)
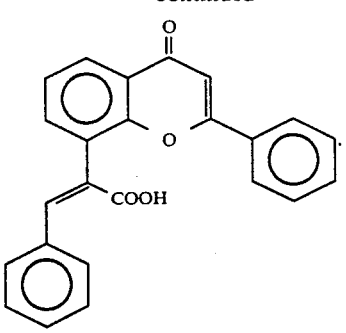
(44)
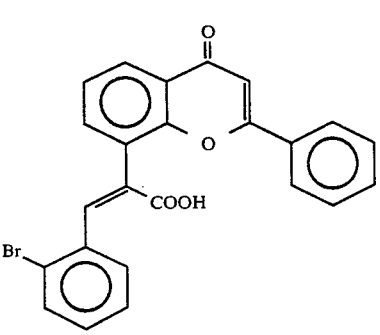
(45)
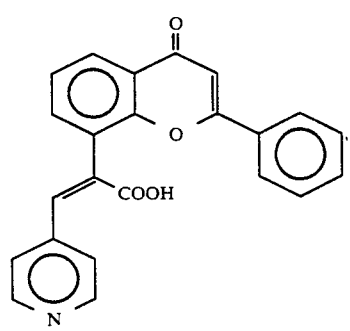
(46)
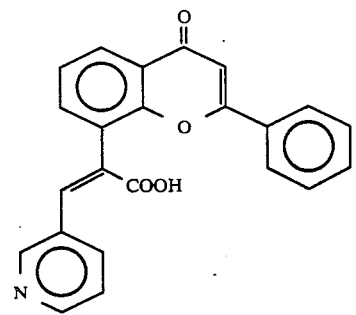
(65)
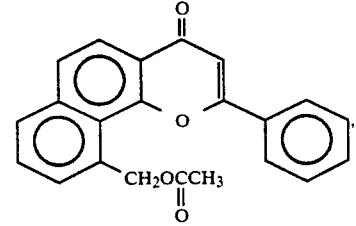

-continued

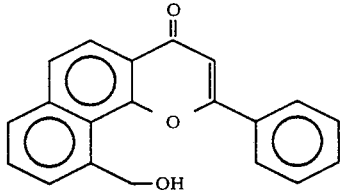 (66)

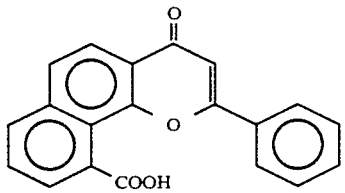 (67)

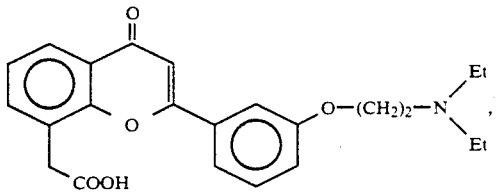 (13)

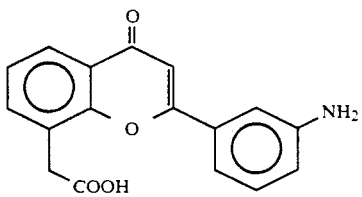 (26)

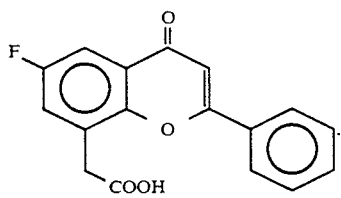 (15)

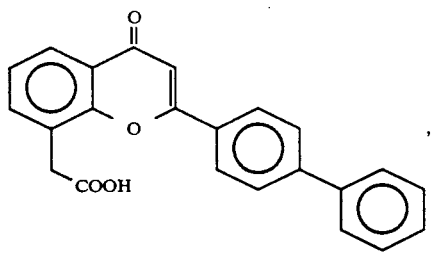 (19)

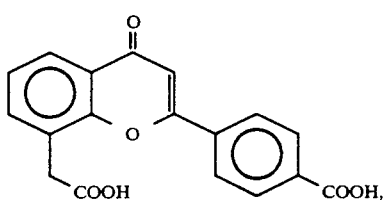 (21)

-continued

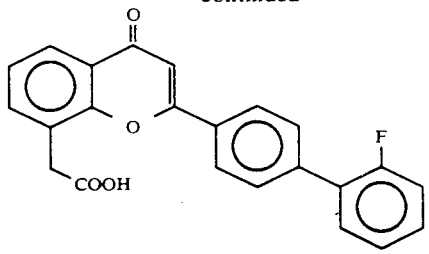 (22)

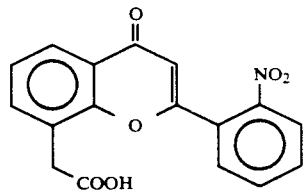 (23)

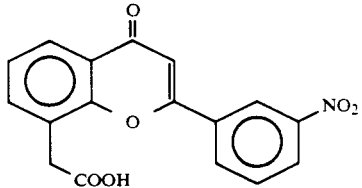 (24)

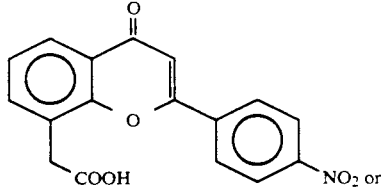 (25)

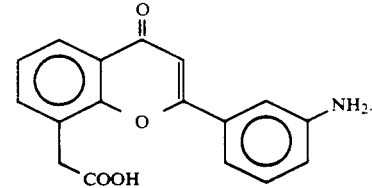 (26)

3. The compound of claim 1, wherein said compound is a compound of one of the following formula: (1), (2), (3), (4), (7), (10), (11) (12), or (13).

4. The compound of claim 1, said compound being a compound of the formula (15), (19), (21), (22), (23) (24), (25), and (26).

5. The compund of claim 1, wherein said compound is a compound of the following formula (27), (30), (31), (32) (33), (34), (35), (36), (37), (38), (39), and (40).

6. The compund of claim 1, wherein said compound is of the formula (41), (42), (43), (44), (45), (46), (47), (48), (49), (50), (51), (52), and (53).

7. The compound of claim 1, wherein said compound is of the formula (54), (55) (56), (57), (58), (59), (60), (61), (62), (63), (64), (65), (66), and (67).

8. The compound of claim 1, wherein said compound is of the formula (68), (69) (70), (71), (72), (73), (74), (75), (76), (77), (78), (79), (80), and (81).

9. The compound of claim 1, wherein said compound is of the formula (82), (83) (84), (85), (86), (87), (88), (89), (90), (91), (92), (93), (94), and (95).

10. The compound of claim 1, wherein said compound is of the formula (96), (97) (98), (99), (100), (101), (102), (103), (104), (105), and (109).

11. The compound of claim 1, wherein said compound is of the formula (110), (111), (112) (113), (115), (116), (117), (118), (119), (121), (122), and (123).

12. The compound of claim 1, wherein said compound is of the formula (125), (126) (127), (129), and (130).

* * * * *